US012758082B2

(12) United States Patent
Kim et al.

(10) Patent No.: US 12,758,082 B2
(45) Date of Patent: Oct. 13, 2026

(54) SHOE CARE APPARATUS

(71) Applicant: LG ELECTRONICS INC., Seoul (KR)

(72) Inventors: Jae Young Kim, Seoul (KR); Bo Hyun Nam, Seoul (KR); Seung Hyun Song, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 94 days.

(21) Appl. No.: 18/720,980

(22) PCT Filed: Dec. 5, 2022

(86) PCT No.: PCT/KR2022/019622
§ 371 (c)(1),
(2) Date: Jun. 17, 2024

(87) PCT Pub. No.: WO2023/113348
PCT Pub. Date: Jun. 22, 2023

(65) Prior Publication Data
US 2025/0057389 A1 Feb. 20, 2025

(30) Foreign Application Priority Data
Dec. 17, 2021 (KR) ........................ 10-2021-0181928

(51) Int. Cl.

| | |
|---|---|
| ***A47L 23/02*** | (2006.01) |
| ***A47L 23/20*** | (2006.01) |
| ***A61L 2/07*** | (2006.01) |
| *D06F 58/10* | (2006.01) |

(52) U.S. Cl.
CPC ............... *A47L 23/02* (2013.01); *A47L 23/20* (2013.01); *A47L 23/205* (2013.01); *A61L 2/07* (2013.01); *D06F 58/10* (2013.01)

(58) Field of Classification Search
CPC ........ A47L 23/02; A47L 23/20; A47L 23/205; A47B 61/04; A61L 2/07; D06F 58/10
See application file for complete search history.

(56) References Cited

U.S. PATENT DOCUMENTS

2021/0401262 A1* 12/2021 Yoo ......................... B08B 15/04
2021/0401266 A1* 12/2021 Yoo ......................... F25B 21/02
2021/0402029 A1* 12/2021 Yoo ........................... A61L 2/24
2022/0192464 A1* 6/2022 Jung ..................... A47L 23/205
2022/0192465 A1* 6/2022 Lee ........................... A61L 2/07
2022/0313061 A1* 10/2022 Kim ........................ A47L 23/18
(Continued)

FOREIGN PATENT DOCUMENTS

JP 9-108495 A 4/1997
JP 2020-199239 A 12/2020
KR 10-2000-0009653 A 2/2000
(Continued)

*Primary Examiner* — Joseph L. Perrin
(74) *Attorney, Agent, or Firm* — Birch, Stewart, Kolasch & Birch, LLP

(57) ABSTRACT

A shoe care apparatus includes an inner cabinet, a door, a connecting flow path, a blower unit, a dehumidifying unit, a steam generator, and a steam inlet. The steam inlet forms an entrance through which the steam flows into an accommodation space of the inner cabinet. The door is located at the front portion of the inner cabinet, and the steam inlet is located at the center of the rear side of the accommodation space.

19 Claims, 32 Drawing Sheets

(56) References Cited

U.S. PATENT DOCUMENTS

| | | | | |
|---|---|---|---|---|
| 2022/0313862 | A1* | 10/2022 | Lee | A43D 3/14 |
| 2022/0338711 | A1* | 10/2022 | Jeong | F26B 21/02 |

FOREIGN PATENT DOCUMENTS

| | | | |
|---|---|---|---|
| KR | 10-1037245 | B1 | 5/2011 |
| KR | 10-2020-0039396 | A | 4/2020 |
| KR | 10-2021-0030856 | A | 3/2021 |
| KR | 10-2021-0085188 | A | 7/2021 |

* cited by examiner

【FIG. 1a】
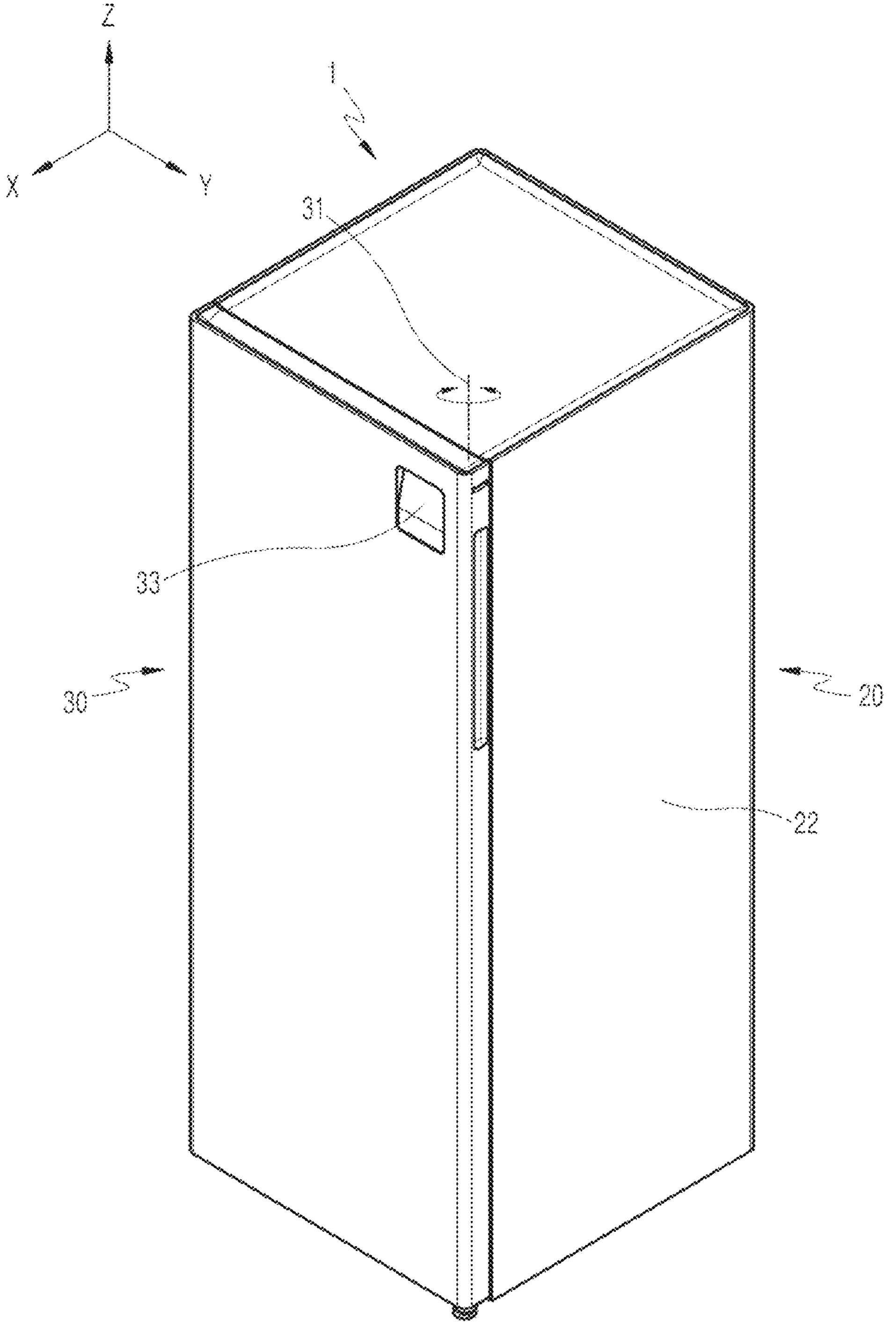

【FIG. 1b】
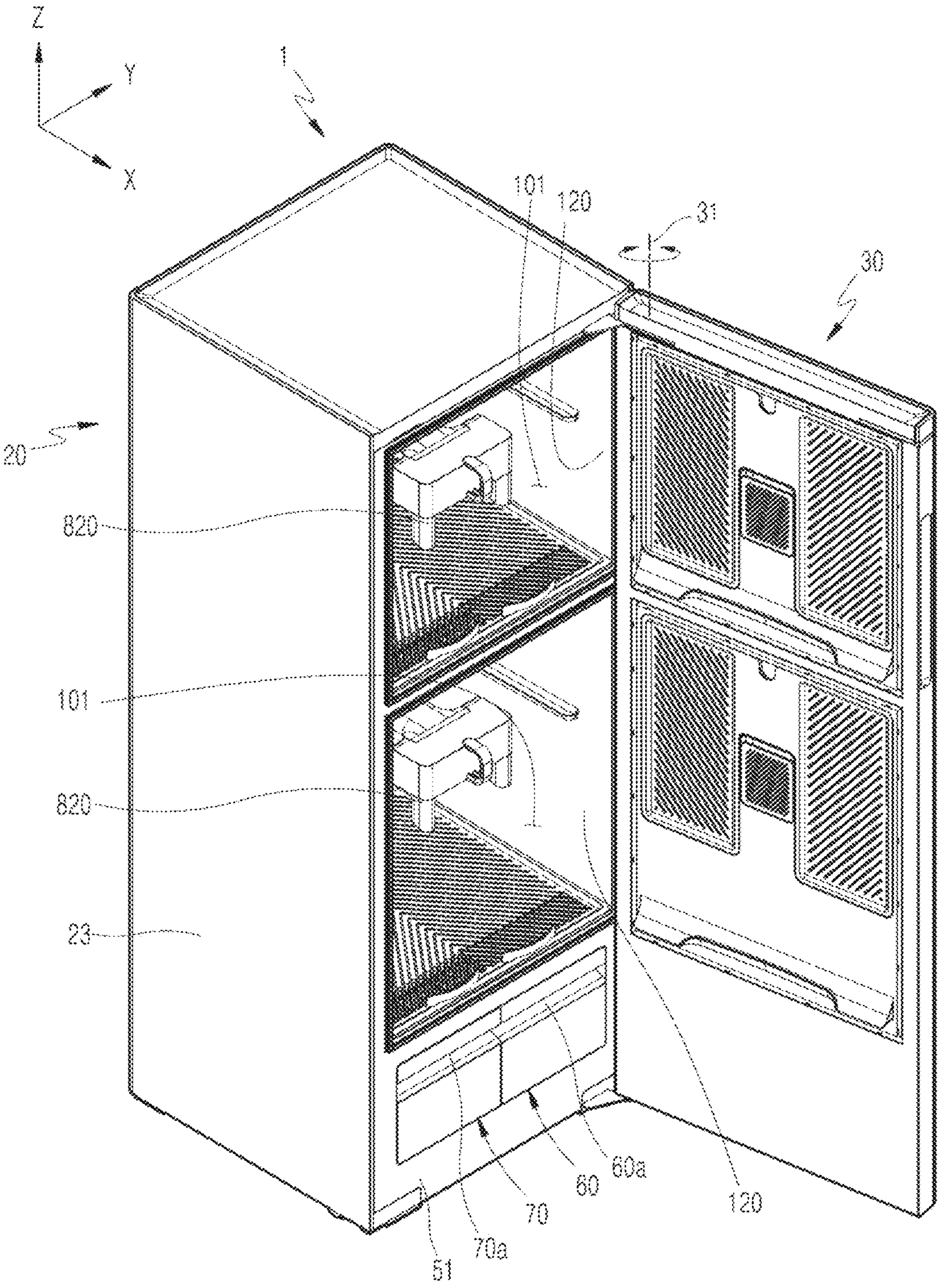

【FIG. 2a】
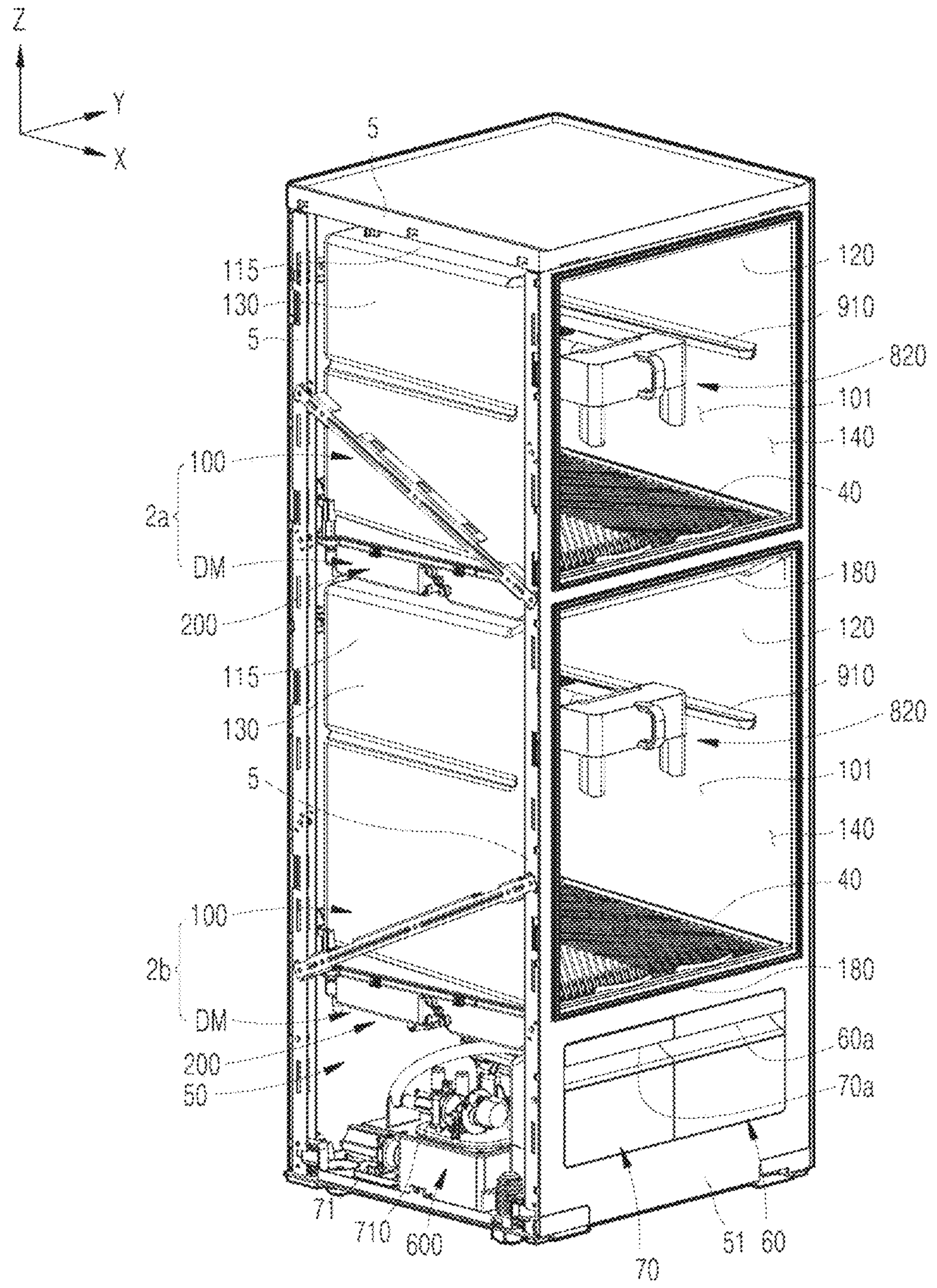

【FIG. 2b】
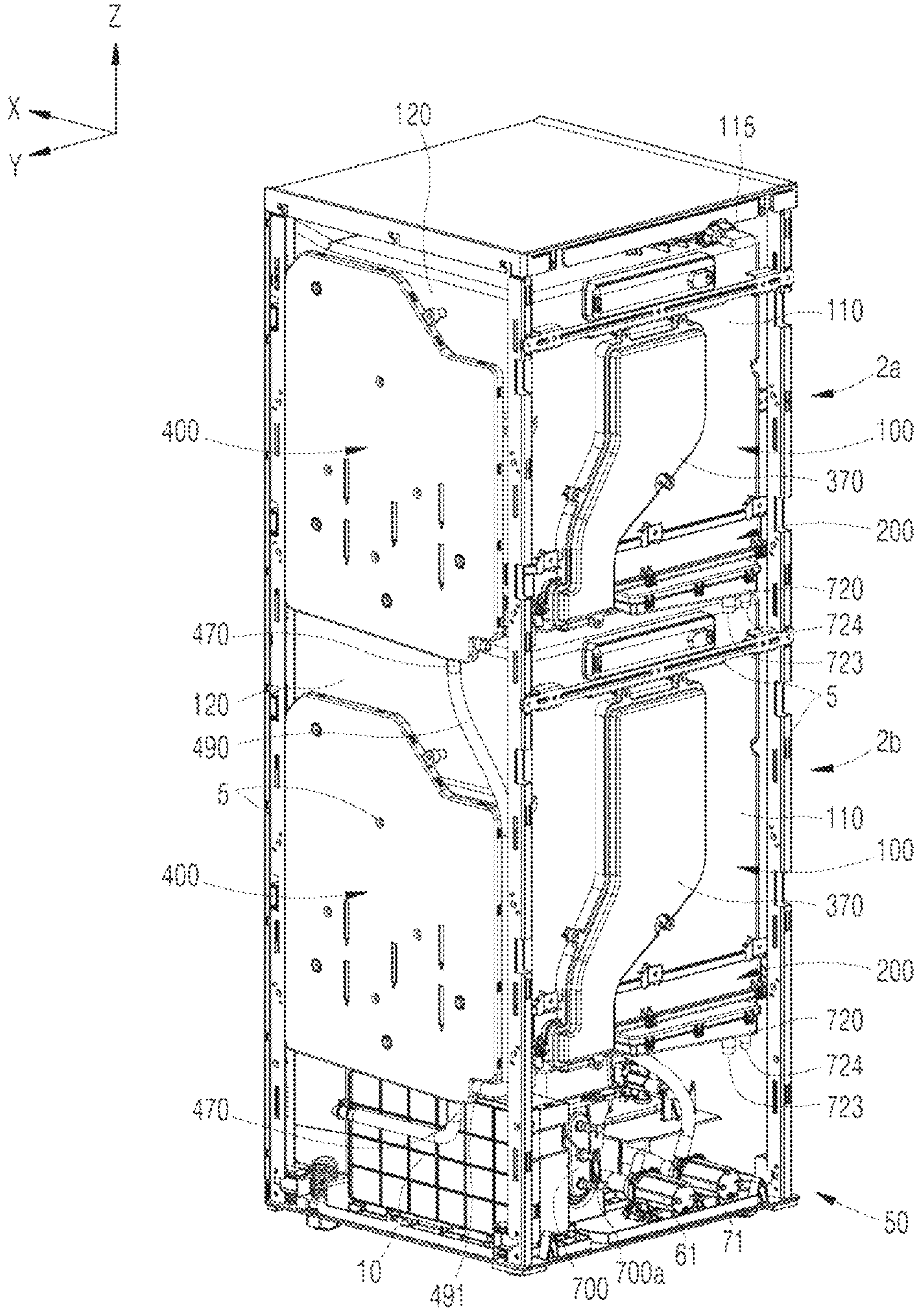

【FIG. 4a】
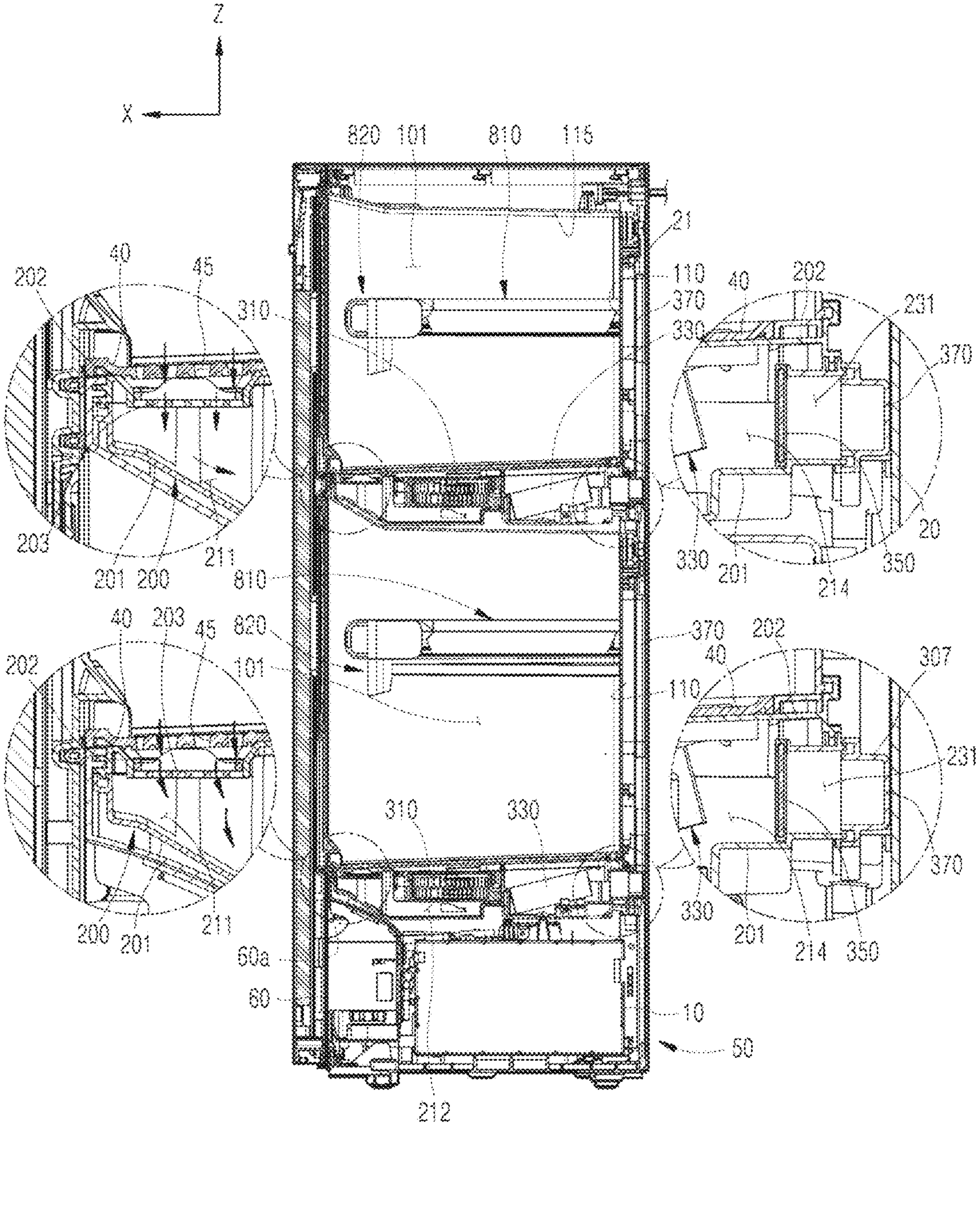

【FIG. 4b】
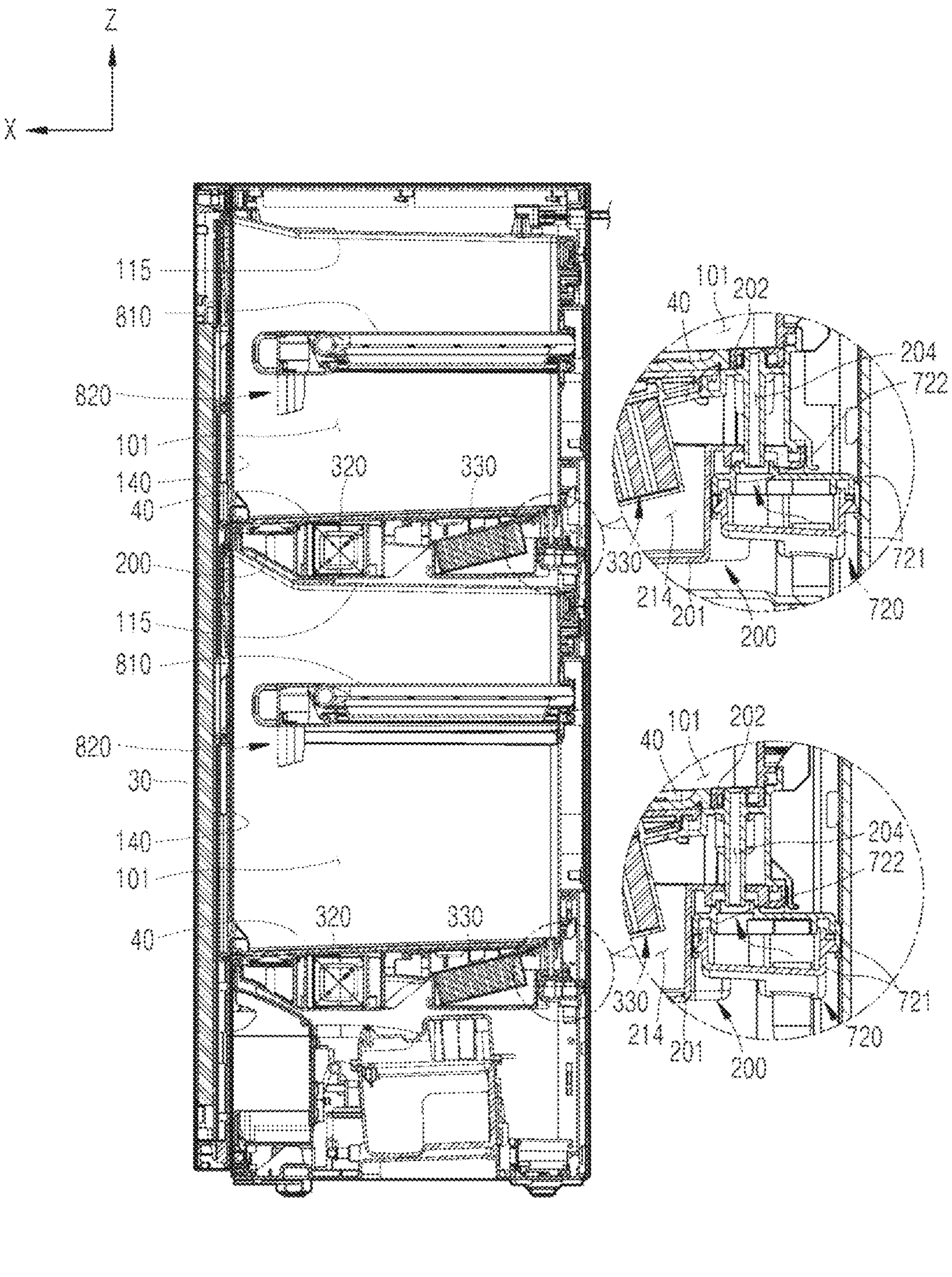

【FIG. 4c】
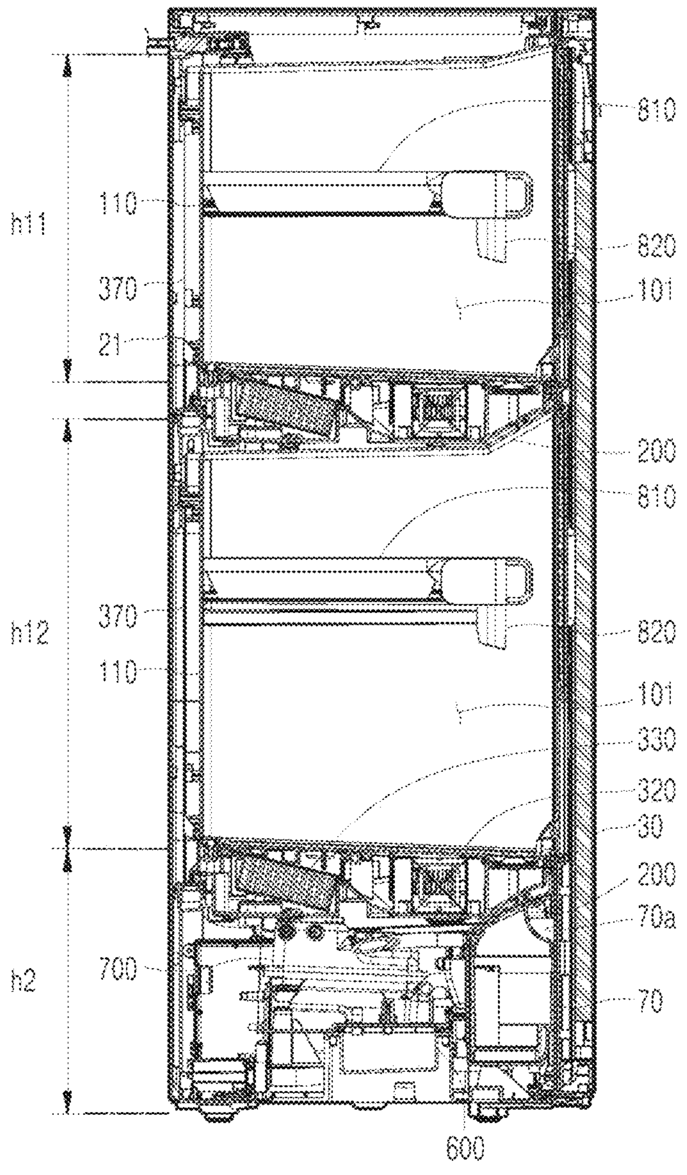

【FIG. 5】
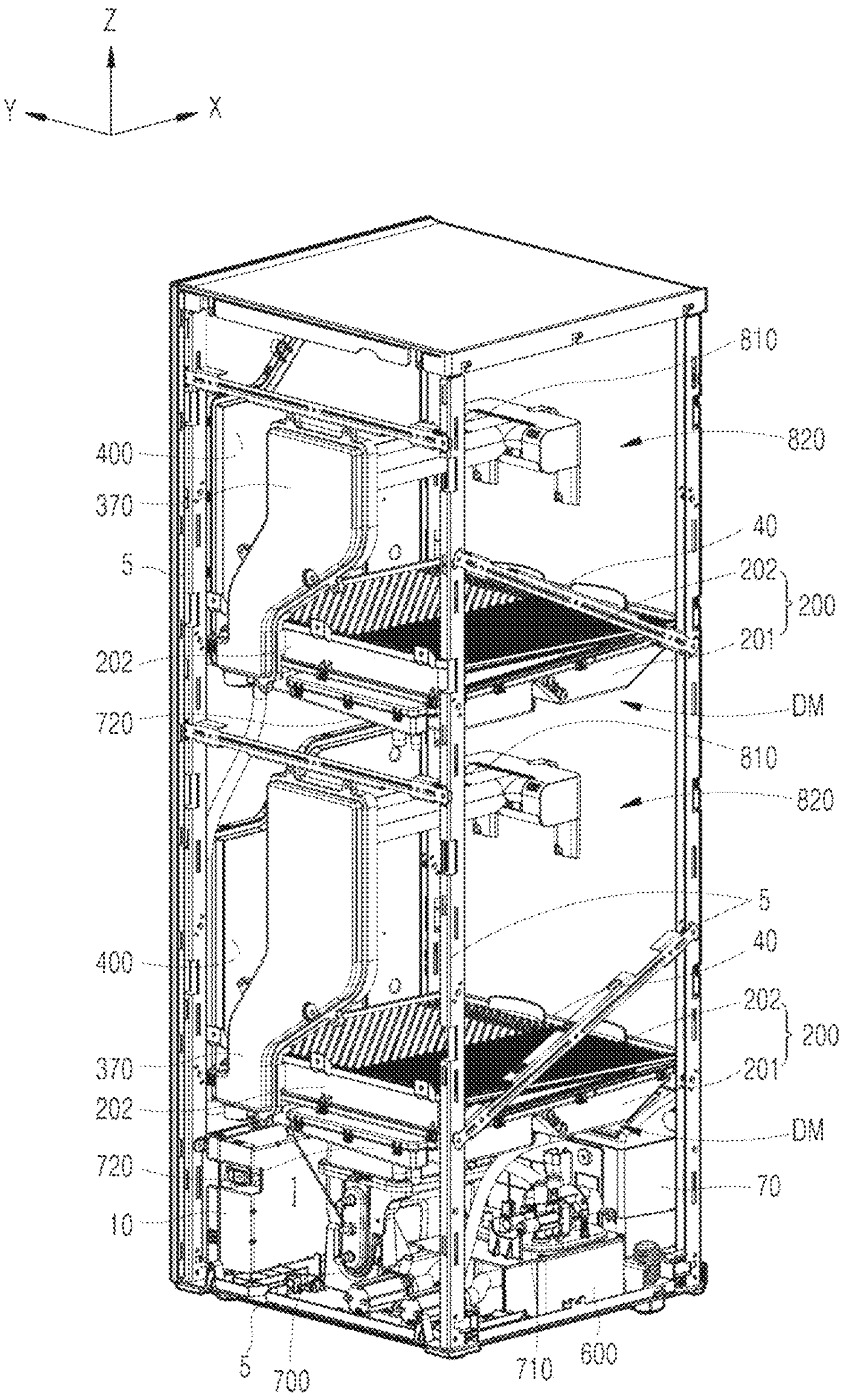

【FIG. 6】
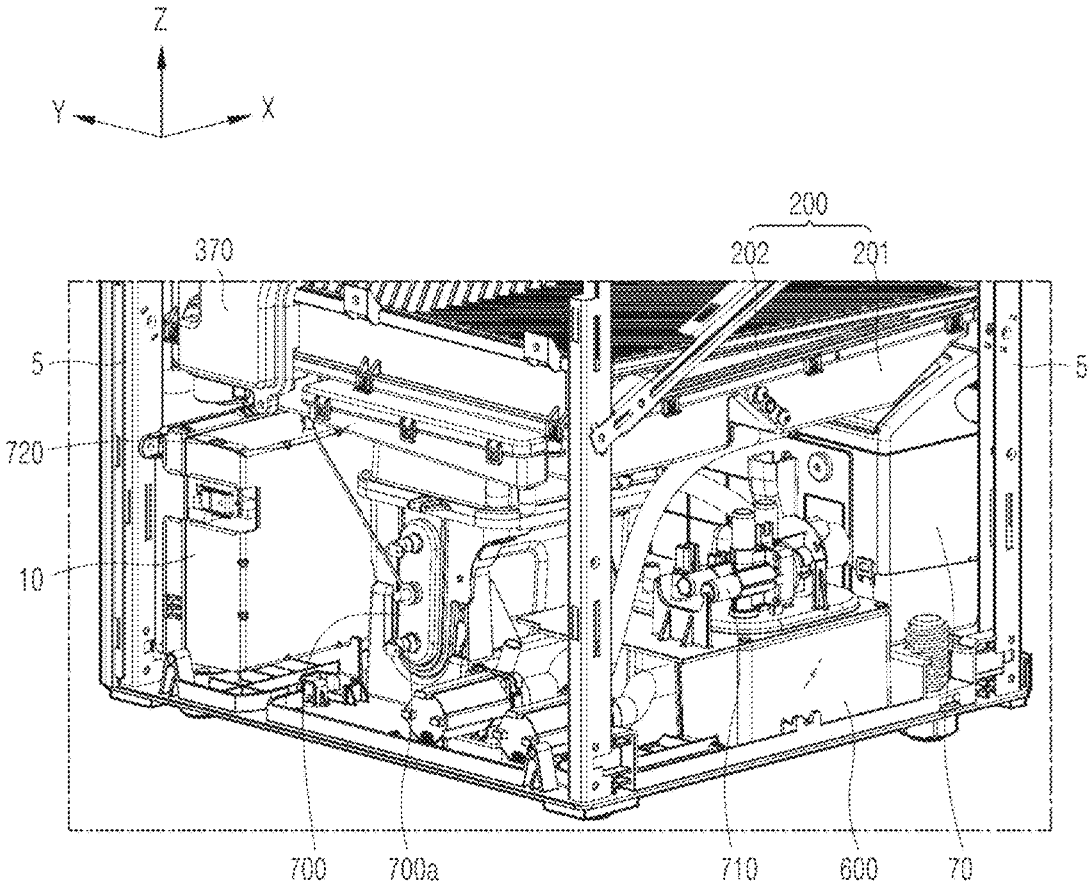

【FIG. 7a】
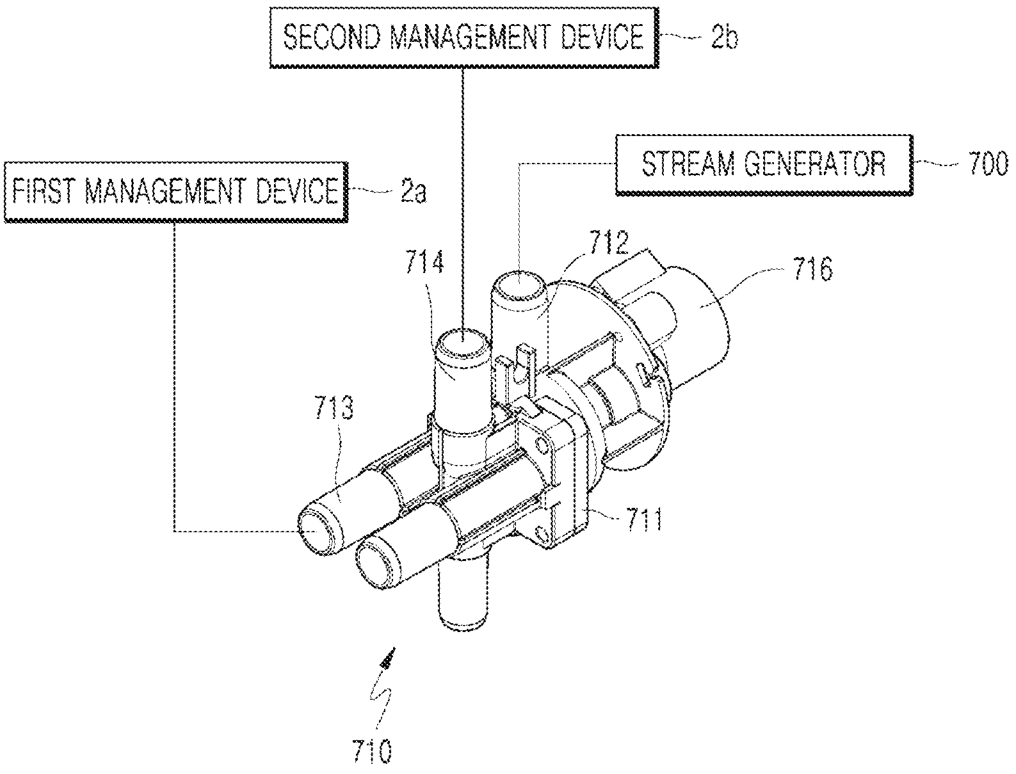
【FIG. 7b】
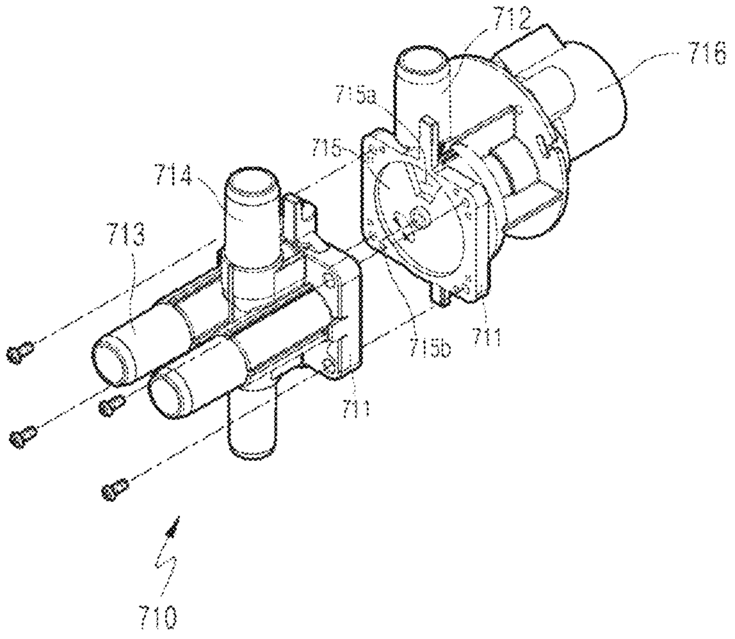

【FIG. 8a】
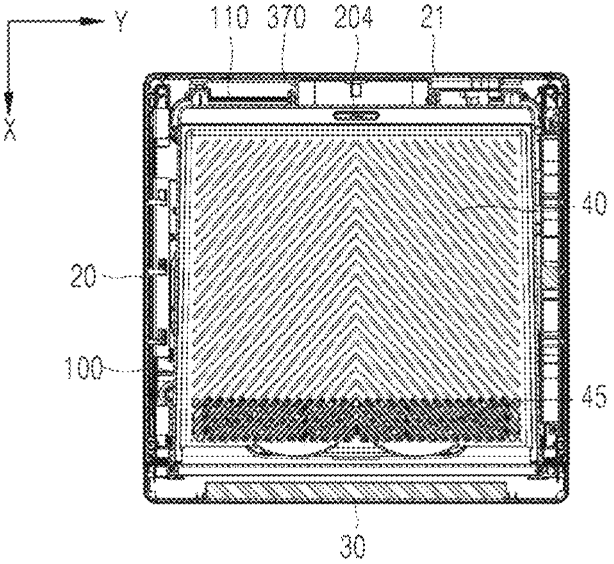
【FIG. 8b】
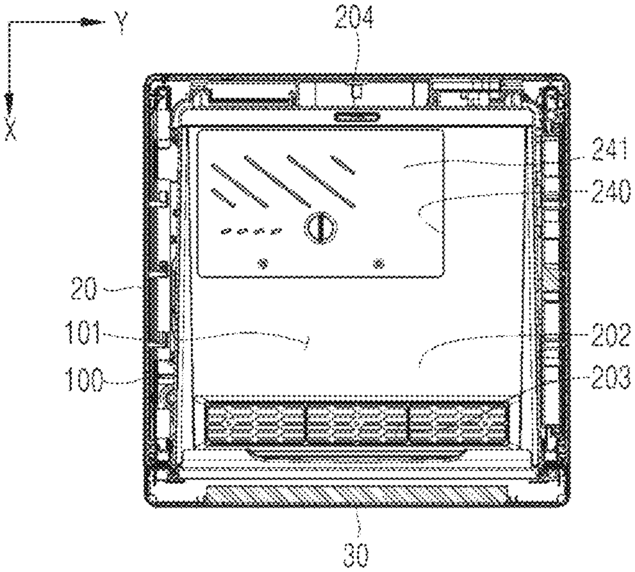

【FIG. 9】
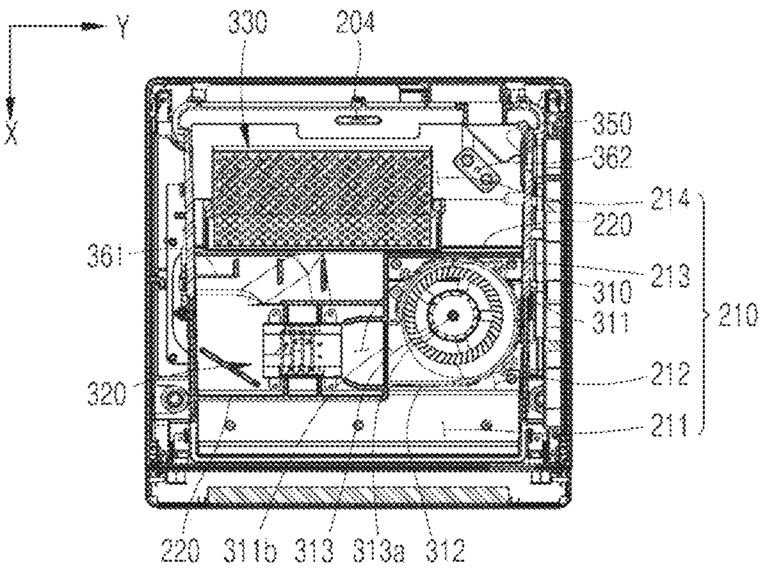

【FIG. 12a】
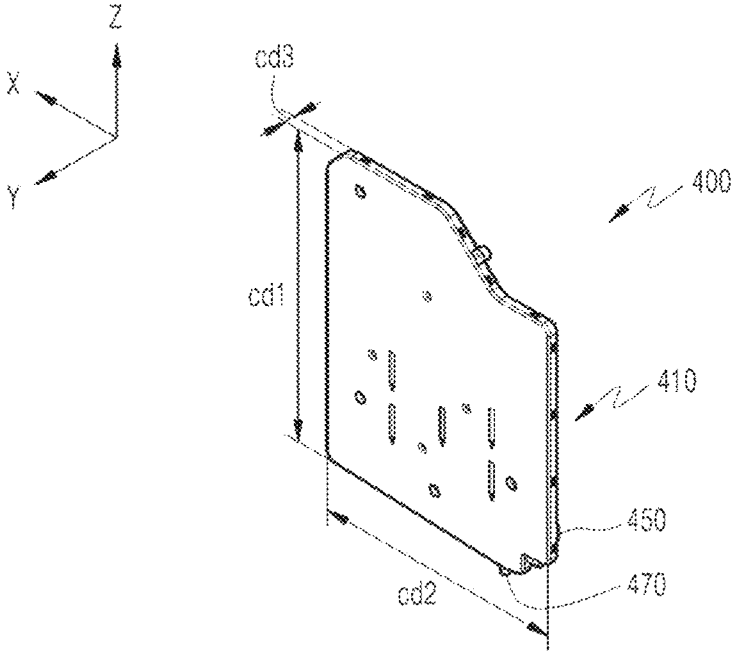
【FIG. 12b】
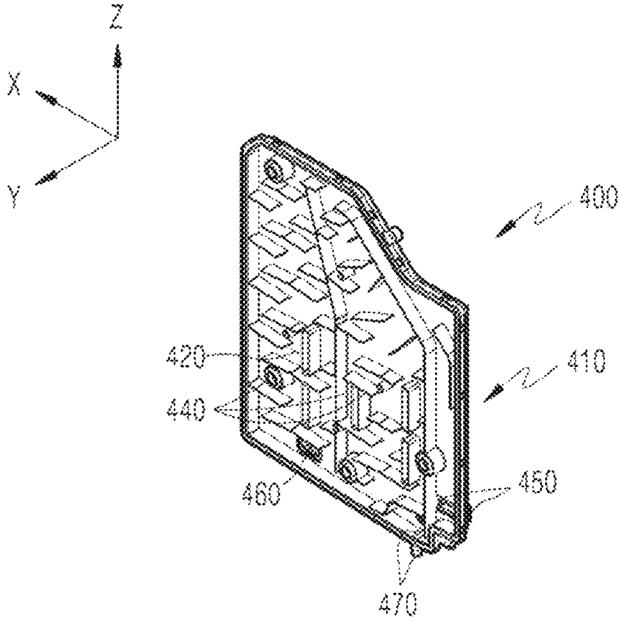

【FIG. 12c】
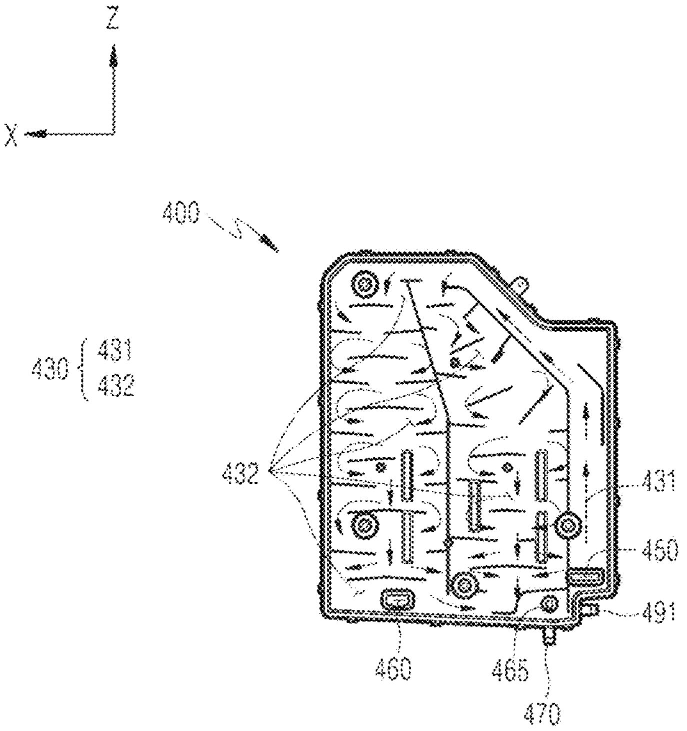
【FIG. 13】
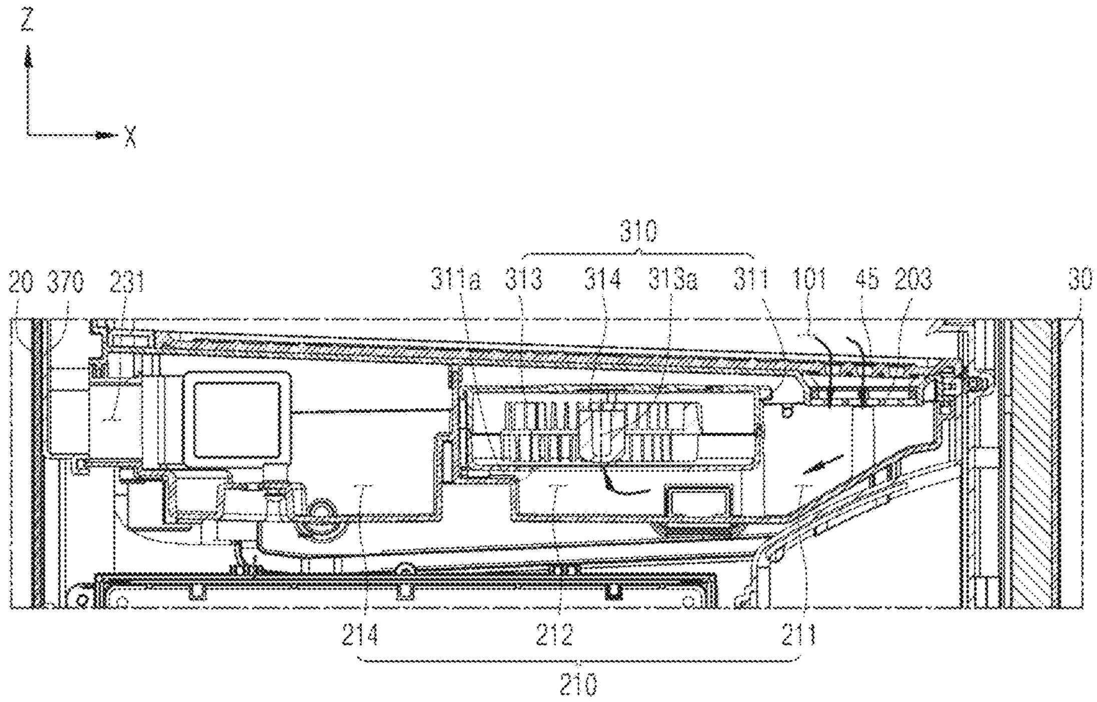

【FIG. 14】
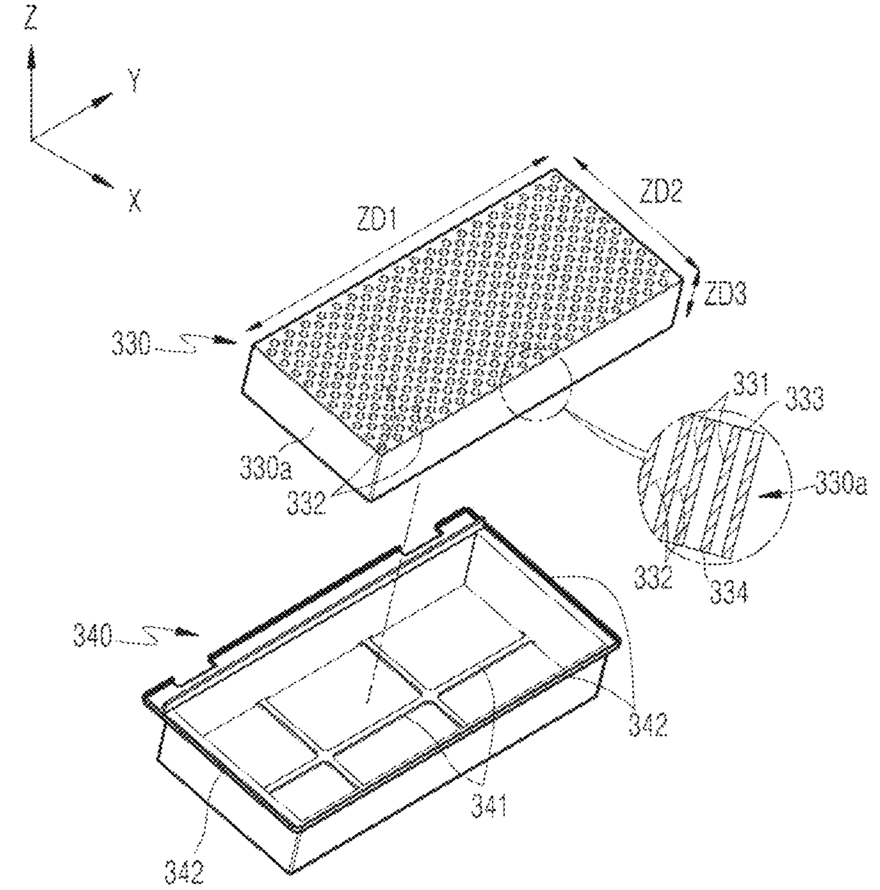
【FIG. 15】
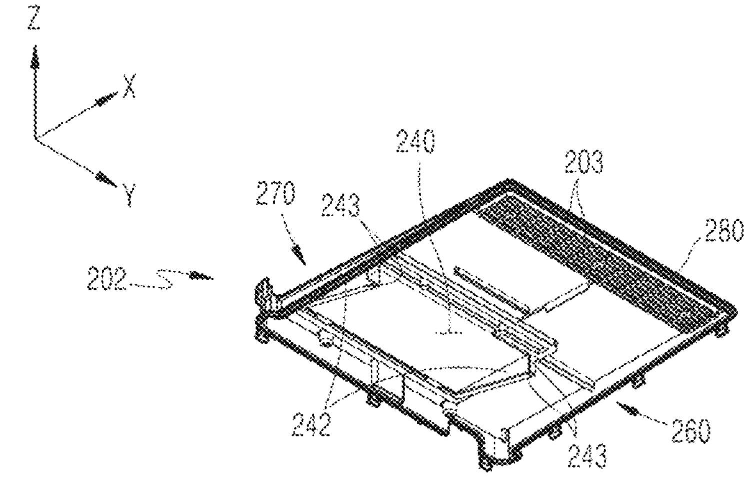

【FIG. 16】
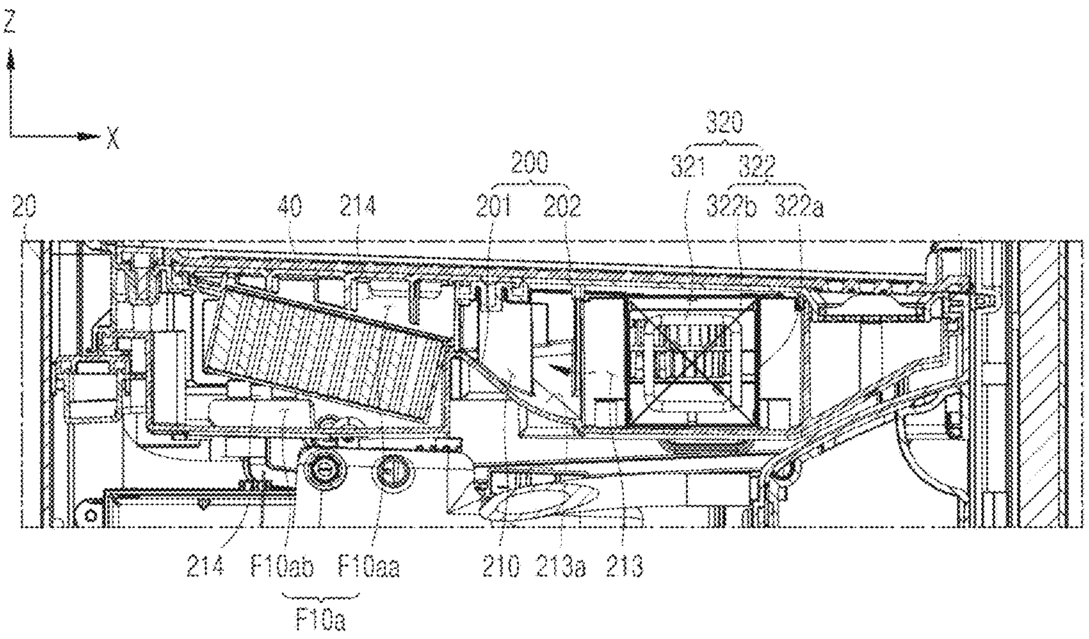
【FIG. 17】
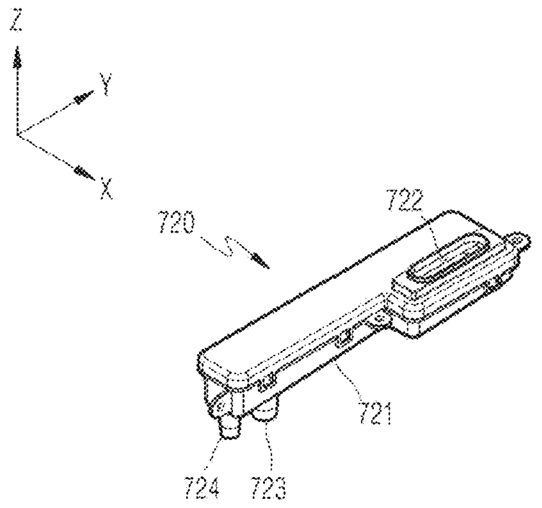

【FIG. 18a】
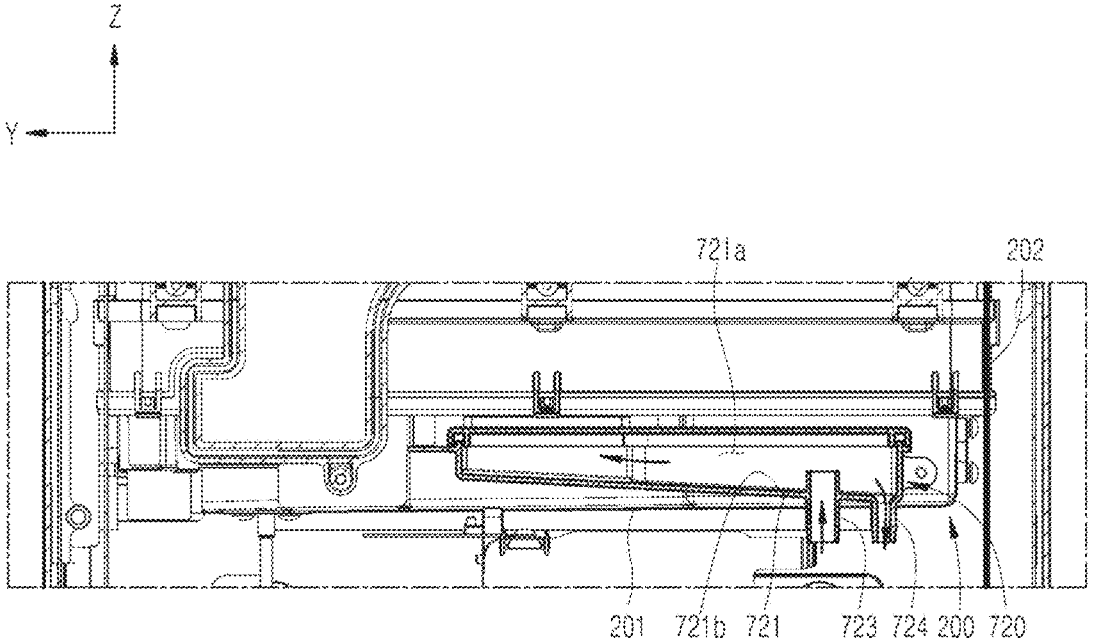
【FIG. 18b】
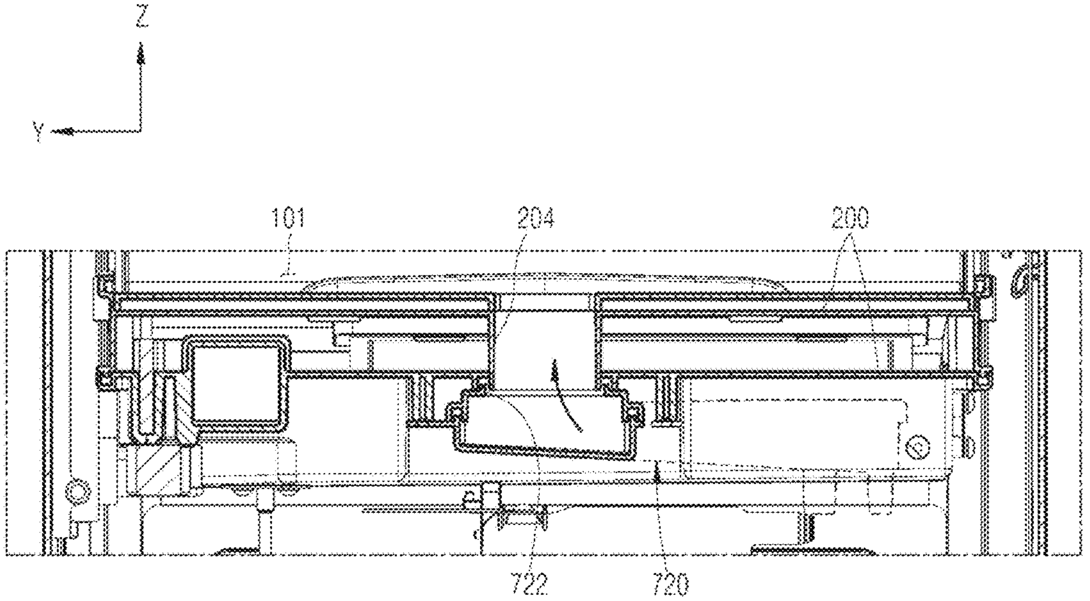

【FIG. 19a】
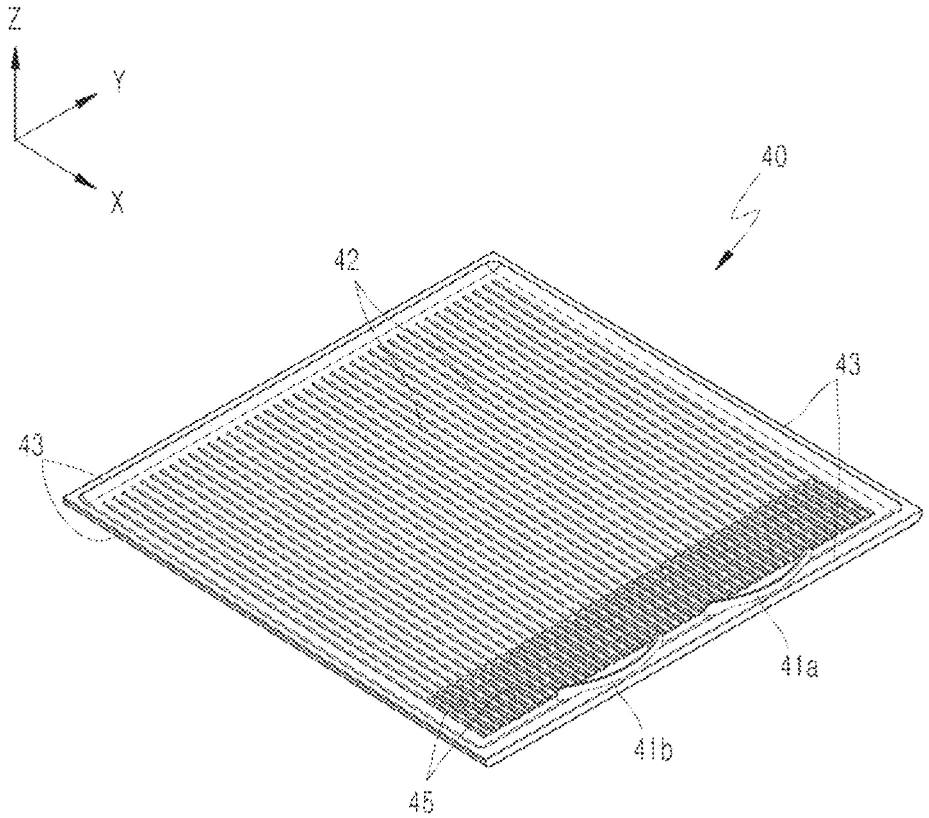

【FIG. 19b】
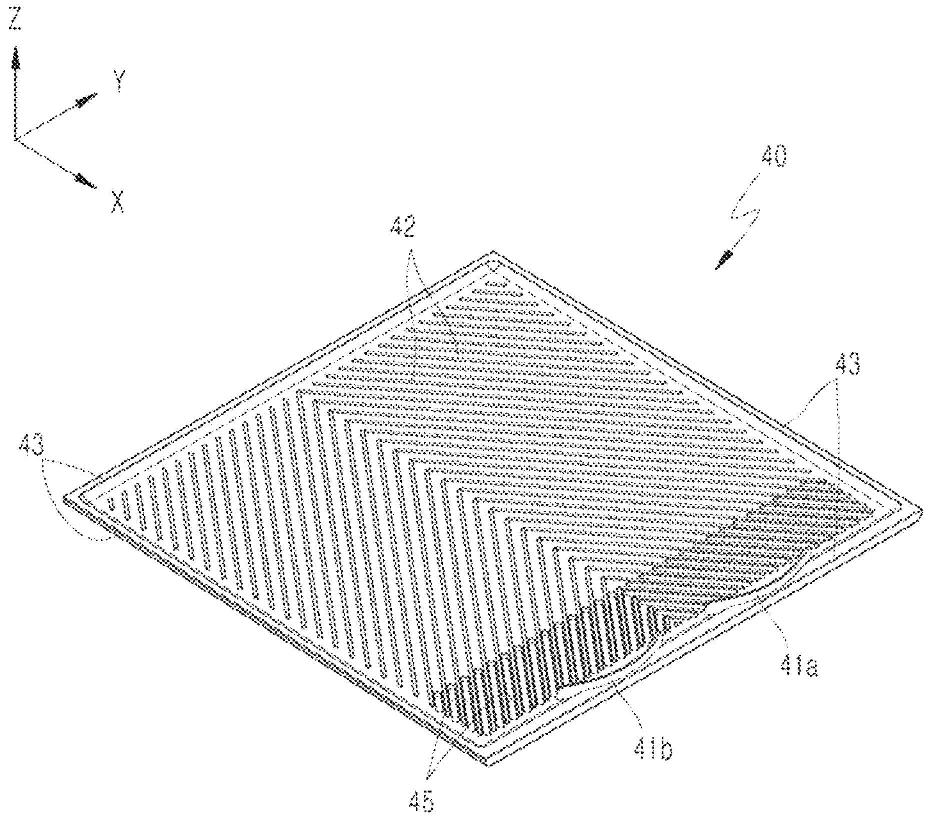

【FIG. 20】
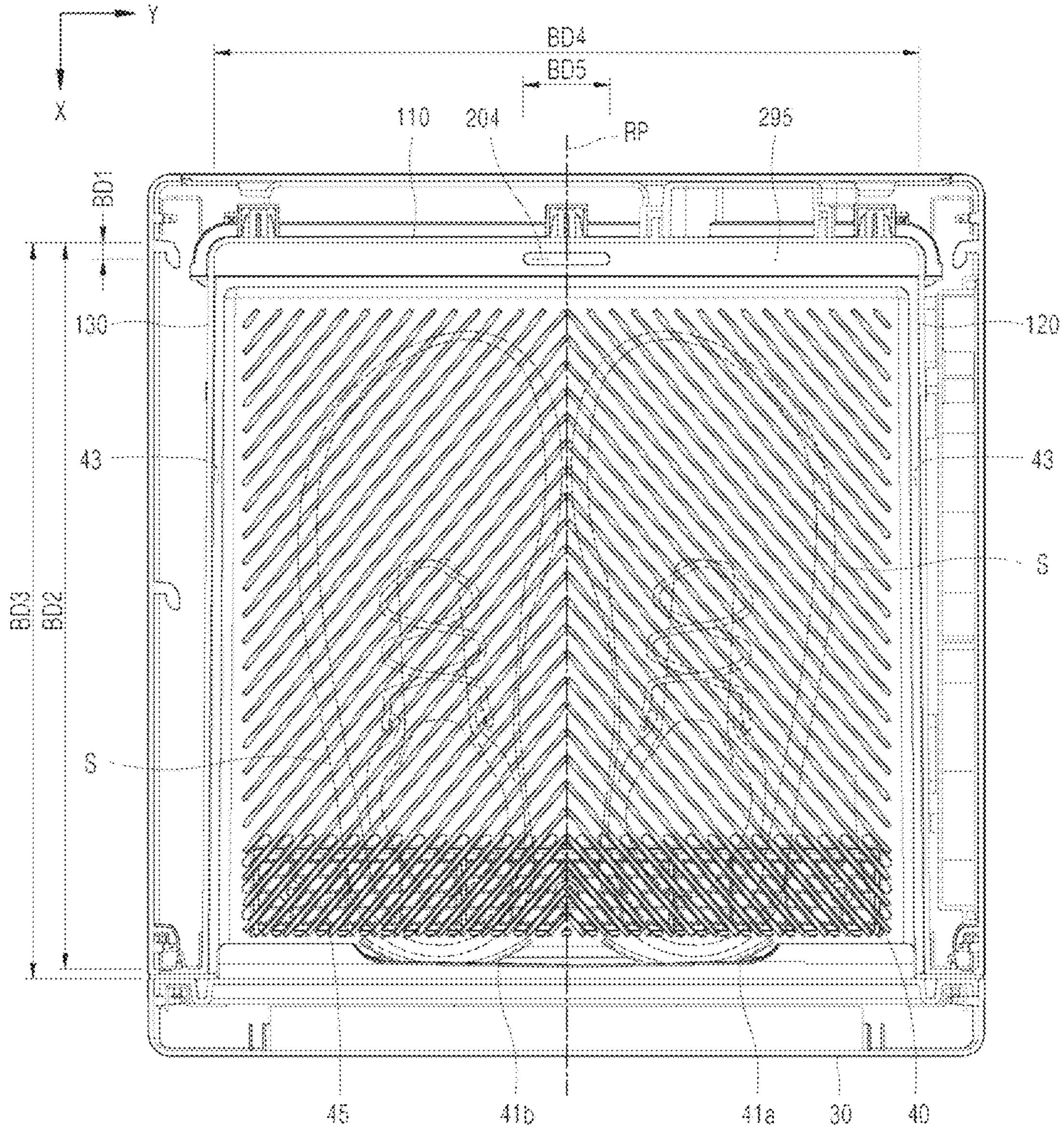

【FIG. 21】
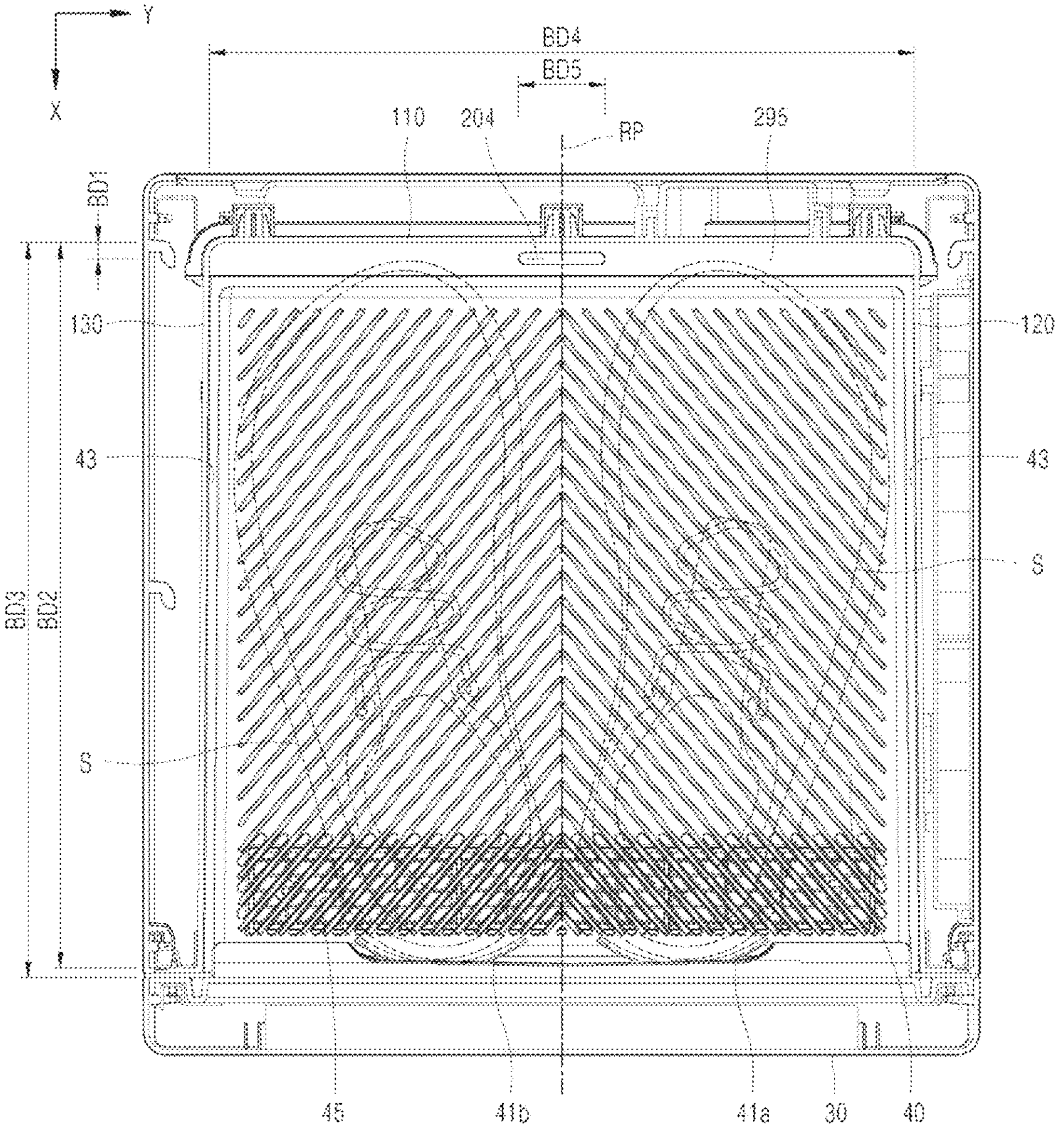

【FIG. 22】
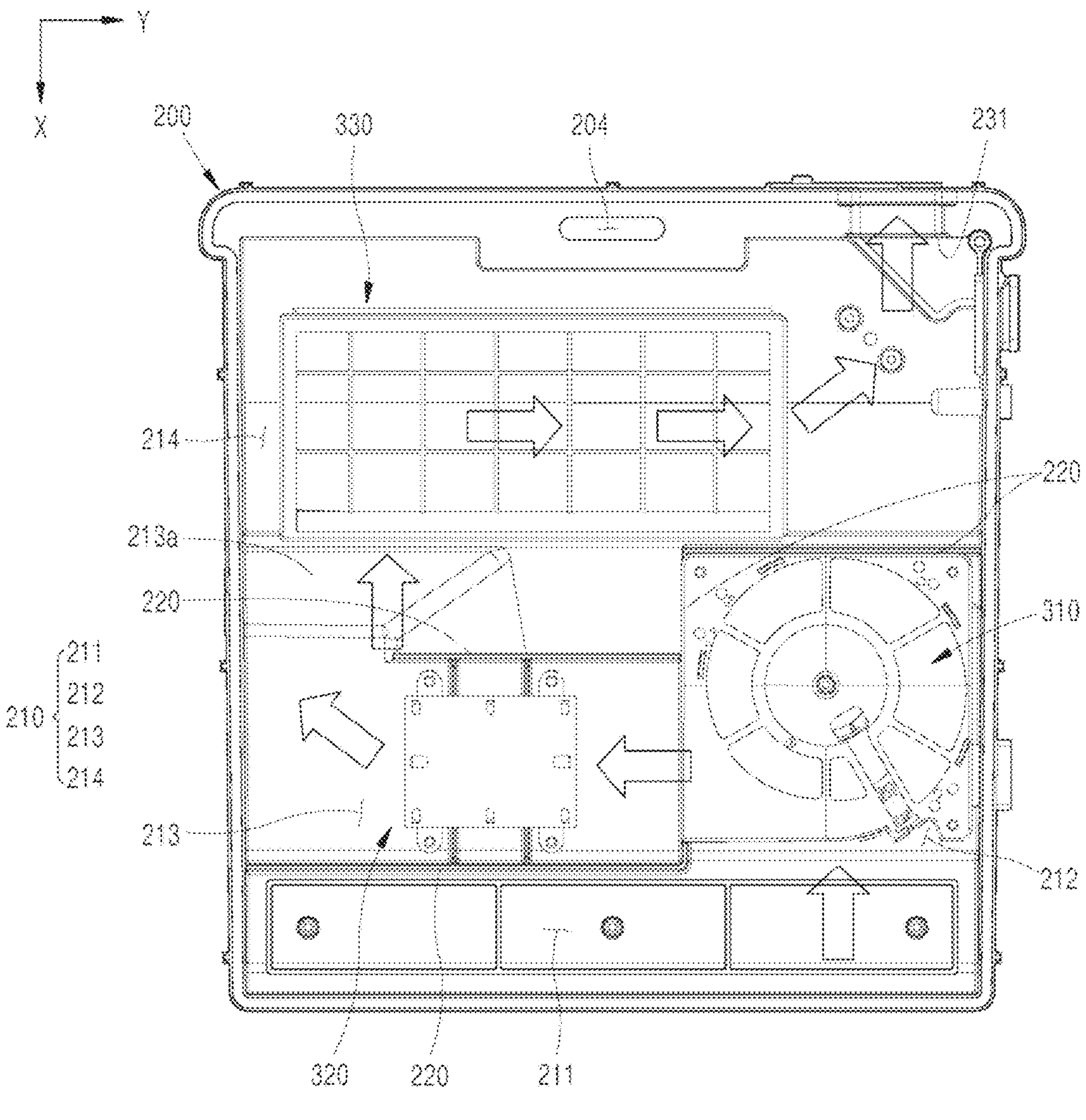

【FIG. 23】
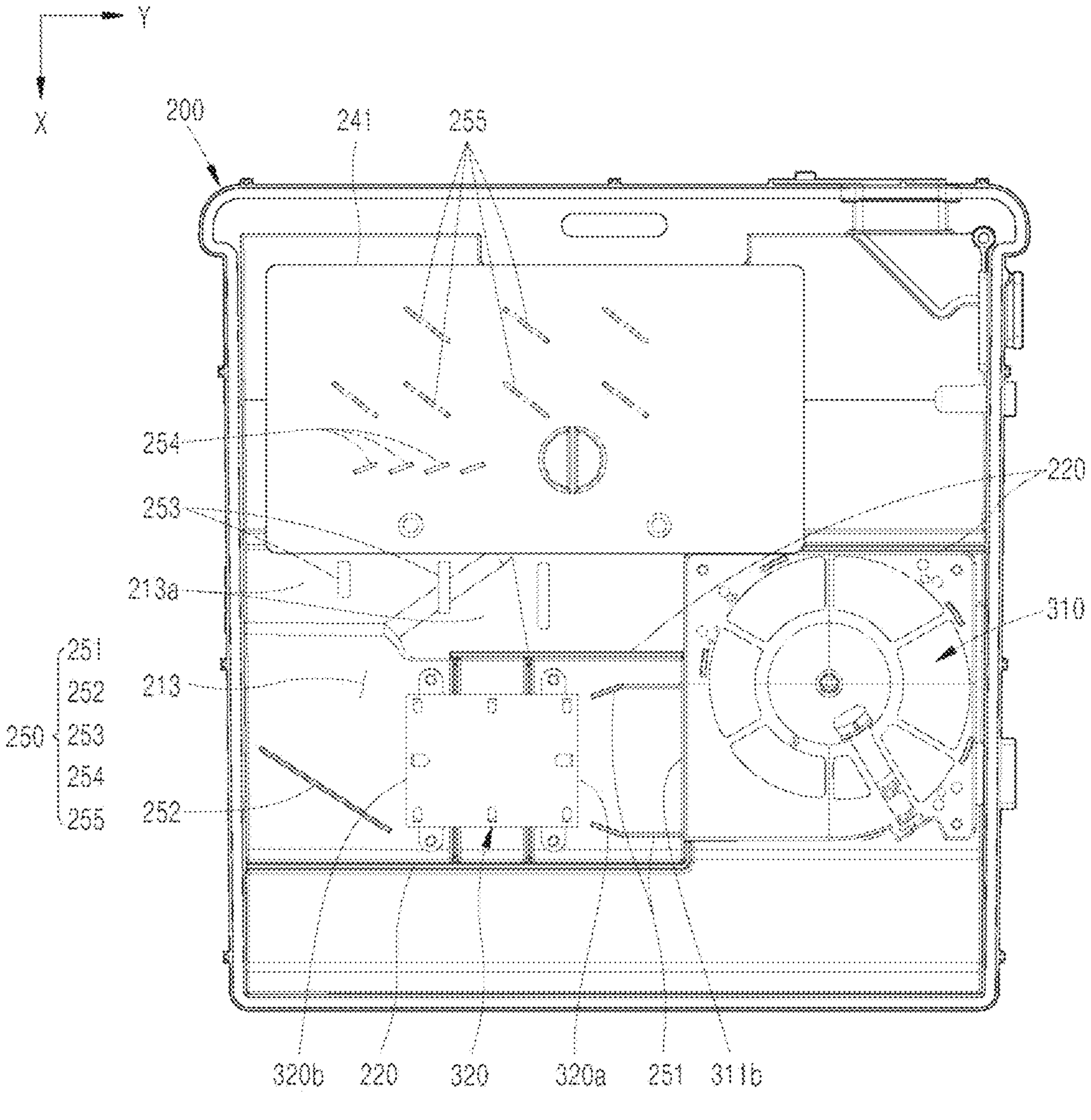

【FIG. 24】
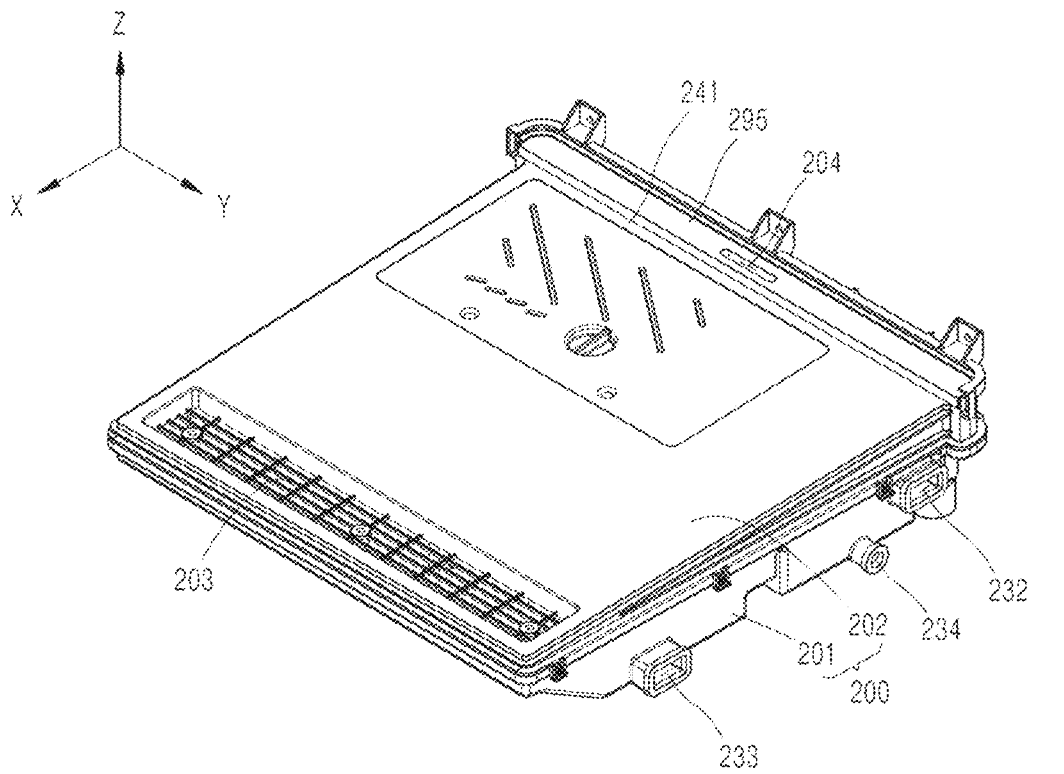
【FIG. 25】
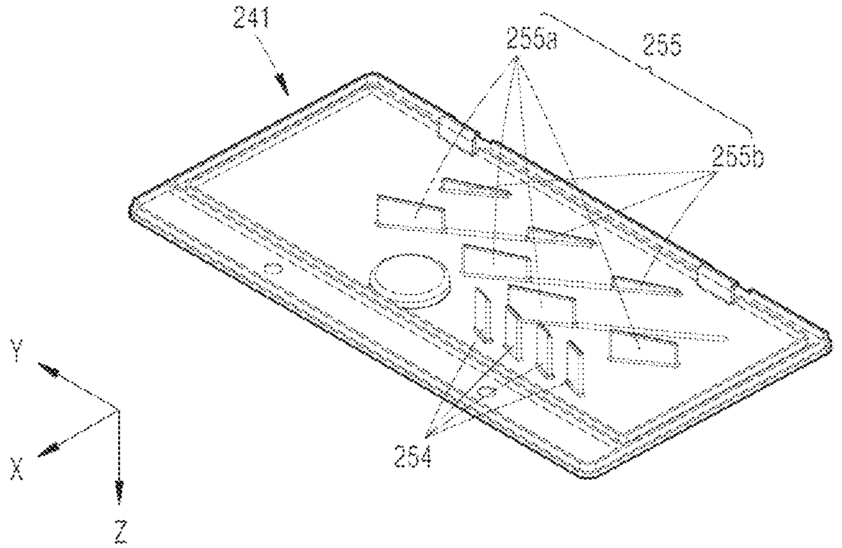

【FIG. 26】
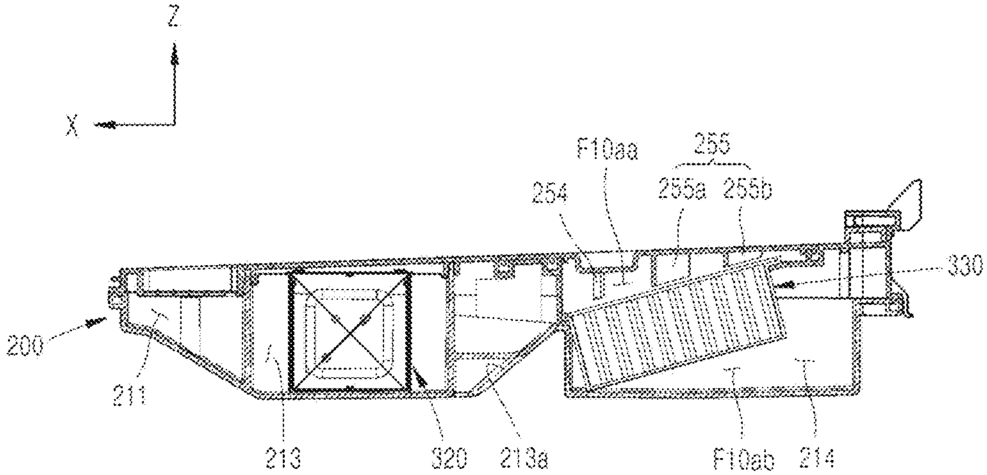
【FIG. 27a】
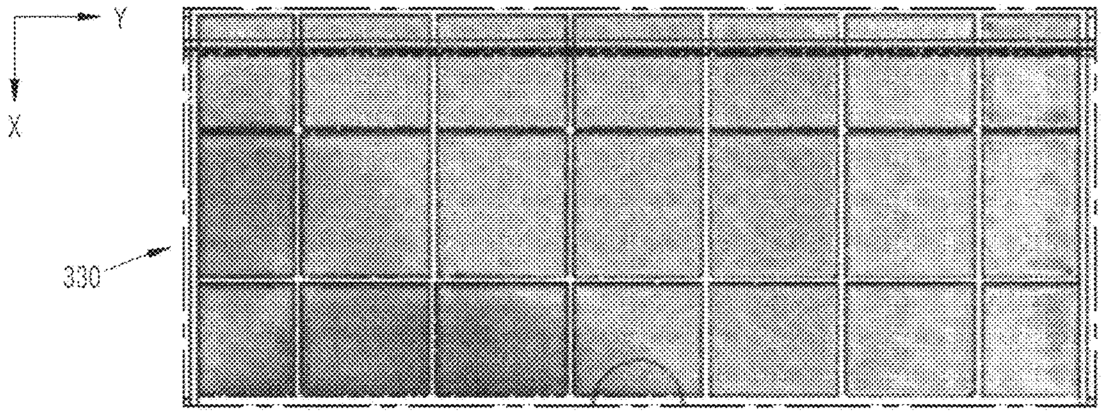

【FIG. 27b】
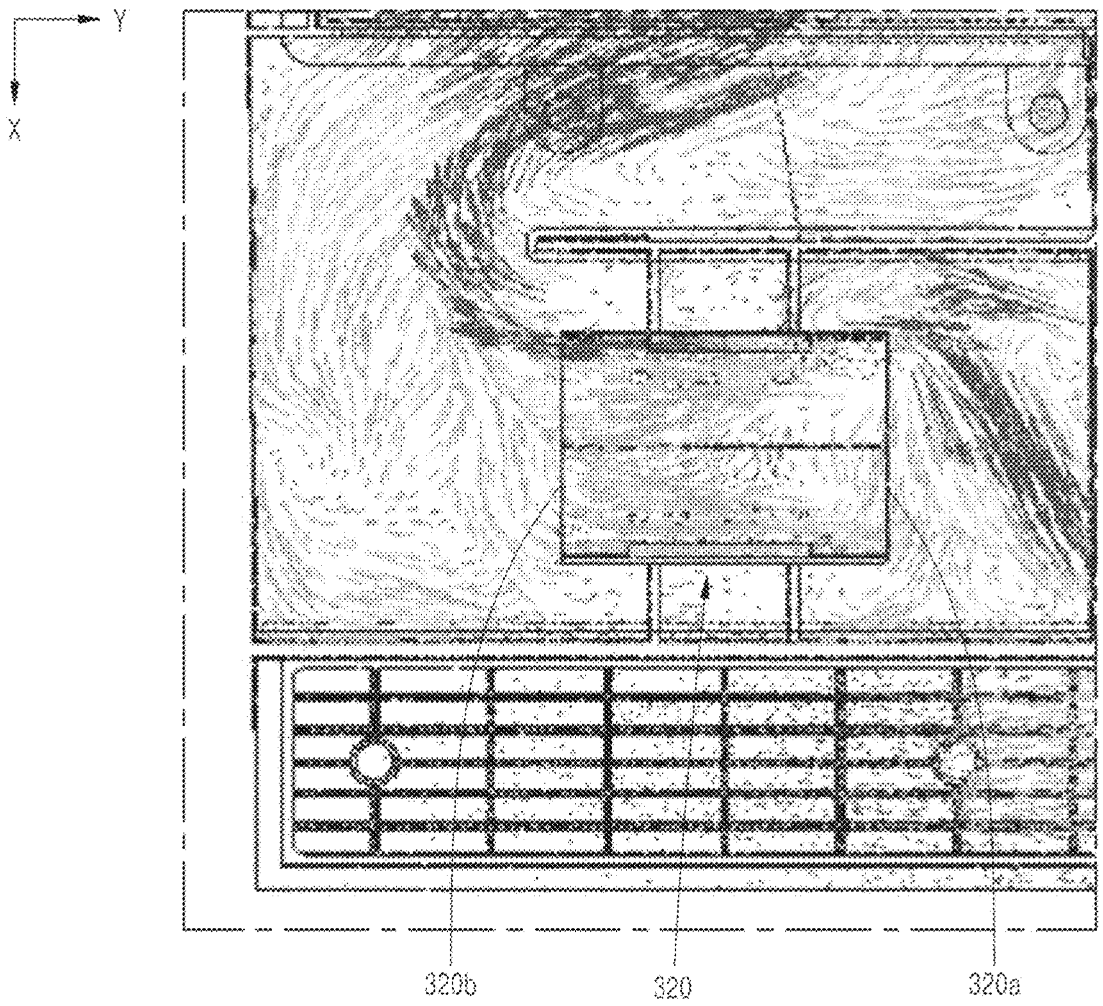

【FIG. 28a】
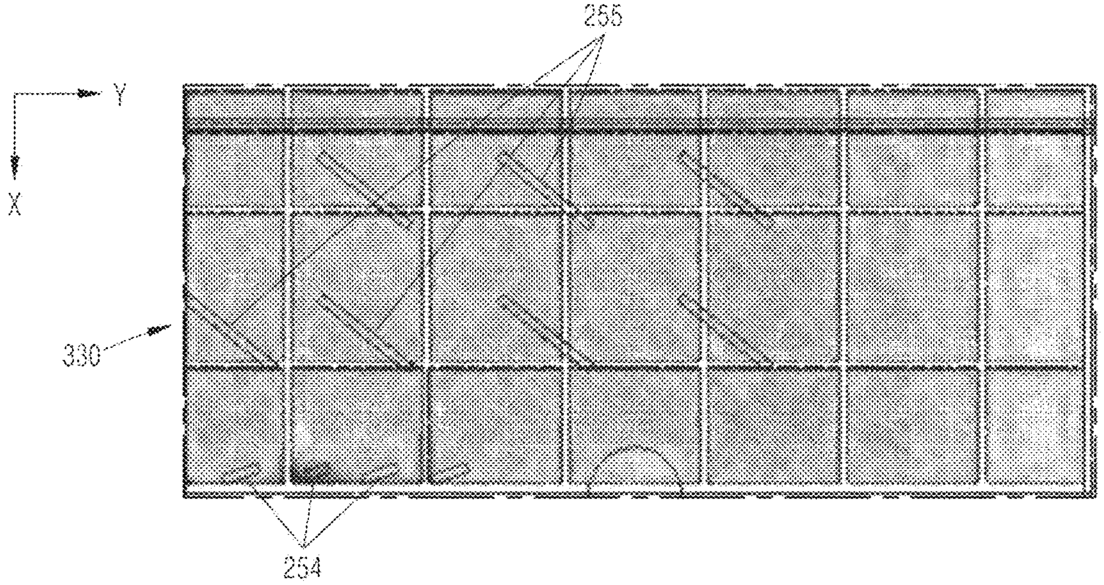

【FIG. 28b】
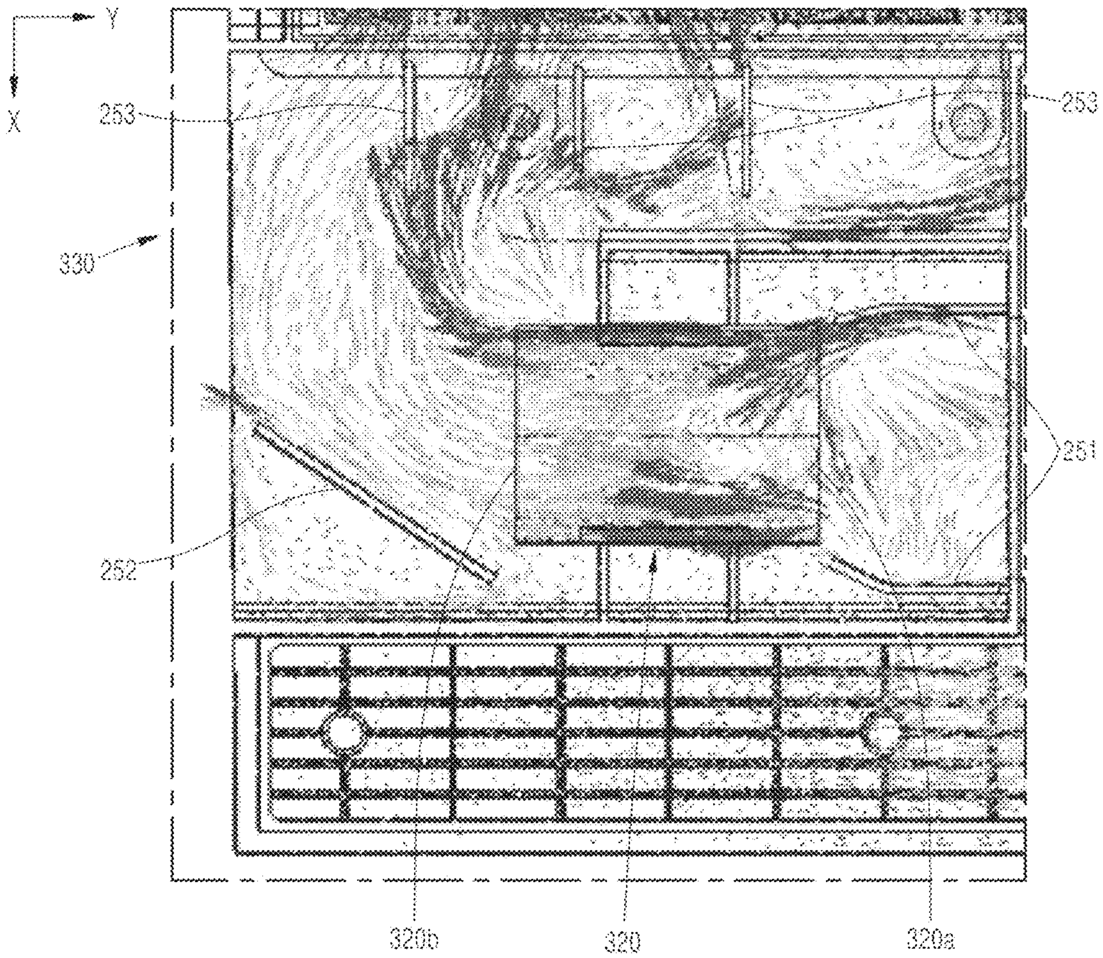
【FIG. 29a】
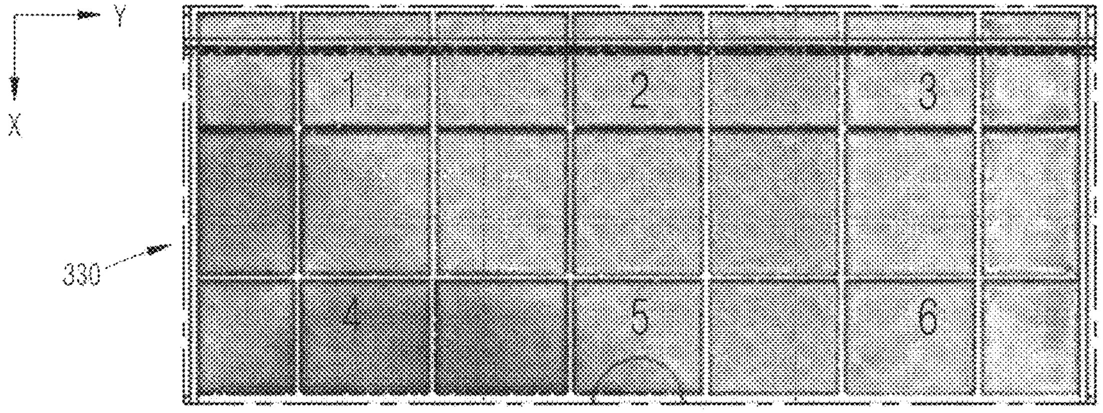

【FIG. 29b】
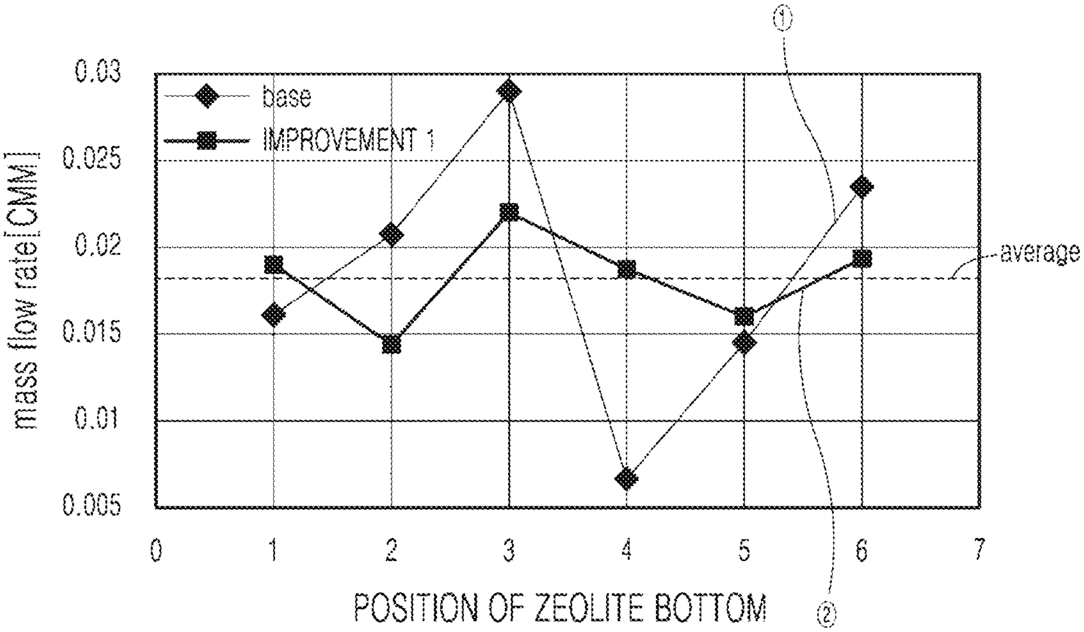

SHOE CARE APPARATUS

CROSS-REFERENCE TO RELATED APPLICATIONS

This application is the National Phase of PCT International Application No. PCT/KR2022/019622, filed on Dec. 5, 2022, which claims priority under 35 U.S.C. 119(a) to Patent Application No. 10-2021-0181928, filed in the Republic of Korea on Dec. 17, 2021, all of which are hereby expressly incorporated by reference into the present application.

TECHNICAL FIELD

The present invention relates to a shoes care device, and more particularly, to a shoes care device which treats shoes by air circulation.

BACKGROUND ART

Shoes may get wet by a wearer's sweat, external contaminants, or rain or snow. Wearing such shoes may make the wearer uncomfortable, and in this condition, germs may also breed or the shoes may stink.

Accordingly, there is an increasing interest in a shoes care device, which removes germs and odors by performing a predetermined treatment on the shoes so that a user can comfortably wear the shoes all the time.

For the shoes care device, Korean Patent No. 10-1037245 (hereinafter, referred to as "Prior Art Document 1"), entitled "Apparatus for sterilization disposal of shoes", includes a main body, an ultraviolet emission module, and a deodorization module.

According to Prior Art Document 1 above, the shoes are disposed in a sterilization chamber of the main body, and the ultraviolet emission module is driven to remove germs and odors of the shoes. Furthermore, the air in the sterilization chamber is sucked into a ventilation pipe and discharged to the outside of the main body through an exhaust port through the deodorization module.

Here, the deodorization module includes a deodorization column made up of materials such as zeolite, activated carbon, and charcoal, and removes contaminants from the air discharged from the inside of the main body to the outside by the deodorization column.

According to Prior Art Document 1 above, the air from which moisture has been removed by a deodorization module including zeolite and activated carbon can be discharged to the outside of the apparatus for sterilization disposal of shoes.

However, in Prior Art Document 1 above, since the air is discharged to the outside of the apparatus for sterilization of shoes, the air that has not sufficiently removed moisture or odors may be discharged to the outside of the apparatus for sterilization disposal of shoes, and such air may be discharged to the inside where the wearer resides.

In addition, Korean Patent Unexamined Publication No. 10-2000-0009653 (hereinafter referred to as "Prior Art Document 2"), entitled "The shoes cabinet for sanitation", which discloses a shoe closet that includes a main body, a far infrared radiation part, a circulation fan, an air circulation passage, and a sanitary filter portion.

According to Prior Art Document 2 above, while storing shoes in shoe closet, hygiene treatments such as dehumidification, sterilization, and deodorization can be performed on the shoes by far-infrared rays and a filter during the storing of the shoes.

Here, since the sanitary filter portion is filled with excellent adsorptive materials such as charcoal, it can serve to adsorb moisture in the process of ventilating air and filter bacteria, as well as to capture malodorous substances.

According to Prior Art Document 2 above, the air is circulated by a circulating fan in a shoe closet, and the sanitary filter portion is disposed on a circulation path of the air to remove germs and odors in the air.

However, since Prior Art Document 2 above does not consider a technology to prevent the reduction of the performance of the sanitary filter portion configured to remove moisture or odors, a user may not be satisfied because the shoes are not properly treated at the time of using a shoes care device.

As described above, for the shoes care device that removes germs or odors by treating the shoes in a predetermined manner, a task that has to be solved to ensure proper performance for shoes treatment while preventing the air used for dehumidification and deodorization from being exposed to the user is present in in the process of treating the shoes.

However, there is a limitation in that the conventional shoes care device cannot properly solve such a task.

In addition, when designing and manufacturing devices including a dehumidifier such as zeolite, it is necessary to consider how the dehumidification efficiency of a dehumidifying material can be further improved, whether the dehumidifying material can be effectively regenerated, whether water vapor generated during the use of the shoes care device and the regeneration of the dehumidifying material can be effectively removed or managed, whether moisture is left in an unintended area during use of the shoes care device and the regeneration of the dehumidifying, whether components are properly disposed in a limited space, and whether the devices provides excellent use convenience. There is a need to develop a shoes care device that takes these matters into consideration.

In addition, the reduction of manufacturing costs, the convenience of manufacturing and assembling each component, and the convenience of maintenance needs to be considered in the development of the shoes care device.

DISCLOSURE

Technical Problem

An objective to be attained by the present disclosure is to provide a shoes care device that treats shoes by supplying steam to the inside of an inner cabinet where the shoes are placed and has an air circulation structure in which the air inside the inner cabinet is dehumidified using a dehumidifying material and in which the dehumidified air is supplied back into the inner cabinet, thereby caring for the shoes in the state in which the shoes are placed on the bottom of the inner cabinet, supplying uniformly steam to each of a pair of shoes, and enabling uniform shoes care.

An objective to be attained by the present disclosure is to provide a shoes care device having a structure capable of preventing the shoes from interfering with the supply of steam and avoiding damage to the shoes by steam in the case where a steam inlet is formed on the bottom of the inner cabinet.

An objective to be attained by the present disclosure is to provide a shoes care device having a structure that has a means, which is formed on the bottom of an accommodation space of the inner cabinet, for the user to easily recognize the preferred seating position of the shoe and prevents the steam inlet, through which steam is discharged, from being covered by the shoe even in the case where the shoe accommodated in the inner cabinet is very large.

An objective to be attained by the present disclosure is to provide a shoes care device capable of easily maintaining the shoes care device even when foreign substances are separated from the shoes and remain on the bottom of the inner cabinet during the shoe care process.

An objective to be attained by the present disclosure is to provide a shoes care device that uniformly treats a pair of shoes and easily discharges condensation water generated inside the inner cabinet.

Technical Solution

A shoes care device disclosed in the present disclosure is configured to include an inner cabinet, a door, a connection path, a blowing part, a dehumidifying part, a steam generator, and a steam inlet.

The inner cabinet has an accommodation space in which shoes are accommodated and a main opening that is open in a first direction as a horizontal direction.

The door is configured to open and close the main opening.

The connection path forms a flow path through which air is introduced from the accommodation space and then discharged back into the accommodation space.

The blowing part is disposed on the connection path and configured to blow air.

The dehumidifying part is disposed on the connection path and configured to dehumidify the air.

The steam generator is configured to generate steam.

The steam inlet forms an inlet through which the steam is introduced into the accommodation space. The steam inlet is formed on the bottom of the accommodation space or adjacent to the bottom. The steam inlet is located at the rear center of the accommodation space with respect to the first direction.

The shoes care device comprises a pair of first guide rib and second guide rib.

The first guide rib and the second guide rib protrude upward from the bottom surface of the accommodation space so as to support the front end or rear end of the shoe.

The first guide rib and the second guide rib are positioned on different sides based on a reference plane that is a vertical plane parallel to the first direction and crossing the steam inlet.

The bottom surface of the accommodation space is formed to be inclined downward in the first direction.

Each of the first guide rib and the second guide rib is formed in a curved shape that is concave in the first direction.

The first guide rib and the second guide rib are symmetrical to each other about the reference plane. The first guide rib and the second guide rib are formed in front of the accommodation space, based on the first direction.

Based on the rear end of the bottom surface of the accommodation space in the first direction, when a distance to the steam inlet is BD1, a distance to the first guide rib and the second guide rib is BD2, and a distance to the front end of the bottom surface of the accommodation space is BD3, the BD1 is 1/10 of the BD3 or less, and the BD2 is 9/10 to 10/10 of the BD3.

Opposite sides of the accommodation space are symmetrical to each other about the reference plane.

The inner cabinet comprises a first inner side plate, a second inner side plate, and an inner rear plate.

The first inner side plate forms a wall surface on the side where the first guide rib is position based on the reference plane.

The second inner side plate forms a wall surface on the side where the second guide rib is position based on the reference plane.

The inner rear plate forms a rear wall surface in the first direction and connects the first inner side plate and the second inner side plate.

The first guide rib may be formed to be more biased to the reference plane than the first inner side plate, and the second guide rib may be formed to be more biased to the reference plane than the second inner side plate.

The length of the steam inlet is 1/15 to 1/5 of the gap between the first inner side plate and the second inner side plate in a second direction, as the horizontal direction, perpendicular to the first direction.

The inner cabinet comprises a lower opening provided in the lower side of the accommodation space.

The shoes care device is configured to include a module housing and a main shelf.

The module housing is coupled to the lower side of the inner cabinet to shield the lower opening. The module housing forms a part of the connection path. The module housing has an outlet through which air of the accommodation space is introduced and a module chamber that is an inner space communicating with the outlet and accommodates the blowing part and the dehumidifying part.

The main shelf is seated on the upper side of the module housing. The main shelf has the first guide rib and the second guide rib formed on the upper surface thereof.

The outlet is formed at the front of the upper surface of the module housing in the first direction.

The main shelf has a shelf hole formed right above the outlet to vertically penetrate the same.

The first guide rib and the second guide rib are formed ahead of the shelf hole in the first direction.

The main shelf may be configured to include a plurality of main isolation ribs. The plurality of main isolation ribs protrudes upward from the upper surface of the main shelf and spaced apart from each other.

The main shelf is configured to include a main water stop rib forming an edge and protruding upward.

The shoes care device may be configured to include a bottom bar. The bottom bar has the steam inlet formed on an upper surface thereof. The bottom bar is interposed between the inner cabinet and the main water stop rib at the rear in the first direction.

The upper surface of the bottom bar is higher than or equal to the upper surface of the main water stop rib.

The main water stop rib may be in close contact with or close to the inner cabinet on both left and right sides in the first direction.

The steam inlet may be position behind the main shelf in the first direction. The steam inlet may penetrate in the vertical direction and have an upper end that is higher than the bottom of the main shelf.

The shoes care device may be configured to include a sump, a heating part, and a regeneration path.

The sump is provided on the lower side of the module housing and configured to accommodate condensed water.

The heating part is accommodated in the module chamber and configured to heat air in the module chamber.

The regeneration path forms a flow path through which the air in the module chamber, which has passed through the dehumidifying part, moves to the sump.

The module housing is configured to include a module case and a module cover.

The module case forms the module chamber and has a module opening that is open upward.

The module cover shields the module opening from an upper side of the blowing part, the heating part, and the dehumidifying part, is coupled to the module case, and has the outlet formed to penetrate therethrough.

Advantageous Effects

The shoes care device according to an embodiment of the present disclosure is configured to include an inner cabinet, a door, a connection path, a blowing part, a dehumidifying part, a steam generator, and a steam inlet. The steam inlet forms an inlet through which steam is introduced into the accommodation space of the inner cabinet. The door is position in front of the inner cabinet, and the steam inlet is position in the rear center of the accommodation space. According to an embodiment of the present disclosure, since shoes are cared while being placed on the bottom of the accommodation space, it is convenient to insert or remove shoes into or from the accommodation space, and shoes in various sizes can be easily cared. In addition, the steam generated by the steam generator may be distributed inside the inner cabinet to refresh the shoes, and the air inside the inner cabinet may be circulated through the connection path, thereby dehumidifying the air. Since the steam inlet is position in the rear center of the accommodation space, it is possible to minimize the possibility that a pair of shoes blocks the steam inlet when placed on the bottom of the accommodation space, and to uniformly supply steam to the respective shoes. In addition, even when high-temperature steam is discharged through the steam inlet, the steam may be discharged directly to the bottom of the shoes, thereby minimizing the possibility of uneven processing of a pair of shoes or damage to the shoes.

The shoes care device according to an embodiment of the present disclosure includes a pair of first guide rib and second guide rib. The first guide rib and the second guide rib are located on different sides, based on the reference plane. When a user places a pair of shoes on the bottom of the accommodation space, one shoe may be supported on the first guide rib and the other shoe may be supported on the second guide rib, thereby being placed on the bottom of the accommodation space. Therefore, the two shoes are located on different sides of the reference plane, and the steam inlet is located at one point of the reference plane. A pair of shoes, if it has a very large size, may be placed diagonally apart from each other toward the rear in the first direction. In this case, the steam inlet is located between the pair of shoes. In this way, according to an embodiment of the present disclosure, it is possible to minimize, when the size of the shoe is very large, the possibility that the steam inlet is obscured by the shoes or that the shoes are placed very close to the steam inlet.

The shoes care device according to an embodiment of the present disclosure may be configured to include a module housing and a main shelf. In this case, the first guide rib and the second guide rib are formed on the upper surface of the main shelf. Foreign substances separated from the shoes during the shoe care process may settle on the upper surface of the main shelf, and in this case, the user may separate the main shelf from the inner cabinet and wash the main shelf, making it easier to maintain the shoes care device.

In the shoes care device according to an embodiment of the present disclosure, the main shelf may be disposed to be inclined downward in a first direction, and a shelf hole may be formed in the main shelf, and the condensed water on the upper surface of the main shelf may flow into the module housing through the shelf hole and then move to the regeneration path. In addition, the shoes care device may be configured to include a bottom bar, and the main shelf may be configured to include a main water stop rib. In this case, the steam inlet is formed on the upper surface of the bottom bar, and the upper surface of the bottom bar is higher than or equal to the upper surface of the main water stop rib, and the main water stop rib is in close contact with or close to the inner cabinet on both left and right sides in the first direction. Therefore, it is possible to prevent steam released from the steam inlet from being supplied directly to the shoes, thereby preventing the shoes from being damaged by the steam. In addition, the water condensed in the accommodation space is located inside the main water stop rib, which is the edge of the main shelf, or moves to the regeneration path, enabling easy management of the condensed water in the shoes care device.

DESCRIPTION OF DRAWINGS

FIG. 1*a* is a perspective view illustrating a shoes care device according to one embodiment of the present invention.

FIG. 1*b* is a perspective view of the shoes care device of FIG. 1*a*, when viewed from another direction, illustrating a state in which a door is opened.

FIG. 2*a* is a perspective view illustrating a state in which a part of the door and an outer cabinet are removed from the shoes care device of FIG. 1*b*.

FIG. 2*b* is a perspective view illustrating a state in which the shoes care device illustrated in FIG. 2*a* is viewed from another direction.

FIG. 3 illustrates shoes accommodated in an inner cabinet together.

FIG. 4*a* is a cross-sectional view taken along line 4*a*-4*a*' of the shoes care device illustrated in FIG. 3. FIG. 4*b* is a cross-sectional view taken along line 4*b*-4*b*' of the shoes care device illustrated in FIG. 3, and FIG. 4*c* is a cross-sectional view taken along line 4*c*-4*c*' of the shoes care device illustrated in FIG. 3. FIGS. 4*a* to 4*c* illustrate a form where a door is included in the shoes care device, and do not illustrate shoes.

FIG. 5 is a perspective view illustrating a state in which the door, the outer cabinet, and the inner cabinet are removed from the shoes care device according to one embodiment of the present invention.

FIG. 6 is a perspective view illustrating a part of a machine room of the shoes care device illustrated in FIG. 5.

FIG. 7*a* is a view illustrating a steam valve according to one embodiment of the present invention, and illustrating a connection relationship considering the movement of steam.

FIG. 7*b* is an exploded perspective view illustrating the steam valve illustrated in FIG. 7*a*.

FIG. 8*a* is a cross-sectional view taken along line 8*a*-8*a*' of the shoes care device illustrated in FIG. 3. FIG. 8*a* illustrates a state in which the door is included in the shoes care device, and does not illustrate the shoes.

FIG. 8*b* is a view illustrating a state in which a main shelf is removed from the shoes care device illustrated in FIG. 8*a*.

FIG. 9 is a cross-sectional view taken along line 9-9' of the shoes care device illustrated in FIG. 3. FIG. 9 illustrates a state in which the door is included in the shoes care device.

FIG. 12*a* is an exploded perspective view illustrating the condenser according to one embodiment of the present invention.

FIG. 12*b* is a view illustrating an inner state of the condenser of FIG. 12*a*.

FIG. 12*c* is a front view illustrating the condenser of FIG. 12*b*.

FIG. 13 is a cross-sectional view illustrating a first module chamber of a module housing in the shoes care device according to one embodiment of the present invention.

FIG. 14 is a perspective view illustrating a dehumidifying part and a dehumidifying material housing according to one embodiment of the present invention.

FIG. 15 is a bottom perspective view illustrating a module cover according to one embodiment of the present invention.

FIG. 16 is a cross-sectional view illustrating a part of a third module chamber of the module housing in the shoes care device according to the present invention.

FIG. 17 is a perspective view illustrating a steam separator according to one embodiment of the present invention.

FIG. 18*a* is a cross-sectional view illustrating a part of a separating inlet of a steam separator in the shoes care device according to one embodiment of the present invention.

FIG. 18*b* is a cross-sectional view illustrating a part of a separating connector of the steam separator in the shoes care device according to one embodiment of the present invention.

FIGS. 19*a* and 19*b* are perspective views illustrating the main shelf according to one embodiment of the present invention.

FIG. 20 is a cross-sectional view illustrating the shoes care device according to one embodiment of the present invention, and schematically illustrating a state in which the shoe is settled on an upper side of the main shelf.

FIG. 21 is a cross-sectional view illustrating the shores care device according to one embodiment of the present invention and is a view schematically illustrating a state in which the shoes having a larger size than that of FIG. 20 is settled on the upper side of the main shelf.

FIG. 22 is a view illustrating the inside of the module housing according to one embodiment of the present invention. FIG. 22 illustrates that a schematic flow direction of air inside the module housing is indicated by an arrow.

FIG. 23 is a view illustrating the inside of the module housing according to one embodiment of the present invention. FIG. 23 illustrates a dehumidifying material cover together.

FIG. 24 is a perspective view illustrating a drying module according to one embodiment of the present invention.

FIG. 25 is a bottom perspective view illustrating the dehumidifying material cover illustrated in FIG. 24.

FIG. 26 is a cross-sectional view illustrating the drying module of FIG. 24.

FIGS. 27*a* and 27*b* are views illustrating simulation results of air speed distribution when an inner rib is not formed in the module housing according to one embodiment of the present invention, and FIGS. 28*a* and 28*b* are diagrams illustrating simulation results of the air speed distribution when the inner rib is formed in the module housing according to another embodiment of the present invention.

FIG. 29*a* is a view illustrating the entire area of the dehumidifying part divided into six areas in a plan view in the shoes care device according to one embodiment of the present invention, and FIG. 29*b* is a view illustrating a mass flow rate in each area of FIG. 29*a*.

MODES FOR THE INVENTION

Figure 3:
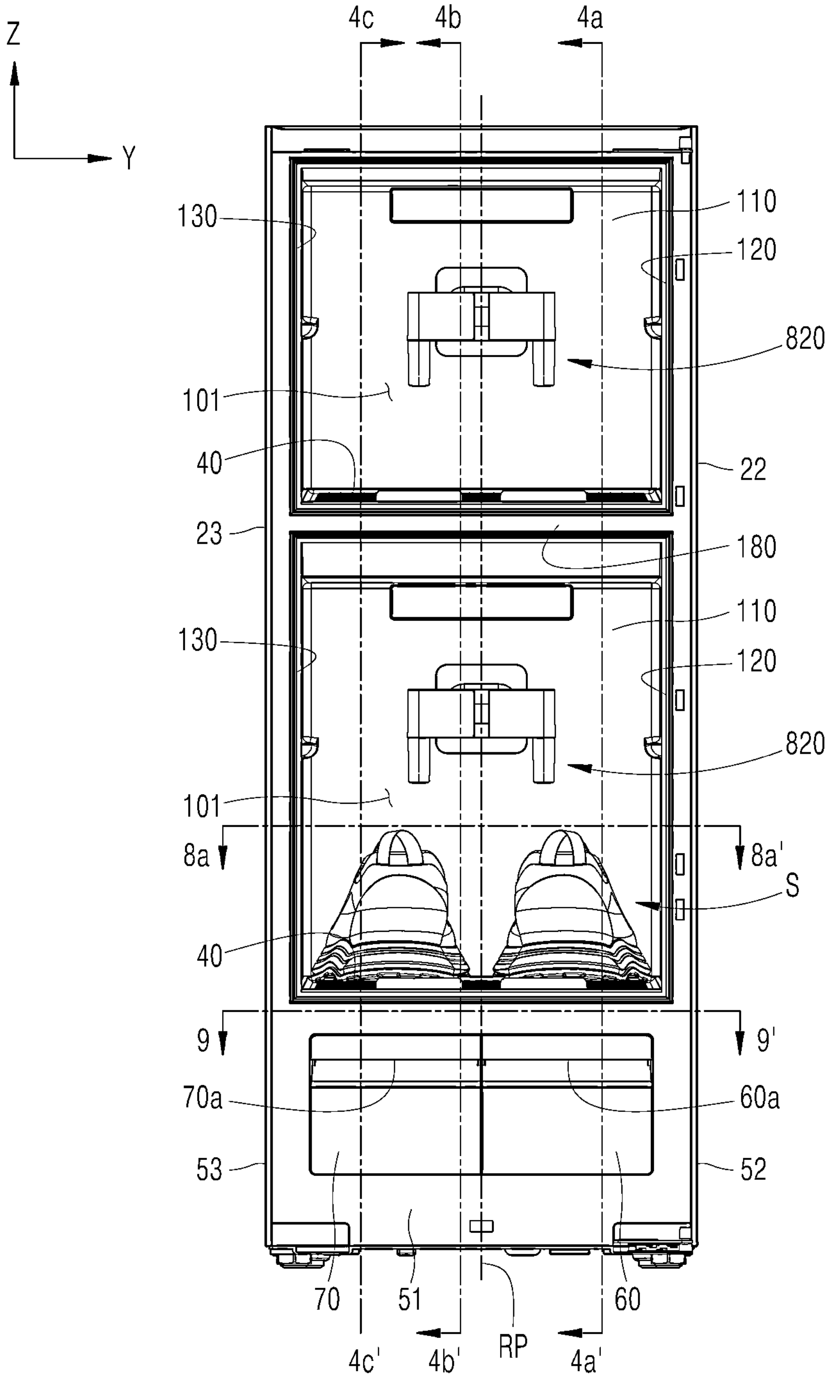
FIG. 3 is a front view illustrating a state in which a door is removed from the shoes care device illustrated in FIG. 1*b*.

Hereinafter, exemplary embodiments disclosed herein will be described in detail with reference to the accompanying drawings, and like reference numerals designate like elements, and redundant description thereof will be omitted. Suffixes "module" and "unit or portion" for elements used in the following description are merely provided for facilitation of preparing this specification, and thus they are not granted a specific meaning or function. Wherever possible, the same reference numbers will be used throughout the drawings to refer to the same or like parts. In the following description, known functions or structures, which may confuse the substance of the present disclosure, are not explained. The accompanying drawings are used to help easily explain various technical features and it should be understood that the exemplary embodiments presented herein are not limited by the accompanying drawings. As such, the present disclosure should be construed to extend to any alterations, equivalents and substitutes in addition to those which are particularly set out in the accompanying drawings.

Although the terms first, second, and the like, may be used herein to describe various elements, these elements should not be limited by these terms. These terms are generally only used to distinguish one element from another.

When an element or layer is referred to as being "on," "engaged to," "connected to," or "coupled to" another element or layer, it may be directly on, engaged, connected, or coupled to the other element or layer, or intervening elements or layers may be present. In contrast, when an element is referred to as being "directly on," "directly engaged to," "directly connected to," or "directly coupled to" another element or layer, there may be no intervening elements or layers present.

The singular expressions include plural expressions unless the context clearly dictates otherwise.

It should be understood that the terms "comprises," "comprising," "includes," "including," "containing," "has," "having" or any other variation thereof specify the presence of stated features, integers, steps, operations, elements, and/or components, but do not preclude the presence or addition of one or more other features, integers, steps, operations, elements, and/or components.

A first direction (X direction), a second direction (Y direction), and a third direction (Z direction) described in one embodiment of the present invention may be directions orthogonal to each other.

Each of the first direction (X direction) and the second direction (Y direction) may be a direction parallel to the horizontal direction, and the third direction (Z direction) may be a direction parallel to the vertical direction. When the first direction (X direction) is parallel to a left-right direction, the second direction (Y direction) may be parallel to a front-rear direction. When the first direction (X direction) is parallel to the front-rear direction, the second direction (Y direction) may be parallel to the left-right direction.

FIG. 1*a* is a perspective view illustrating a shoes care device 1 according to one embodiment of the present invention.

FIG. 1*b* is a perspective view of the shoes care device of FIG. 1*a*, when viewed from another direction, illustrating a state in which a door is opened.

FIG. 2*a* is a perspective view illustrating a state in which a part of the door and an outer cabinet are removed from the shoes care device of FIG. 1*b*.

FIG. 2*b* is a perspective view illustrating a state in which the shoes care device illustrated in FIG. 2*a* is viewed from another direction.

A shoes care device 1 according to one embodiment of the present invention may include an outer cabinet 20, a door 30, an inner cabinet 100, and a machine room 50. The shoes care device 1 may include a main frame 5.

The outer cabinet 20 and the door 30 may form an overall appearance of the shoes care device 1. The outside of the shoes care device 1 may be formed in a hexahedral shape. That is, while the outer cabinet 20 and the door 30 are coupled to each other and the door 30 is closed, the appearance of the shoes care device 1 may be formed in a hexahedral shape. However, the shoes care device 1 according to one embodiment of the present invention is not limited to such a shape and may have various three-dimensional shapes.

When the door 30 forms the front of the shoes care device 1, the outer cabinet 20 may form an upper side surface, a left-side surface, a right-side surface, a rear surface, and bottom surfaces of the shoes care device 1.

The main frame 5 may form an overall framework of the shoes care device 1. The main frame 5 may have a hexahedral structure.

The outer cabinet 20 may be detachably fixed to the main frame 5.

The outer cabinet 20 may include an outer rear plate 21, a first outer side plate 22, and a second outer side plate 23.

The outer rear plate 21, the first outer side plate 22, and the second outer side plate 23 may be formed integrally with each other, or the outer rear plate 21, the first outer side plate 22, and the second outer side plate 23 may be individually formed.

The outer rear plate 21 forms a vertically erected wall surface. The outer rear plate 21 may form a surface orthogonal to the first direction (X direction). The outer rear plate 21 may form a rear wall surface in the first direction (X direction) on the outer cabinet 20. The outer rear plate 21 may form a rear surface in the first direction (X direction) in the shoes care device 1. The outer rear plate 21 may form an entire outer rear surface of the shoes care device 1.

The first outer side plate 22 and the second outer side plate 23 form vertically erected wall surfaces, respectively, and form opposing wall surfaces facing each other.

The first outer side plate 22 is disposed at any one side with respect to a reference plane RP that is parallel to the first direction (X direction) as a horizontal direction and is a vertical plane. The second outer side plate 23 is disposed on the opposite side of the first outer side plate 22 with respect to the reference plane RP. The first outer side plate 22 may form a left wall surface of the outer cabinet 20, and the second outer side plate 23 may form a right wall surface of the outer cabinet 20.

The outer cabinet 20 may be disposed outside the inner cabinet 100 and the machine room 50 to form an outer wall surface of the machine room 50. When a separate cabinet for the machine room 50 is not provided in the shoes care device 1, the outer cabinet 20 may form a wall separating the machine room 50 from the outside.

The door 30 is configured to open and close the inside of the shoes care device 1. The door 30 may form any one surface of the shoes care device 1. The door 30 may form a left side or a right side of the shoes care device 1, or may form a front side of the shoes care device 1.

In the shoes care device 1, the door 30 may be hinge-coupled.

In one embodiment, the door 30 may be hinge-coupled to the main frame 5. In another embodiment, the door 30 may be hinge-coupled to the outer cabinet 20, and in another embodiment, the door 30 may be hinge-coupled to the inner cabinet 100 and/or the machine room 50.

A hinge rotation axis 31 of the door 30 may be formed in the vertical direction. That is, in the shoes care device 1, the door 30 may be configured to be rotatable bidirectionally around a rotation axis 31 in the vertical direction.

In one embodiment, the shoes care device 1 may include one door 30. In another embodiment, the shoes care device 1 may include two or more doors.

When two doors are provided in the shoes care device 1, each door may be individually rotated around each rotation axis.

The first direction (X direction) described in one embodiment of the present invention may be parallel to or substantially parallel to the horizontal direction.

In one embodiment, the first direction (X direction) may be a direction from the rear of the shoes care device 1 to the front.

Hereinafter, except for a particularly limited case, it will be described that the door 30 is formed in a front side of the shoes care device 1. That is, a surface on which the door 30 is formed in the shoes care device 1 is described as a front surface of the shoes care device 1.

Furthermore, hereinafter, except for a particularly limited case, it will be described that the first direction (X direction) is parallel to the front-rear direction, the second direction (Y direction) is parallel to the left-right direction, and the third direction (Z direction) is parallel to the vertical direction.

The inner cabinet 100 and the machine room 50 may be provided inside the outer cabinet 20.

The inner cabinet 100 may be formed in a box shape, and a predetermined space may be formed therein. The space inside the inner cabinet 100 forms an accommodation space 101, and shoes S may be accommodated in the accommodation space 101.

A plurality of shoes S may be disposed together in the accommodation space 101 of one inner cabinet 100.

The inner cabinet 100 may be fixed to the main frame 5.

The inner cabinet 100 has a predetermined size along the first direction (X direction), the second direction (Y direction), and the third direction (Z direction).

The inner cabinet 100 is formed in the shape of a box opened to any one side. The inner cabinet 100 may be formed in a form opened to the front side of the shoes care device 1. The inner cabinet 100 may be configured to include a main opening 140. The main opening 140 may be provided to open the front side of the inner cabinet 100 in the first direction (X direction). The shoes may be disposed inside the inner cabinet 100 or withdrawn from the inner cabinet 100 through the main opening 140.

The main opening 140 of the inner cabinet 100 may be closed or opened by the door 30.

The inner cabinet 100 may include an inner rear plate 110, a first inner side plate 120, a second inner side plate 130, and an inner upper plate 115.

The inner rear plate 110, the first inner side plate 120, the second inner side plate 130, and the inner upper plate 115 may be formed integrally with each other. The inner cabinet 100 may be made of a single material and be formed by injection molding.

The inner rear plate 110 forms a vertically erected wall surface. The inner rear plate 110 may form a surface orthogonal to the first direction (X direction). The inner rear plate 110 may form a rear wall surface of the inner cabinet 100 in the first direction (X direction). The inner rear plate 110 may be formed parallel to the outer rear plate 21.

The first inner side plate 120 and the second inner side plate 130 form vertically erected wall surfaces, respectively, and form opposing wall surfaces facing each other.

The first inner side plate 120 is dispose on either side with respect to the reference plane RP that is parallel to the first direction (X direction) as the horizontal direction and is a vertical surface. The second inner side plate 130 is disposed on the opposite side of the first inner side plate 120 with respect to the reference plane RP. The first inner side plate 120 forms a left wall surface of the inner cabinet 100, and the second inner side plate 130 forms a right wall surface of the inner cabinet 100.

The first inner side plate 120 may be formed parallel to the first outer side plate 22, and the second inner side plate 130 may be formed parallel to the second outer side plate 23.

In one embodiment of the present invention, the inner cabinet 100 may have the form where a lower part thereof is opened. Accordingly, the inner cabinet 100 includes a lower opening formed by opening the lower part thereof. When the inner cabinet is formed in a hexahedral shape on the whole, the lower opening may be formed large to form all or most of a lower surface of the inner cabinet 100.

However, the shoes care device 1 according to one embodiment of the present invention is not used in a state in which an entire lower part of the inner cabinet 100 is opened, but is used in a state in which the inner cabinet 100 and a module housing 200 are coupled to each other so that the lower opening of the inner cabinet 100 is shielded by the module housing 200. That is, the shoes care device 1 is used so that an upper surface of the module housing 200 forms a bottom surface of the accommodation space 101 of the inner cabinet 100. A further explanation thereof will be described below.

A main shelf 40 may be provided in the inside 101 of the inner cabinet 100. The main shelf 40 may be formed such that the shoes S are settled on an upper surface thereof.

The main shelf 40 may be formed in the form of a plate with a predetermined area, or may be formed in the form of a grill where multiple bars are spaced apart from each other.

One main shelf 40 may be provided, or a plurality of main shelves 40 may be provided.

The main shelf 40 may have a substantially flat plate shape and be disposed on a bottom surface of the inner cabinet 100. The main shelf 40 is settled on an upper side of a module cover 202 of the inner cabinet 100. The main shelf 40 may be disposed on the upper side of the module cover 202 of the inner cabinet 100 in a stacked form.

The main shelf 40 is detachable from the inner cabinet 100, and when the main shelf 40 is withdrawn from the inner cabinet 100, the upper surface of the module housing 200 is exposed.

The main shelf 40 may have a rectangular shape when viewed in a plan view. The size of the main shelf 40 may be a size corresponding to the bottom of the accommodation space 101 of the inner cabinet 100. That is, when the main shelf 40 is disposed inside the inner cabinet 100, the main shelf 40 may form all or most of the bottom of the accommodation space 101 of the inner cabinet 100.

In one embodiment, the machine room 50 may be provided in a lower side of the inner cabinet 100. In the machine room 50, some of the components that constitutes the shoes care device 1 may be accommodated, and, in this case, the components that are accommodated in the machine room 50 may be fixed to a main frame 5 or to the inner cabinet 100 or the outer cabinet 20.

FIG. 3 is a front view illustrating a state in which a door is removed from the shoes care device illustrated in FIG. 1*b*. FIG. 3 illustrates shoes accommodated in an inner cabinet together.

FIG. 4*a* is a cross-sectional view taken along line 4*a*-4*a*' of the shoes care device illustrated in FIG. 3. FIG. 4*b* is a cross-sectional view taken along line 4*b*-4*b*' of the shoes care device illustrated in FIG. 3, and FIG. 4*c* is a cross-sectional view taken along line 4*c*-4*c*' of the shoes care device illustrated in FIG. 3. FIGS. 4*a* to 4*c* illustrate a form where a door is included in the shoes care device, and do not illustrate shoes.

The shoes care device 1 according to one embodiment of the present invention includes management devices 2*a* and 2*b*. In the shoes care device 1, a plurality of management devices 2*a* and 2*b* may be provided. In one embodiment, the shoes care device 1 may include a first management device 2*a* and a second management device 2*b*. That is, the shoes care device 1 may include two separate management devices 2*a* and 2*b*.

The 'management device' described in the present invention may refer to a 'first management device 2*a*' and a 'second management device 2*b*', respectively, except for a particularly limited case.

The management devices 2*a* and 2*b* include the above-described inner cabinet 100.

In one embodiment of the present invention, since the inner cabinet 100 of the first management device 2*a* and the inner cabinet 100 of the second management device 2*b* may be distinguished from each other, the inner cabinet 100*a* of the first management device 2*a* may refer to a first inner cabinet 100*a*, and inner cabinet 100*b* of the second management device 2*b* may refer to a second inner cabinet 100*b*.

It may be understood that the 'inner cabinet 100' described in one embodiment of the present invention refers to each of the 'first inner cabinet 100*a*' and the 'second inner cabinet 100*b*', except for a particularly limited case.

When the door 30 is closed in the shoes care device 1, the door 30 closes the main opening 140 of the first management device 2*a* and also closes the main opening 140 of the second management device 2*b*. That is, the door 30 may simultaneously seal the accommodation space 101 of the inner cabinet 100 of the first management device 2*a* and the accommodation space 101 of the inner cabinet 100 of the second management device 2*b*. In this case, the accommodation space 101 of the inner cabinet 100 of the first management device 2*a* and the accommodation space 101 of the inner cabinet 100 of the second management device 2*b* may be configured such that they do not communicate with each other.

As described above, in one embodiment of the present invention, the accommodation space 101 of the inner cabinet 100 of the first management device 2*a* and the accommodation space 101 of the inner cabinet 100 of the second management device **2*b* may form independent spaces, and may form blocked spaces (not communicating with each other). Accordingly, the temperature and humidity of the accommodation space 101 of the first management device 2*a* and the temperature and humidity of the accommodation space 101 of the second management device 2*b*** may be controlled differently from each other.

The management devices **2*a* and 2*b* may be configured to include a connection path F10. The management devices 2*a* and 2*b* may be configured to include a blowing part 310 and a dehumidifying part 330. The management devices 2*a* and 2*b* may include an outlet 203 and a nozzle 820**.

The management devices **2*a* and 2*b* may include the module housing 200 forming a connection path F10. The module housing 200 forms all or part of the connection path F10**.

The management devices **2*a* and 2*b* may include a regeneration path F20. The management devices 2*a* and 2*b* may include a heating part 320**.

The management devices **2*a* and 2*b* may include a conversion flow path F10*a***.

The management devices **2*a* and 2*b* may include a damper 350**.

The shoes care device 1 may include a steam generator 700 and a steam valve 710.

The shoes care device 1 may include a sump 600, a water supply tank 60, and a drain tank 70.

Since all or part of the outer cabinet 20 may be spaced apart from the inner cabinet 100, a predetermined gap may be formed between the inner cabinet 100 and the outer cabinet 20.

In a space between the inner cabinet 100 and the outer cabinet 20, components constituting the shoes care device 1 may be provided, and various flow paths constituting the shoes care device 1 may be provided. In one embodiment of the present invention, part of the connection path F10 may be provided between the inner cabinet 100 and the outer cabinet 20, and part of the regeneration path F20 may be provided between the inner cabinet 100 and the outer cabinet 20.

A dry air duct 370 forming the connection path F10 may be provided between the outer rear plate 21 and the inner rear plate 110. Furthermore, a condenser 400 forming the regeneration path F20 may be provided between the first outer side plate 22 and the first inner side plate 120.

The connection path F10 forms a flow path of a fluid.

The connection path F10 forms a passage through which air and/or condensed water inside the shoes care device 1 moves.

The dehumidifying part 330 is disposed inside the connection path F10 and includes a dehumidifying material. The dehumidifying part 330 may be entirely formed of the dehumidifying material, or a part thereof may be formed of the dehumidifying material. A further explanation of the dehumidifying part 330 will be described below.

According to one embodiment of the present invention, the shoes care device 1 has an air circulation structure in which the air inside the inner cabinet 100 in which the shoes are disposed is sucked into the connection path F10 to dehumidify the air using a dehumidifying material 331 and the dehumidified air may be supplied back into the inner cabinet 100.

The connection path F10 may be used as a means to achieve such an air circulation structure in the shoes care device 1. All or part of the connection path F10 may be formed of a pipe, a hose, a tube, a duct, a housing, or a combination thereof.

The module housing 200 according to one embodiment of the present invention forms part of the connection path F10.

The outlet 203 is formed in the module housing 200. The outlet 203 communicates with the accommodation space 101 of the inner cabinet 100, and forms an inlet of the module housing 200 through which the air of the accommodation space 101 of the inner cabinet 100 is suctioned into the module housing 200. The outlet 203 may be disposed below the main shelf 40. In this case, the main shelf 40 may be formed so as not to block the air in the accommodation space 101 from being sucked into the outlet 203. To this end, when the main shelf 40 is formed in a plate shape, a plurality of holes 45 penetrating in the vertical direction may be formed in the main shelf 40 so as to move the air.

In the shoes care device 1, the inner cabinet 100 and the machine room 50 may form a space separated from each other. Furthermore, the module housing 200 that is part of the management devices **2*a* and 2*b* may be provided between the inner cabinet 100 and the machine room 50**.

The inner cabinet 100, the module housing 200, and the machine room 50 are provided inside the shoes care device 1 according to one embodiment of the present invention.

The inner cabinet 100, the module housing 200, and the machine room 50 may be continuously arranged from the upper side to the lower side. When the shoes care device 1 according to one embodiment of the present disclosure includes the first management device **2*a* and the second management device 2*b*, the first management device 2*a* may be disposed above the second management device 2*b*. That is, the first management device 2*a*, the second management device 2*b*, and the machine room 50** may be continuously arranged from the upper side to the lower side.

Since the first management device **2*a* and the second management device 2*b* include the inner cabinet 100 and the module housing 200, respectively, they may be continuously arranged in an order of the inner cabinet 100 of the first management device 2*a*, the module housing 200 of the first management device 2*a*, the inner cabinet 100 of the second management device 2*b*, the module housing 200 of the second management device 2*b*, the machine room 50** from the upper side to the lower side.

The inner cabinet 100 may form a space that mainly accommodates an article (shoes S) to be managed, and the module housing 200 and the machine room 50 may form a space that mainly accommodates components for an operation of the shoes care device 1.

In the shoes care device 1 according to one embodiment of the present invention, the blowing part 310, the dehumidifying part 330 (and the dehumidifying material 331), and the heating part 320 may be accommodated inside the module housing 200.

In addition, the machine room 50 may be configured to accommodate a controller 10, the sump 600, the steam generator 700, and the steam valve 710 therein. Furthermore, the machine room 50 may be configured to accommodate the water supply tank 60 and the drain tank 70.

Among the components constituting the management devices **2*a* and 2*b*, components not included in the module housing 200 may be fixedly coupled to the inner cabinet 100 and the outside of the module housing 200 or may be fixedly coupled to the main frame 5**.

Components coupled to or accommodated in the machine room 50 may be fixedly coupled to the machine room 50.

The machine room 50 may include a first wall 51.

A first wall 51 forms one wall surface of the machine room 50. The first wall 51 may be erected in the vertical direction, or may be erected in the substantially vertical direction. In one embodiment, the first wall 51 may form a wall surface orthogonal to or inclined with the first direction (X direction).

The first wall 51 may form a front wall surface of the machine room 50, a left wall of the machine room 50, or a right wall of the machine room 50.

The machine room 50 may include a second wall 52 and a third wall 53. The second wall 52 and the third wall 53 form opposite wall surfaces facing each other in the machine room 50. The second wall 52 and the third wall 53 may be erected in the vertical direction, or may be erected in the substantially vertical direction.

When the first wall 51 forms a front wall of the machine room 50, the second wall 52 may form a left wall of the machine room 50, and the third wall 53 may form a right wall of the machine room 50.

The first wall 51 may be formed integrally with the inner cabinet 100, and the second wall 52 and the third wall 53 may be formed integrally with the outer cabinet 20, respectively.

Each of the water supply tank 60 and the drain tank 70 may be formed in the form of a container for accommodating water.

The water supply tank 60 may be configured to store water supplied into the shoes care device 1 inside. The water supply tank 60 may be configured to store water supplied into the steam generator 700 inside.

In order to supply water from the water supply tank 60 into the shoes care device 1, a water pump 61 may be connected to the water supply tank 60. The water supply tank 60 and the first water pump 61 may be connected by a pipe, a hose, etc.

The drain tank 70 may be configured to store water discharged from the shoes care device 1 inside. The drain tank 70 may store water condensed inside the shoes care device 1. The drain tank 70 may be configured to store water drained from the sump 600.

In order to discharge water to the drain tank 70, a water pump 71 (a second water pump) may be connected to the drain tank 70. The drain tank 70 and the second water pump 71 may be connected by a pipe, a hose, etc.

The water supply tank 60 and the drain tank 70 may be coupled to the machine room 50 to get exposed from the outside of one wall surface of the machine room 50.

The water supply tank 60 and the drain tank 70 may be disposed in front of the machine room 50.

The water supply tank 60 and the drain tank 70 may form one wall surface of the machine room 50 along with the first wall 51. When the first wall 51 forms a front surface of the machine room 50, the water supply tank 60 and the drain tank 70 may be exposed from a front side of the machine room 50, and may be coupled to the machine room 50 to get exposed from the outside of the first wall 51.

As the water supply tank 60 and the drain tank 70 are exposed to the outside of the first wall 51, a user may inject water into the water supply tank 60 or discharge water from the drain tank 70.

The water supply tank 60 and the drain tank 70 may be configured to be detachable from the machine room 50. The water supply tank 60 and the drain tank 70 may be detached from the first wall 51. In order to facilitate the attachment and detachment of the water supply tank 60 and the drain tank 70, a handle 60*a* of the water supply tank 60 may be formed on an outer surface of the water supply tank 60, and a handle 70*a* of the drain tank 70 may be formed on an outer surface of the drain tank 70.

Each of the water supply tank 60 and the drain tank 70 may be configured to be separated from the machine room 50 in an outer direction of the first wall 51.

The controller 10 may be configured to control operations of each component in connection with each component constituting the shoes care device 1.

In order to control the controller 10, the shoes care device 1 may be provided with a storage medium in which an application program is stored, and the controller 10 may be configured to control the shoes care device 1 by driving an application program according to information input to the shoes care device 1 and information output from the shoes care device 1.

The controller 10 may control the first management device 2*a* and the second management device 2*b* constituting the shoes care device 1 to operate individually. The controller 10 may control the first management device 2*a* and the second management device 2*b* to operate in different states, and may control shoes (e.g., sneakers) in the first management device 2*a* and shoes (e.g., heels) in the second management device 2*b* to be managed under different conditions. Furthermore, the controller 10 may control the first management device 2*a* and the second management device 2*b* to interwork with each other.

The door 30 may be disposed on either the inner cabinet 100 or the machine room 50 on the same side as the first wall 51. When the door 30 forms the front surface of the shoes care device 1, the first wall 51 forms the front surface of the machine room 50, and the door 30 is disposed directly outside the first wall 51.

In one embodiment of the present invention, the door 30 may be configured to open and close the inner cabinet 100 and further expose or shield the front surface of the machine room 50.

The door 30 may be configured to expose or shield the inner cabinet 100, the water supply tank 60, and the drain tank 70.

As described above, in the shoes care device 1, the door 30, the water supply tank 60, and the drain tank 70 are formed on the same side, and when the door 30 is opened, the water supply tank 60 and the drain tank 70 may be exposed and separated from the shoes care device 1.

In the arrangement explained above, even if left and right sides and a rear side of the shoes care device 1 are blocked by other goods or structures, the door 30 may be opened on a front side of the shoes care device 1, and the water supply tank 60 and the drain tank 70 can be separated from or coupled again to the shoes care device 1.

A control panel 33 for controlling the shoes care device 1 is provided on an outer side of the door 30. The control panel 33 may be formed of a touch screen. A control unit (controller 10) is provided in the inner space of the door 30 to control each component of the shoes care device 1 in connection with the control panel 33. The controller 10 may be provided inside the machine room 50.

As illustrated in FIGS. 1*a* and 1*b*, in one embodiment, the door 30 may be configured to simultaneously expose or shield the inner cabinet 100 and the machine room 50.

In another embodiment, the door 30 may be configured to open and close only the inner cabinet 100. In this case, the machine room 50 may not be shielded by the door 30. Furthermore, in this case, the shoes care device 1 according to one embodiment of the present invention may be further provided with a dedicated door of the machine room 50 to open and close the machine room 50 separately from the door 30.

FIG. 5 is a perspective view illustrating a state in which the door 30, the outer cabinet 20, and the inner cabinet 100 are removed from the shoes care device 1 according to one embodiment of the present invention.

FIG. 6 is a perspective view illustrating a machine room part of the shoes care device 1 illustrated in FIG. 5.

FIG. 7*a* is a view illustrating the steam valve 710 according to one embodiment of the present invention, and illustrating a connection relationship considering the movement of steam. FIG. 7*b* is an exploded perspective view illustrating the steam valve illustrated in FIG. 7*a*.

The shoes care device 1 is provided with the steam generator 700 as a device configured so as to generate moisture inside the inner cabinet 100. The steam generator 700 may be provided inside the machine room 50. The steam generator 700 is configured to generate steam and selectively supply moisture and steam to the inside of the inner cabinet 100.

The shoes care device 1 according to one embodiment may be provided with one steam generator 700, and the shoes care device 1 according to another embodiment may be provided with two or more steam generators 700.

When the shoes care device 1 is provided with one steam generator 700, the steam generator 700 may be configured to supply steam into the inner cabinet 100 of the first management device 2*a* and/or into the inner cabinet 100 of the second management device 2*b*.

When the shoes care device 1 is provided with two or more steam generators 700, one of the steam generators 700 may supply steam to the inner cabinet 100 of the first management device 2*a*, and the other steam generator 700 may supply steam to the inner cabinet 100 of the second management device 2*b*.

Moist air formed by the steam generator 700 ('air' described in one embodiment of the present invention may be 'air including moisture') is supplied toward the accommodation space 101 of the inner cabinet 100, and moisture may be circulated in the accommodation space 101 of the inner cabinet 100, and accordingly, the moisture may be supplied to the shoes S.

The shoes care device 1 according to one embodiment of the present invention may be a refresher device that refreshes the shoes.

Here, refreshing may refer to a process of removing contaminants, deodorizing, sanitizing, preventing static electricity, or warming by supplying air, heated air, water, mist, steam, etc. to the shoes.

The steam generator 700 may supply steam to the accommodation space 101 of the inner cabinet 100 in which the shoes S are accommodated, and may perform steam treatment on the shoes, which is further meant to exert a refreshing effect due to swelling of shoes materials as well as sterilization by high-temperature steam.

The steam generator 700 is provided with a separate heater 700*a* that heats an inner space and water in the inner space and is configured to heat water to generate steam and supply the heated water to the accommodation space 101 of the inner cabinet 100.

An external faucet, etc., as a water supply source for supplying water to the steam generator 700, may be used, or a container-type water supply tank provided on one side of the machine room 50 may be used. The steam generator 700 may generate steam by receiving water from the water supply tank 60.

The water supply tank 60 and the steam generator 700 may be connected by a pipe, a hose, etc.

The steam generator 700 and the inner cabinet 100 may be connected by a pipe, a hose, etc. In the shoes care device 1 according to one embodiment of the present invention, as described below, the steam generated by the steam generator 700 may be supplied into the inner cabinet 100 after passing through the steam valve 710 and a steam separator 720. In this case, in order to move the steam, the steam generator 700 and the steam valve 710 may be connected by a pipe, a hose, etc., and the steam valve 710 and the steam separator 720 may also be connected by a pipe, a hose, etc.

The steam valve 710 may be disposed adjacent to the steam generator 700, and the steam valve 710 may be provided in the machine room 50. The steam generator 700 and the steam valve 710 may be provided below the second management device 2*b*.

The steam valve 710 is configured to selectively communicate with each of the accommodation space 101 of the first management device 2*a* and the accommodation space 101 of the second management device 2*b*, respectively.

When the steam of the steam generator 700 is supplied to the accommodation space 101 of the first management device 2*a* and/or the accommodation space 101 of the second management device 2*b*, the steam valve 710 operates to control whether the stream is supplied or not, and an operation of the stream 710 is driven by the controller 10.

The steam valve 710 includes a valve housing 711, a valve inlet 712, a first valve outlet 713, a second valve outlet 714, a valve disk 715, and a valve motor 716. In the steam valve 710 illustrated in FIGS. 7*a* and 7*b*, the other outlets except the valve inlet 712, the first valve outlet 713, and the second valve outlet 714 may be blocked by a stopper and deactivated.

The valve housing 711 forms a body of the steam valve 710, and has a predetermined inner space formed inside.

The valve inlet 712 may have a tubular shape and be coupled to the valve housing 711 to communicate with the inner space of the valve housing 711. The valve inlet 712 is a part connected to the steam generator 700, and steam may flow into the steam valve 710 (inside the valve housing 711) through the valve inlet 712.

The first valve outlet 713 and the second valve outlet 714 may be formed in a tubular shape and be coupled to the valve housing 711 to communicate with the inner space of the valve housing 711.

The first valve outlet 713 and the second valve outlet 714 are outlets through which steam is discharged from the steam valve 710. The first valve outlet 713 is connected to the accommodation space 101 of the first management device 2*a*, and the second valve outlet 714 is connected to the accommodation space 101 of the second management device 2*b*.

The valve disk 715 is provided inside the steam valve 710 (inside the valve housing 711) and is configured to open and close a flow path inside the steam valve 710. The valve disk 715 may be configured to selectively open and close a flow path of the first valve outlet 713 and a flow path of the second valve outlet 714.

The valve disk 715 is disposed between the valve inlet 712 and the first valve outlet 713, or between the valve inlet 712 and the second valve outlet 714, inside the valve housing 711. The valve disk 715 allows the valve inlet 712 and the first valve outlet 713 to communicate with each other or block the communication therewith, and also allows the valve inlet 712 and the second valve outlet 714 to communicate with each other or block the communication therewith.

In one embodiment of the present invention, the valve disk 715 may be formed in a circular plate shape and may include a valve hole 715*a*. The valve hole 715*a* is a hole penetrating the valve disk 715. The valve disk 715 may be rotatably coupled to the valve housing 711 around a valve rotation axis 715*b*, and the valve hole 715*a* may be formed eccentrically from the valve rotation axis 715*b*.

The valve motor 716 is coupled to the valve housing 711, and the valve motor 716 is coupled to the rotation axis 715*b* of the valve disk 715 to rotate the valve disk 715.

The controller 10 may control the steam valve 710 by controlling an operation of the valve motor 716.

The valve disk 715 rotates by the operation of the valve motor 716, and the valve disk 715 opens or closes a flow path inside the steam valve 710 (inside the valve housing 711) depending on the degree of rotation of the valve disk 715.

In one embodiment, depending on the degree of rotation of the valve disk 715, when the valve inlet 712 and the first valve outlet 713 communicate with each other through the valve hole 715*a*, the valve inlet 712 and the second valve outlet 714 are blocked from communicating with each other by the valve disk 715, or when the valve inlet 712 and the second valve outlet 714 communicate with each other through the valve hole 715*a*, the valve outlet 712 and the first valve outlet 713 may be blocked from communicating with each other by the valve disk 715.

In another embodiment, depending on the degree of rotation of the valve disk 715, the valve inlet 712 may communicate with both the first valve outlet 713 and the second valve outlet 714, or the valve inlet 712 may be blocked from communicating with both the first valve outlet 713 and the second valve outlet 714.

In the shoes care device 1 according to one embodiment of the present invention, the valve disk 715 may close a flow path of the second valve outlet 714 while opening a flow path of the first valve outlet 713, and may also close the flow path of the first valve outlet 713 and open the flow path of the second valve outlet 714.

The steam valve 710 made as described above may operate such that only the valve inlet 712 and the first valve outlet 713 communicate with each other, or only the valve inlet 712 and the second valve outlet 714 communicate with each other.

In the arrangement explained above, all the steam generated by the steam generator 700 may be supplied to the accommodation space 101 of the first management device 2*a*, or may be supplied to the accommodation space 101 of the second management device 2*b*. In this case, the steam generated by the steam generator 700 may be supplied to the accommodation space 101 of the first management device 2*a* or the accommodation space 101 of the second management device 2*b* without a pressure drop, and even when only one steam generator 700 is provided in the shoes care device 1, the steam may be sufficiently and stably supplied to the accommodation spaces 101 of each of the two inner cabinets 100.

In one embodiment of the present invention, the controller 10 may control the stream valve 710 such that when the heating part 320 of the first management device 2*a* is turned off (when a heater 321 of the heating part 320 is turned off), the valve disk 715 closes or opens the first valve outlet 713, and when the heating part 320 of the first management device 2*a* is turned on (when the heater 321 of the heating part 320 is turned on), the valve disk 715 closes the first valve outlet 713.

In addition, the controller 10 may control the stream valve 710 such that when the heating part 320 of the second management device 2*b* is turned off (when the heater 321 of the heating part 320 is turned off), the valve disk 715 closes or opens the second valve outlet 714, and when the heating part 320 of the second management device 2*b* is turned on (when the heater 321 of the heating part 320 is turned on), the valve disk 715 closes the second valve outlet 714.

In the shoes care device 1 according to one embodiment of the present invention, by controlling the steam valve 710 by the controller 10, the steam generated in the steam generator 700 may be selectively or simultaneously supplied to the accommodation space 101 of the first management device 2*a* and the accommodation space 101 of the second management device 2*b*, and whether the steam is supplied or not may be controlled according to a use state of the shoes care device 1.

FIG. 8*a* is a cross-sectional view taken along line 8*a*-8*a*' of the shoes care device 1 illustrated in FIG. 3.

FIG. 8*b* is a view illustrating a state in which the main shelf 40 is removed from the shoes care device 1 illustrated in FIG. 8*a*.

FIG. 9 is a cross-sectional view taken along line 9-9' of the shoes care device 1 illustrated in FIG. 3.

Figure 10A:
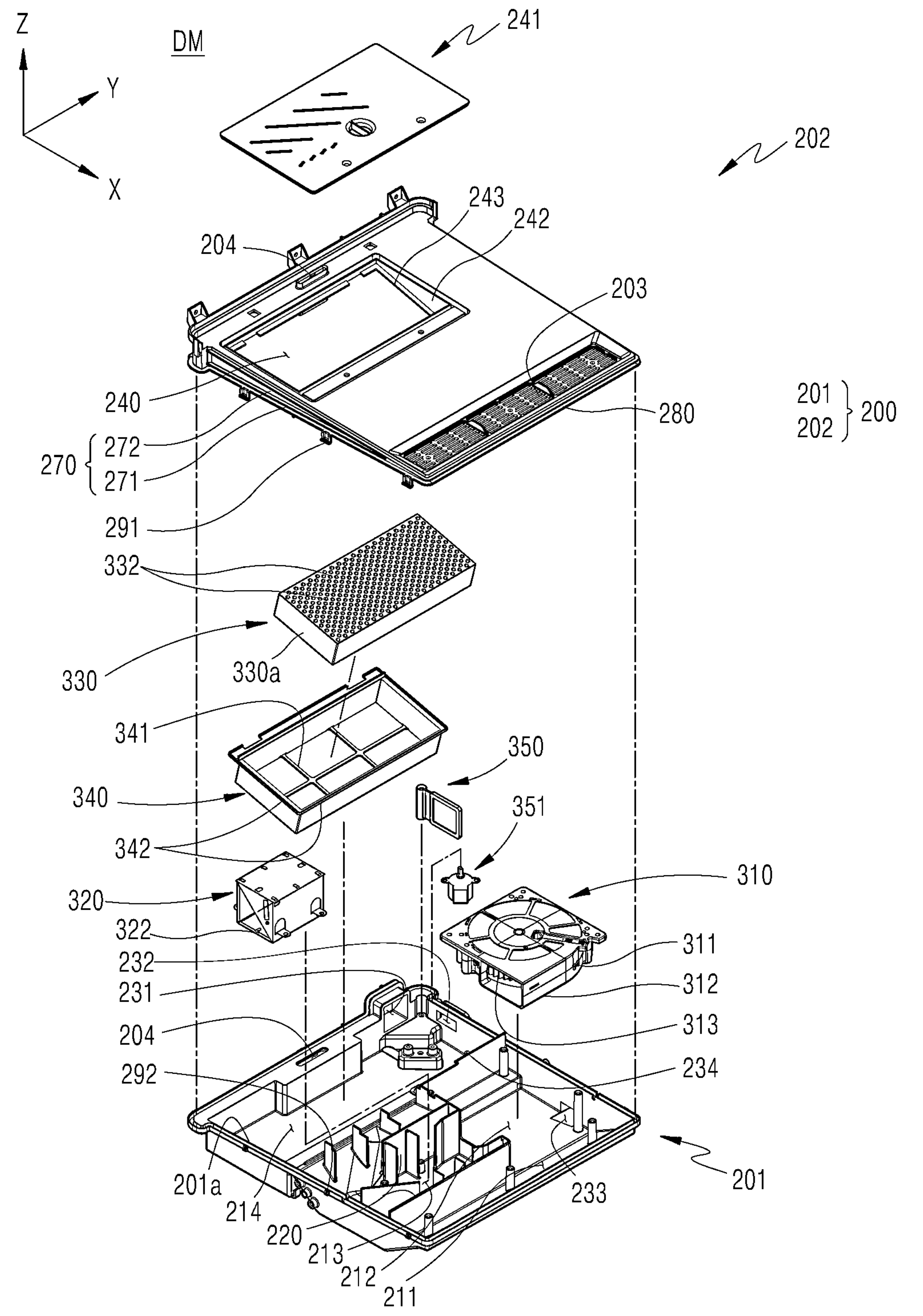
FIG. 10*a* is an exploded perspective view illustrating a drying module in the shoes care device according to one embodiment of the present invention.
Figure 10B:
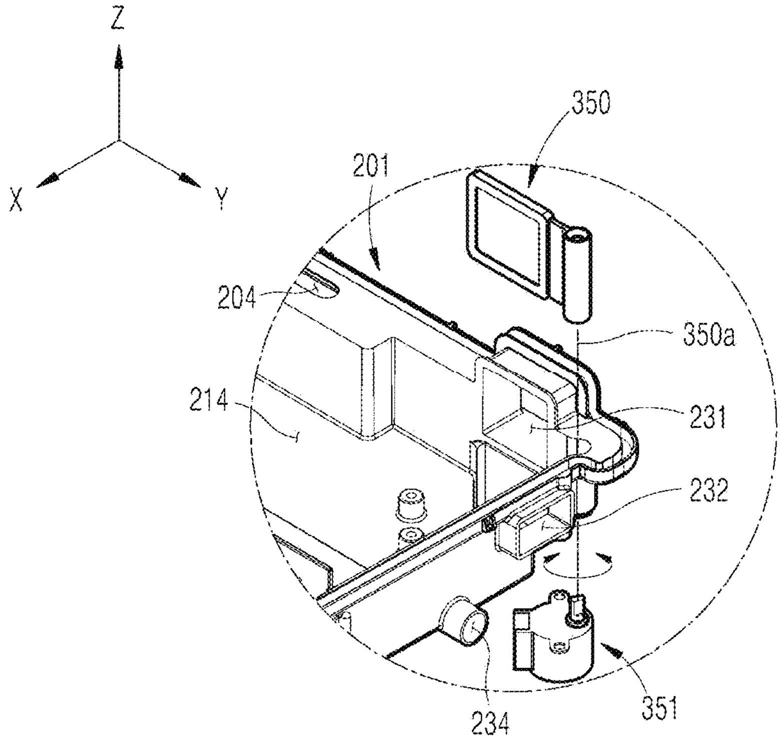
FIG. 10*b* is an exploded perspective view illustrating a partial configuration of the drying module at a part to which a damper is coupled.

FIG. 10*a* is an exploded perspective view illustrating a drying module in the shoes care device 1 according to one embodiment of the present invention. FIG. 10*b* is an exploded perspective view illustrating a partial configuration of the drying module at a part to which the damper 350 is coupled.

In the shoes care device 1 according to one embodiment of the present invention, the dehumidifying part 330 may be used as a means that dehumidifies air.

As described above, the dehumidifying part 330 may be provided inside the module housing 200.

The dehumidifying part 330 is configured to have a predetermined volume. The dehumidifying part 330 may be configured to be porous by itself. A plurality of pores may be formed over an entire volume of the dehumidifying part 330, and air may move by penetrating the dehumidifying part 330 through such pores.

When the dehumidifying part 330 is composed of a combination of a plurality of dehumidifying materials, the plurality of dehumidifying materials may be fixed to each other by a separate fixing means, or may be fixed to each other by adhesion.

The dehumidifying part 330 may be formed of dehumidifying materials, and may be configured to include the dehumidifying materials.

The dehumidifying material 331 according to one embodiment of the present invention is configured to include a material capable of reducing humidity by absorbing moisture in the air. The dehumidifying material 331 may be formed of various materials or a combination of the materials within the range of absorbing or adhering the moisture in the air, and may be formed in various shapes and structures.

The dehumidifying material 331 according to one embodiment of the present invention may be referred to as a desiccant or an adsorbent.

The dehumidifying material 331 according to one embodiment of the present invention may be formed of a microporous material. The dehumidifying material 331 according to one embodiment of the present invention may include silica gel, activated carbon, activated alumina (AL2O3), diatomaceous earth, etc.

Specifically, the dehumidifying material 331 according to one embodiment of the present invention may be formed of zeolite or may be configured to include zeolite.

The zeolite is a natural and synthetic silicate mineral in which tunnels or open channels having a size of approximately 3 to 10 angstroms (Å) are regularly arranged, and may function as dehumidification by adsorbing the moisture in the air.

When the zeolite is heated, moisture adsorbed on the zeolite may be separated into a large amount of steam. According to the characteristics of the zeolite, the zeolite may be regenerated in a state capable of not only performing the dehumidification function to remove the moisture from the air but also performing the dehumidification function by heating the zeolite and separating the moisture adsorbed to the zeolite.

The zeolite may be formed in the form of small grains (or stones) having the size (diameter) of several micrometers to several tens of micrometers, and the dehumidifying material 331 described in one embodiment of the present invention may refer to a combination of the grains (or stones). Each of the grains (or stones) may be agglomerated or combined with each other to form a single structure.

In another embodiment, the dehumidifying part 330 may include a dehumidifying body 330*a* and the dehumidifying material 331.

The dehumidifying body 330*a* may be formed to have a predetermined volume. In one embodiment, the dehumidifying body 330*a* may be formed in a substantially hexahedral shape.

In order to allow air to move through the dehumidifying body 330*a*, the dehumidifying body 330*a* may be provided with a plurality of dehumidification through holes 332 penetrated in one direction. A cross section of the dehumidifying through hole 332 may be formed in a circular shape, a polygonal shape, etc. The dehumidifying through hole 332 may have a hexagonal cross section.

In the dehumidifying body 330*a*, the dehumidifying through hole 332 may all have the same shape and size, or may have different shapes and sizes.

The dehumidifying body 330*a* may be formed of or include materials such as synthetic resin, metal, ceramic, etc. The dehumidifying body 330*a* may be formed of a combination of fibers, and may be formed of a nonwoven fabric, etc.

The dehumidifying material 331 may be coated on the dehumidifying body 330*a*. The dehumidifying material 331 may be coated on the outside and inside of the dehumidifying body 330*a*. Specifically, the dehumidifying material 331 may be coated on a surface in which the dehumidifying through hole 332 is formed.

When the dehumidifying body 330*a* is formed of a combination of fibers, the zeolite may be first coated on each fiber as the dehumidifying material 331, and the zeolite-coated fiber may be processed to form the dehumidifying body 330*a* and simultaneously form the dehumidifying part 330.

Regarding the coating of the zeolite, a manufacturing method of a zeolite coated ceramic paper (Korean Patent No. 10-1004826) is known, and Korean Patent No. 10-1173213 and Korean Patent No. 10-0941521 also describes a method of coating zeolite on a surface of a material. The dehumidifying part 330 according to one embodiment of the present invention may be formed by coating the gelled zeolite precursor on the dehumidifying body 330*a* or materials constituting the dehumidifying body 330*a* and then performing heat treatment when the dehumidifying material 331 is formed of the zeolite.

In one embodiment of the present invention, the coating of the dehumidifying material 331 (zeolite) may be performed by using various known or possible methods, and is not limited to a certain manufacturing method related to the coating of the dehumidifying material 331.

The blowing part 310 is provided inside the connection path F10. A blowing fan 313 may be provided inside the blowing part 310. Since the blowing part 310 is provided in the connection path F10, air flows in the connection path F10 when the blowing part 310 is driven, and since the connection path F10 also communicates with the accommodation space 101 of the inner cabinet 100, the air flows and moves in the accommodation space 101 by driving the blowing part 310.

In this way, the air may be sucked from the inner cabinet 100 into the connection path F10 by the driving of the blowing part 310 (a rotation of the blowing fan 313), and the air inside the connection path F10 may be ventilated.

In one embodiment, the blowing part 310 is provided inside the module housing 200 forming the connection path F10, and the blowing part 310 is driven to suction the air inside the inner cabinet 100 into an inlet 203. The air inside the connection path F10 passes through the module housing 200 constituting the connection path F10, the dry air duct 370, and a nozzle duct 810 and is then discharged back into the inner cabinet 820.

As such, the flow of air may be generated in the shoes care device 1 by the driving of the blowing part 310.

Dry air may be supplied to the inside of the inner cabinet 100 by the blowing part 310.

The heating part 320 is provided at one side of the dehumidifying part 330 and the blowing part 310 in the connection path F10. The heating part 320 may be provided inside the module housing 200. Based on a movement direction of the air inside the module housing 200, the module housing 200 may be arranged in an order of the blowing part 310, the heating part 320, and the dehumidifying part 330. That is, the air introduced into the outlet 203 of the module housing 200 moves along the connection path F10 by passing sequentially through the blowing part 310, the heating part 320, and the dehumidifying part 330.

The heating part 320 is disposed inside the module housing 200 and is configured to heat the air of the module chamber 210 inside the module housing 200.

The heating part 320 may be configured to heat the dehumidifying part 330. The heating part 320 may be configured to heat the dehumidifying material 331 constituting the dehumidifying part 330.

The air heated by the heating part 320 by the driving of the blowing part 310 moves directly to the dehumidifying part 330, thus heating the dehumidifying part 330. To this end, the heating part 320 is disposed inside the module housing 200 adjacent to the dehumidifying part 330. Specifically, the heating part 320 is disposed inside the module housing 200 adjacent to the dehumidifying part 330 based on a movement path of the air inside the module housing 200.

In the module housing 200, the dehumidification by the dehumidifying material 331 or the regeneration of the dehumidifying material 331 may be achieved by selectively heating the heating part 320.

The heating part 320 may be fixedly coupled to the module housing 200 in the module housing 200.

The heating part 320 may be made up of various devices and structures within a range capable of heating the air inside the module housing 200 or supplying heat to the dehumidifying part 330.

The heating part 320 may be formed of an electric heater 321. In one embodiment of the present invention, the heating part 320 may include the heater 321. The heater 321 includes a heating element, and may be configured to supply heat to the periphery while the heating element generates heat by supplied electric energy. The heater 321 may include a nichrome wire as the heating element.

The heater 321 of the heating part 320 may be formed in a ring shape, and the air may move by penetrating the center and surroundings of the ring-shaped heater 321 and be simultaneously heated. The heater 321 of the heating part 320 may be repeatedly formed in a second module chamber 213 along the movement direction of air.

The heater 321 of the heating part 320 may be formed in a circular ring shape or a rectangular ring shape.

The heating part 320 may include a heater flange 322 to which the heater 321 is fixed.

The heater flange 322 may be formed in the form of a metallic plate.

The heater flange 322 may be formed of a combination of flat plates in the second module chamber 213 along the movement direction of air. The heater flange 322 has a cross section that may be formed of a plate shape or a combination of plates in the second module chamber 213 along the movement direction of air (the second direction (Y direction)).

The heater flange 322 may include an outer flange 322*a* and an inner flange 322*b*.

The outer flange 322*a* may be formed in a tubular shape along the second direction (Y direction). An interior of the outer flange 322*a* is provided with a space to move air along the movement direction of air (a direction parallel to the second direction (Y direction)) in the second module chamber 213.

The inner flange 322*b* is fixed to the interior of the outer flange 322*a*. The inner flange 322*b* may include two or more plates crossing each other, and the heater 321 of the heating part 320 may be fixed to the inner flange 322*b*.

The heater flange 322 may be formed in various forms that fix the heater 321 of the heating part 320 and do not interfere with a flow of air moving through the second module chamber 213.

In one embodiment of the present invention, the blowing part 310, the heating part 320, the dehumidifying part 330, and the module housing 200 may form one set.

The set may be provided in a plural form. The shoes care device 1 according to one embodiment may be provided with two sets.

Such a set may be provided in each of the first management device 2*a* and the second management device 2*b*.

Such a set may form a drying module DM in the shoes care device 1 according to one embodiment of the present invention.

That is, in one embodiment of the present invention, the drying module DM may include the module housing 200, the blowing part 310, the heating part 320, and the dehumidifying part 330. Furthermore, the drying module DM is provided in each of the first management device 2*a* and the second management device 2*b*.

In the shoes care device 1 according to one embodiment of the present invention, a plurality of drying modules DM may be provided.

In the shoes care device 1 according to one embodiment of the present invention, a pair of drying modules DM may be provided. When the shoes care device 1 is provided with the pair of drying modules DM, one of the drying modules DM may form a 'drying module A (DM1)' as a drying module of the first management device 2*a*, and the other may form a 'drying module B (DM2)' as a drying module of the second management device 2*b*.

The 'drying module' described in one embodiment of the present invention may be understood to refer to each of the 'drying module A' and the 'drying module B' except as otherwise particularly limited.

In the shoes care device 1 according to one embodiment of the present invention, the drying module A (DM1) and the drying module B (DM2) may operate in different modes. When the drying module A (DM1) operates in a moisture absorption mode, the drying module B (DM2) may operate in a regeneration mode. Conversely, when the drying module A (DM1) operates in the regeneration mode, the drying module B (DM2) may operate in the moisture absorption mode.

The 'moisture absorption mode' described in the present invention means a case in which the dehumidifying part 330 adsorbs moisture in the air, and the 'regeneration mode' means a case in which the moisture adsorbed to the dehumidifying part 330 is separated by heating the dehumidifying part 330.

Naturally, both the drying module A (DM1) and the drying module B (DM2) may operate in the moisture absorption mode or may operate in the regeneration mode.

The module housing 200 may be fixedly coupled to a lower side of the inner cabinet 100. The module housing 200 may be detachably coupled to a lower side of the inner cabinet 100.

The module housing 200 includes the module chamber 210 that is a space having other components accommodated inside. That is, the module chamber 210 is a space inside the module housing 200 distinguished from an external space of the module housing 200. As described above, the module housing 200 forms part of the connection path F10, and accordingly, the module chamber 210 is configured to communicate with a space outside the module housing 200. The module chamber 210 communicates with the accommodation space 101 of the inner cabinet 100.

The module housing 200 may include a module case 201 and a module cover 202.

The module case 201 and the module cover 202 may be formed by injection molding, respectively, and may be assembled with each other after manufacturing to form the module housing 200.

The module case 201 is formed in the form of a container that is concave substantially downwards, and forms the module chamber 210 of the module housing 200.

The module case 201 may be configured in the form of a container opened upwards, and includes a module opening 201*a*.

In a plan view, an area of the module opening 201*a* may be larger than or equal to an area of the module chamber 210.

The module chamber 210 may include a first module chamber 212, a second module chamber 213, and a third module chamber 214. The module chamber 210 may include a suction module chamber 211.

In order to distinguish between the suction module chamber 211, the first module chamber 212, the second module chamber 213, and the third module chamber 214, a module partition wall 220 may be formed inside the module housing 200. Furthermore, the module partition wall 220 guides the movement of air so that air moves in a predetermined direction inside the module housing 200.

The suction module chamber 211 is a first space where air is introduced into the module housing 200.

The first module chamber 212 is a space in which the blowing part 310 is accommodated, the second module chamber 213 is a space in which the heating part 320 is accommodated, and the third module chamber 214 is a space in which the dehumidifying part 330 is accommodated.

In one embodiment of the present invention, the suction module chamber 211, the first module chamber 212, the second module chamber 213, and the third module chamber 214 may be formed at different positions in a plan view.

In addition, the air of the module chamber 210 may be configured to move through the suction module chamber 211, the first module chamber 212, the second module chamber 213, and the third module chamber 214 sequentially. That is, when the blowing part 310 is driven, air moves sequentially through the suction module chamber 211, the first module chamber 212, the second module chamber 213, and the third module chamber 214 inside the module housing 200.

The module case 201 may include a dry air outlet 231 and a wet air outlet 232.

The dry air outlet 231 may be formed in a hole shape opened to allow air in the third module chamber 214 to flow out. The dry air outlet 231 is formed adjacent to the third module chamber 214. The dry air outlet 231 may be formed on one edge of the module case 201. Furthermore, the dry air outlet 231 may be connected to the accommodation space 101 through the dry air duct 370 and the nozzle duct 810.

The wet air outlet 232 may be formed in a hole shape opened to allow the air in the third module chamber 214 to flow out. The wet air outlet 232 is formed adjacent to the third module chamber 214. The wet air outlet 232 may be formed on a frame on one side of the module case 201. Furthermore, the wet air outlet 232 may be connected to the condenser 400.

The dry air outlet 231 and the wet air outlet 232 may be formed adjacent to each other. The dry air outlet 231 and the wet air outlet 232 may be formed adjacent to any one vertex part of the module housing 200.

The suction module chamber 211 is formed adjacent to the first module chamber 212, and a bottom surface of the suction module chamber 211 may be inclined downwardly toward the first module chamber 212. Accordingly, air introduced into the suction module chamber 211 may naturally move toward the first module chamber 212 by hitting the bottom surface of the suction module chamber 211 forming an inclined surface, and a condensed water introduced into the suction module chamber 211 may move along the bottom surface of the suction module chamber 211 forming the inclined surface, and may move to the first module chamber 212.

The blowing part 310 may be assembled to the module housing 200 while being spaced apart from a bottom surface of the first module chamber 212. Furthermore, in this case, the blowing part 310 may be configured such that air may be introduced from a lower side of the first module chamber 212 to an interior of the blowing part 310 inside the first module chamber 212.

The module case 201 may include a first condensed water discharge hole 233.

The first condensed water discharge hole 233 is formed in a hole shape penetrating the module case 201. The first condensed water discharge hole 233 is formed on an edge of the module case 201 adjacent to a condenser 400 and formed to be equal to or lower than the bottom surface of the first module chamber 212, and communicates with the condenser 400. Among the bottom surfaces of the first module chamber 212, the first condensed water discharge hole 233 may form the lowest part, or the bottom surface of the first module chamber 212 may be formed such that a height thereof is lowered toward or at least equal to the first condensed water discharge hole 233.

As such, the first condensed water discharge hole 233 may be lower than the bottom surface of the first module chamber 212, and accordingly, the condensed water introduced into the first condensed water discharge hole 232 may move toward the first condensed water discharge hole 233 and flow into the condenser 400 through the first condensed water discharge hole 233.

Meanwhile, since the first condensed water discharge hole 233 is a hole in which the module housing 200 and the condenser 400 communicate with each other, the air inside the condenser 400 may flow into the module housing 200 through the first condensed water discharge hole 233. The air introduced into the module housing 200 through the first condensed water discharge hole 233 from an interior of the condenser 400 may move along the first module chamber 212, the second module chamber 213, and the third module chamber 214 by an operation of the blowing part 310 and may be introduced again into the condenser 400 and condensed.

The shoes care device 1 according to one embodiment of the present invention includes the condenser 400 coupled to an outer surface of the inner cabinet 100 and forming a regeneration path F20. In a plan view, the first module chamber 212 may be provided between the second module chamber 213 and the condenser 400. Since the first module chamber 212 is disposed between the second module chamber 213 and the condenser 400, a direct heat exchange between the condenser 400 and the heating part 320 is blocked, and the heat may be prevented from being transferred to the condenser 400 when the heating part 320 is heated inside the second module chamber 213.

Accordingly, when the dehumidifying part 330 is regenerated, condensation depending on heating of air by the heater 321 of the heating part 320 and cooling of air inside the condenser 400 may be effective performed.

The dehumidifying part 330 may be coupled to the module housing 200 while being spaced apart from a bottom surface of the third module chamber 214. Furthermore, in this case, the air inside the third module chamber 214 may move downwards through the dehumidifying part 330 from an upper side of the third module chamber 214.

The module case 201 may include a second condensed water discharge hole 234.

The second condensed water discharge hole 234 is formed in a hole shape penetrating the module case 201. The second condensed water discharge hole 234 is formed on the edge of the module case 201 adjacent to the condenser 400 and formed to be equal to or lower than the bottom surface of the third module chamber 214, and communicates with the condenser 400. Among the bottom surfaces of the third module chamber 214, the second condensed water discharge hole 234 may form the lowest part, or the bottom surface of the third module chamber 214 may be formed such that a height thereof is lowered toward or at least equal to the second condensed water discharge hole 234.

The second condensed water discharge hole 234 may be formed adjacent to the wet air outlet 232.

In this way, the second condensed water discharge hole 234 may be lower than the bottom surface of the third module chamber 214, and accordingly, condensed water introduced into the third module chamber 214 may move toward the second condensed water discharge hole 234, and may flow into the condenser 400 through the second condensed water discharge hole 234.

Meanwhile, since the second condensed water discharge hole 234 is a hole in which the module housing 200 and the condenser 400 communicate with each other, the air inside the condenser 400 may flow into the module housing 200 through the second condensed water discharge hole 234. In this way, the air introduced from the interior of the condenser 400 into the module housing 200 through the second condensed water discharge hole 234 moves directly to the wet air outlet 232 by the driving of the blowing part 310, and may be introduced again into the condenser 400 and condensed.

The module housing 200 may include the module cover 202.

The module cover 202 is coupled to the module case 201 while shielding the module opening 201*a* from an upper side of the module case 201. The module cover 202 may be detachably coupled to the module case 201. A plurality of locking projections 292 may protrude from one of the module cover 202 and the module case 201, and a plurality of locking grooves 291 into which the locking projections 292 are inserted and locked may be formed on the other. The locking projections 292 and locking grooves 291 are provided in a plural form, respectively, and may be spaced apart along an edge of the module housing 200 and repeatedly formed.

With the blowing part 310, the heating part 320, and the dehumidifying part 330 accommodated in the module case 201, the module cover 202 may shield the blowing part 310, the heating part 320, and the dehumidifying part 330 and may be coupled to the module case 201.

The shoes care device according to one embodiment of the present invention may be formed in a structure in which the dehumidifying part 330 may be detachable from the module housing 200. The structure of the shoes care device provides an advantage in maintaining and managing the dehumidifying part 330 and the shoes care device 1 on the whole.

On the other hand, the dehumidifying part 330 may be repeatedly used by regeneration, but with the repeated use, the dehumidifying part 330 needs to be replaced.

Considering these descriptions, the shoes care device 1 according to one specific embodiment of the present invention may be configured to separate and replace the dehumidifying part 330.

In one embodiment of the present invention, the module cover 202 of the module housing 200 may form a bottom surface of the inner cabinet 100.

The module cover 202 may form a boundary surface between the inner cabinet 100 and the module housing 200. The module cover 202 may be formed in a substantially rectangular shape.

The module cover 202 may be configured in substantially parallel with the horizontal direction.

Alternatively, the module cover 202 may be inclined to any one side. In one embodiment, an upper surface of the module cover 202 may be inclined downwardly toward the first direction (X direction) (a front side of the shoes care device 1).

In one embodiment of the present invention, the main shelf 40 is mounted in close contact with an upper side surface of the module cover 202, and the main shelf 40 mounted on the upper side surface of the module cover 202 is also configured to be inclined when the upper side surface of the module cover 202 is inclined. In this case, since an upper surface of the main shelf 40 is inclined, water (e.g., condensed water) placed on the upper surface of the main shelf 40 may flow along an inclined direction.

The shoes care device 1 may include a dehumidifying material cover 241.

The dehumidifying material cover 241 forms part of the module cover 202 that is the bottom of the inner cabinet 100. Furthermore, the dehumidifying material cover 241 may be detached from the module cover 202 of the inner cabinet 100 or may be hinge-coupled to the module cover 202.

In the module cover 202, a dehumidifying material exit 240 which is an opening of a shape and a size corresponding to the dehumidifying material cover 241 may be formed. The dehumidifying material cover 241 may be configured to open and close the dehumidifying material exit 240. The dehumidifying material cover 241 may be tightly coupled to the dehumidifying material exit 240. At least a part of the dehumidifying material cover 241 may be separated from the module cover 202. In one embodiment, the dehumidifying material exit 240 of the module cover 202 may be opened while completely separating the dehumidifying material cover 241 from the module cover 202, and in another embodiment, the dehumidifying material cover 241 of the module cover 202 may be opened while rotating the dehumidifying material cover 241 around a hinge axis. The dehumidifying part 330 may be introduced into or withdrawn from the module housing 200 through the dehumidifying material exit 240.

The dehumidifying material exit 240 and the dehumidifying material cover 241 may be formed in a position corresponding to the third module chamber 214 in a plan view. That is, the dehumidifying material exit 240 and the dehumidifying material cover 241 may be formed directly above the third module chamber 214. The shoes care device 1 according to one embodiment of the present invention may be configured such that the first module chamber 212 and the second module chamber 213 are not exposed in a plan view in a state where the dehumidifier cover 241 is opened.

When the dehumidifying material cover 241 is opened in the module cover 202, the third module chamber 214 disposed on a lower part of the module cover 202 is exposed through the dehumidifying material exit 240 of the module cover 202, and the dehumidifying part 330 may be settled inside the module case 201, or may be immediately withdrawn and separated from the module case 201.

The sizes and shapes of the dehumidifying material cover 241 and the dehumidifying material exit 240 are variously provided within the range capable of withdrawing or inserting the dehumidifying part 330.

The dehumidifying material cover 241 may be formed in a rectangular plate shape.

The length of the dehumidifying material cover 241 in the first direction (X direction) may be equal to or longer than the length of the dehumidifying part 330, and the length of the dehumidifying material cover 241 in the second direction (Y direction) may be equal to or longer than the length of the dehumidifying part 330.

As described above, in the shoes care device 1 according to one embodiment of the present invention, the heating part 320 and the dehumidifying part 330 are formed at different positions in a top plane view, and when the dehumidifying material cover 241 is opened on the module cover 202 that forms the bottom surface of the inner cabinet 100, the dehumidifying part 330 disposed directly below the dehumidifying material cover 241 may be withdrawn from the module housing 200, and the dehumidifying part 330 may be easily replaced by the user.

In addition, since only the third module chamber 214 is exposed in a state in which the dehumidifier cover 241 is opened, and the first module chamber 212 and the second module chamber 213 are not exposed, the blowing part 310 accommodated in the first module chamber 212 and the heating part 320 accommodated in the second module chamber 213 are not exposed. That is, since the blowing part 310 and the heating part 320 are not directly exposed to the user, safety accidents due to an unintended operation of the blowing part 310 and/or the heating part 320 can be prevented.

The dehumidifying material cover 241 may be configured to separately shield the dehumidifying part 330. A space between the dehumidifying material cover 241 and the dehumidifying part 330 may form a part of the connection path F10.

As described above, the outlet 203 forms an inlet through which the air inside the inner cabinet 100 is sucked into the module housing 200. The outlet 203 may form a start part of the connection path F10. The outlet 203 may be formed in the shape of a hole vertically penetrated from the bottom surface (the upper surface of the module cover 202) of the inner cabinet 100.

A network such as a grid shape, a mesh shape, etc., may be formed on the outlet 203.

The outlet 203 may be formed parallel to the second direction (Y direction). That is, the outlet 203 may be formed in a long hole shape in the module cover 202 along the second direction (Y direction).

The outlet 203 may be formed on an edge of the module cover 202. The outlet 203 may be formed on the edge of the module cover 202 along the second direction (Y direction).

The outlet 203 may be formed on a front part or a rear part of the module cover 202 based on the first direction (X direction).

The outlet 203 may be disposed relatively close to the door 30 in the module cover 202. That is, the outlet 203 may be disposed relatively in the front of the module cover 202.

The upper surface of the module cover 202 may be inclined downwardly toward the outlet 203. That is, a part of the module cover 202 where the outlet 203 is formed may be configured to be the lowest. Accordingly, when water is present on the module cover 202 or the main shelf 40, such water may flow along the surface of the module cover 202 by gravity and flow into the inlet 203.

In the shoes care device 1 according to one embodiment of the present invention, the module chamber 210 is provided inside the module housing 200, and the module chamber 210 includes a first module chamber 212, a second module chamber 213, and the third module chamber 214. The first module chamber 212, the second module chamber 213, and the third module chamber 214 may be formed at different positions in a plan view. That is, the blowing part 310, the heating part 320, and the dehumidifying part 330 may be disposed at different positions in the module housing 200. According to one embodiment of the present invention, the blowing part 310, the heating part 320, and the dehumidifying part 330, which are main means for drying the air inside the inner cabinet 100 and main means for regenerating the dehumidifying part 330, are disposed together in the module chamber 210 of the module housing 200. Accordingly, the blowing part 310, the heating part 320, and the dehumidifying part 330 are disposed at positions considerably close to each other.

In one embodiment of the present invention, the module case 201 of the module housing 200 may be integrally formed by injection molding. In this case, the bottom parts of the module housing 200 may be integrally formed, the bottom parts may not be assembled with each other, and no gaps may be formed in the bottom parts.

In the arrangement explained above, the condensed water can be effectively prevented from leaking from the module housing 200. In addition, a vertical height of the module housing 200 can be minimized.

When moisture remains at an unintended part inside the shoes care device 1, such moisture may reproduce bacteria or cause odors. This is why there is need for countermeasures to solve the problems, and the shoes care device 1 according to one embodiment of the present invention can effectively prevent water from leaking in consideration of such problems.

In the shoes care device 1 according to one embodiment of the present invention, the air in the module chamber 210 may sequentially move the first module chamber 212, the second module chamber 213, and the third module chamber 214. Accordingly, since the third module chamber 214 and a drying flow path F10*b* may be connected in the shortest distance, which provides excellent drying efficiency by the dehumidifying part 330, and air heated by the heating part 320 moves directly to the dehumidifying part 330 to form the shoes care device 1 with excellent regeneration efficiency.

In the shoes care device 1 according to one embodiment of the present invention, the module housing 200 includes the suction module chamber 211, and the bottom surface of the suction module chamber 211 may be inclined downwardly toward the first module chamber 212. Accordingly, the air introduced through the outlet 203 moves naturally to the first module chamber 212 by hitting the bottom surface of the suction module chamber 211, and the condensed water introduced into the outlet 203 moves to the first module chamber 212 such that the condensed water can be easily drained.

The shoes care device 1 according to one embodiment of the present invention may include the condenser 400, and the module case 201 may include the first condensed water discharge hole 233. In addition, the module case 201 may include the second condensed water discharge hole 234. Accordingly, the dehumidifying part 330 may be effectively regenerated, and condensed water inside the module housing 200 may be easily discharged to the condenser 400.

In the shoes care device 1 according to one embodiment of the present invention, steam generated by the steam generator 700 is supplied to the accommodation space 101 of the inner cabinet 100, and to this end, the shoes care device 1 includes a steam inlet 204.

The steam inlet 204 forms an inlet through which steam is supplied to the accommodation space 101 of the inner cabinet 100.

In the shoes care device according to one embodiment of the present invention, the steam inlet 204 is formed in the module housing 200.

The steam inlet 204 may be formed in a rear part of the module housing 200 based on the first direction (X direction). The steam inlet 204 may be formed to vertically penetrate the module housing 200. The steam inlet 204 may be formed to vertically penetrate the module case 201 and the module cover 202. The steam inlet 204 may be formed in the center in a right-left direction at the rear part of the module housing 200.

The steam inlet 204 may be formed on a rear edge of the module housing 200, and may be formed directly behind a position where the third module chamber 214 is formed. The third module chamber 214 and the steam inlet 204 are shielded from each other.

In the module housing 200, the module cover 202 forms the bottom surface of the accommodation space 101, and when the module housing 200 is coupled to the inner cabinet 100, the steam inlet 204 is formed behind the bottom of the inner cabinet 100.

The steam generator 700 and the steam valve 710 are disposed in a lower part, the distance from the steam generator 710 to the steam inlet 204 can be reduced by forming the module housing 200, and the steam inlet 204 in a rear part of the module housing 200, and an increase in the load required for the supply of steam can be prevented. Accordingly, steam may be smoothly supplied from the steam generator 700 to the steam inlet 204.

Figure 11:
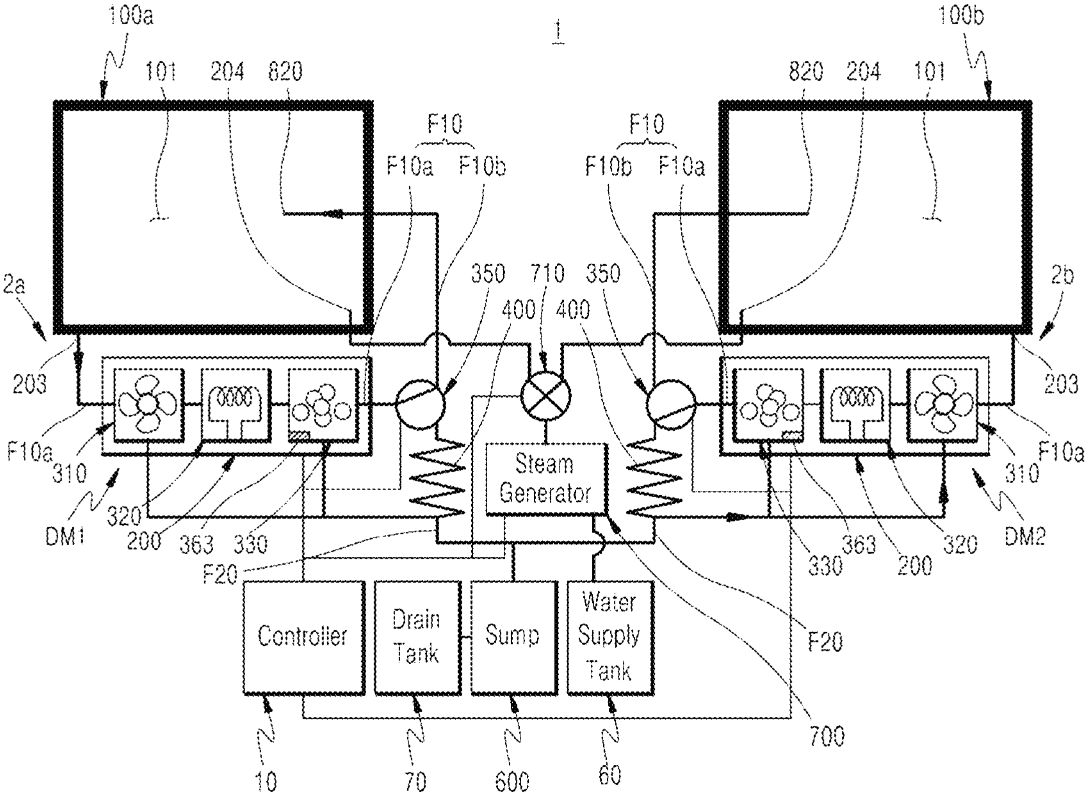
FIG. 11 is a diagram illustrating a connection relationship between components and a flow of fluid in the shoes care device according to one embodiment of the present invention.

FIG. 11 is a diagram illustrating a connection relationship between components and a flow of fluid in the shoes care device 1 according to one embodiment of the present invention.

The connection path F10 forms a movement path of air connected from the outlet 203 to the nozzle 820. That is, the outlet 203 may form an inlet of the connection path F10, and the nozzle 820 may form an outlet of the connection path F10.

The outlet 203 may be coupled to communicate with the inner cabinet 100, and the nozzle 820 may be provided inside the inner cabinet 100. Except the outlet 203 and the nozzle 820, one part of the connection path F10 may be provided inside the inner cabinet 100, and the other part may be provided outside the inner cabinet 100.

The air inside the inner cabinet 100 moves to the connection path F10 through the outlet 203, and the air passing through the connection path F10 moves back into the inner cabinet 100 through the nozzle 820. As such air flow is repeated, the air circulation is performed in the shoes care device 1.

In the nozzle 820, a hole through which air is discharged is formed in the accommodation space 101 of the inner cabinet 100, and the nozzle 820 may form a last part of the connection path F10.

In the shoes care device 1 according to one embodiment of the present invention, since the nozzle 820 is configured to be movable to various positions inside the inner cabinet 100, the shoes may be managed in various positions.

As described above, the dehumidifying part 330 is disposed in the connection path F10. The air moving through the connection path F10 passes through the dehumidifying part 330, and the dehumidifying part 330 absorbs moisture from the air moving through the connection path F10 such that the air from which moisture has been removed may be supplied into the inner cabinet 100.

The connection path F10 may be divided into a conversion flow path F10*a* and a drying flow path F10*b*. The conversion flow path F10*a* and the drying flow path F10*b* form a movement path of air sequentially connected to each other. The air in the connection path F10 may sequentially move through the conversion flow path F10*a* and the drying flow path F10*b*.

The conversion flow path F10*a* forms an upstream section of the connection path F10, which is connected to the outlet 203. The conversion flow path F10*a* may be a section in which the blowing part 310, the heating part 320, and the dehumidifying part 330 are disposed. The conversion flow path F10*a* may be formed by the module housing 200, and the module chamber 210 inside the module housing 200 may form the conversion flow path F10*a*.

The conversion flow path F10*a* may be a section in which humid air moves and dries. The conversion flow path F10*a* may be a section in which air is dehumidified by the dehumidifying part 330.

Meanwhile, the conversion flow path F10*a* may be a section in which the dehumidifying part 330 (the dehumidifying material 331) are regenerated.

The drying flow path F10*b* forms a downstream section of the connection path F10, which connects the conversion flow path F10*a* to the nozzle 820. A flow path formed by the drying air duct 370, the nozzle duct 810, and the nozzle 820 may form the drying flow path F10*b*.

The drying passage F10*b* may be a section in which dry air with moisture removed therefrom moves.

When the drying module DM operates in the moisture absorption mode, the drying flow path F10*b* communicates with the conversion flow path F10*a*, and when the drying module DM operates in the regeneration mode, the drying flow path F10*b* and the conversion flow path F10*a* may not communicate with each other such that the drying flow path F10*b* and the conversion flow path F10*a* block each other.

Accordingly, when air is dehumidified by the dehumidifying part 330 in the conversion flow path F10*a*, the dried air moves through the drying flow path F10*b*.

The dry air duct 370 may be fixedly coupled to an outer wall surface of the inner cabinet 100, and the nozzle duct 810 may be provided inside the inner cabinet 100.

As the dry air duct 370 is tightly coupled to an inner rear plate 110 of the inner cabinet 100, a flow path may be formed between the dry air duct 370 and the inner cabinet 100 (the inner rear plate 110), and such a flow path may form a part of the drying flow path F10*b*. A lower part of the dry air duct 370 communicates with the dry air outlet 231 of the module housing 200, an upper part thereof communicates with the nozzle duct 810, which connect the interior of the module housing 200 and the interior of the nozzle duct 810 for mutual communication.

As described above, after humid air in the accommodation space 101 of the inner cabinet 100 flows into the conversion flow path F10*a*, the air is dehumidified by the dehumidifying part 330 and converted into dry air, and the dry air can be resupplied to the accommodation space 101 of the inner cabinet 100 through the drying flow path F10*b*.

The regeneration path F20 forms a movement path of a fluid.

The regeneration path F20 forms a passage through which air and/or condensed water inside the shoes care device moves.

The regeneration path F20 forms a path through which air and/or condensed water passing through the dehumidifying part 330 moves when the dehumidifying material 331 is regenerated. The regeneration path F20 may be entirely or partially formed of a pipe, a hose, a tube, a duct, a housing, or a combination thereof.

Moisture generated during the regeneration process of the dehumidifying material 331 needs to be discharged through a separate flow path separated from the drying flow path F10*b*, which is a flow path through which dry air moves. Accordingly, the shoes care device 1 according to one embodiment of the present invention includes the regeneration path F20, and when the dehumidifying material 331 is regenerated, air passing through the dehumidifying part 330 is not ventilated to the nozzle 820 but moves through the regeneration path F20.

The regeneration path F20 is a flow path branched from the connection path F10. The regeneration path F20 may be branched from the connection path F10 to form a path different from that of the drying flow path F10*b* of the connection path F10. The regeneration path F20 is connected to the sump 600.

The regeneration path F20 may be a section that connects the conversion flow path F10*a* and the sump 600.

The regeneration path F20 may be a section in which humid air separated from the dehumidifying part 330 moves.

The condenser 400 according to one embodiment of the present invention forms a regeneration path F20. Moisture separated from the dehumidifying material 331 may be condensed after moving to the condenser 400 along with air moving along the regeneration path F20. In addition, condensed water condensed in the condenser 400 may be moved to the sump 600 through the regeneration path F20, collected from a lower part of the sump 600, and then discharged to the drain tank 70, discharged to the outside, or pressed to the steam generator 700.

In the shoes care device 1 according to one embodiment of the present invention, when the drying module DM operates in the regeneration mode, the regeneration path F20 communicates with the conversion flow path F10*a*, and when the drying module DM operates in the moisture absorption mode, the regeneration path F20 and the conversion flow path F10 may not communicate with each other such that the regeneration path F20 and the conversion flow path F10 block each other.

Accordingly, when the dehumidifying part 330 is regenerated in the conversion flow path F10*a*, humid air containing moisture separated from the dehumidifying part 330 moves through the regeneration path F20.

In one embodiment of the present invention, the damper 350 may be formed in the form of a damper valve.

The damper 350 may be rotatably coupled to the module housing 200. The damper 350 may be coupled to the module housing 200 in a form accommodated in the module housing 200.

As described above, in the module housing 200, the dry air outlet 231 forming an inlet of the drying flow path F10*b* is formed as a passage of the connection path F10, and the wet air outlet 232 forming an inlet of the regeneration path F20 is formed.

The damper 350 controls a movement path of air passing through the dehumidifying material 331 in the module housing 200. Depending on the operation of the damper 350, the air passing through the dehumidifying material 331 may move into the inner cabinet 100 through the nozzle 820 or may move into the regeneration path F20.

The damper 350 may be configured to open the regeneration path F20 while blocking the drying flow path F10*b*, or to open the drying flow path F10*b* while blocking the regeneration path F20.

The damper 350 may be configured to selectively shield the dry air outlet 231 and the wet air outlet 232. The damper 350 may be configured to selectively seal the dry air outlet 231 and the wet air outlet 232.

The damper 350 may selectively block one of the dry air outlet 231 and the wet air outlet 232. When the damper 350 opens the dry air outlet 231 while blocking the wet air outlet 232, the air passing through the dehumidifying material 331 may move into the inner cabinet 100 through the nozzle 820, and when the damper 350 opens the wet air outlet 232 while blocking the dry air outlet 231, the air passing through the dehumidifying material 331 may be condensed while moving through the regeneration path F20.

In the shoes care device 1 according to one embodiment of the present invention, the damper 350 may be configured to be hinge-rotatable around a hinge axis 350*a* formed on one side. The hinge axis 350*a* of the damper 350 may be parallel to the third direction (Z direction). In addition, the shoes care device 1 may include a damper motor 351 configured to rotate the damper 350 around the hinge axis 350*a* of the damper 350. The damper motor 351 may be formed as an electric motor and may be configured to rotate the damper 350 bidirectionally.

When the damper 350 opens the dry air outlet 231 and seals the wet air outlet 232, the air inside the inner cabinet 100 moves along the connection path F10 and is circulated by sequentially passing through the inlet 203, the module housing 200 (the blowing part 310 and the dehumidifying part 330, the dry air outlet 231, the dry air duct 370, the nozzle duct 810, and the nozzle 820.

When the damper 350 seals the dry air outlet 231 and opens the wet air outlet 232, the air moves along the conversion flow path F10*a* and the regeneration path F20 and is circulated by sequentially passing through the module housing 200 (the blowing part 310, the heating part 310, and the dehumidifying part 330), the wet air outlet 232, and the condenser 400.

In one embodiment of the present invention, the controller 10 may control the damper motor 351 such that the damper 350 closes the dry air outlet 231 and opens the wet air outlet 232 when the heating part 320 is turned on. In addition, the controller 10 may control the damper motor 351 such that the damper 350 opens the dry air outlet 231 and closes the wet air outlet 232 when the heating part 320 is turned off.

Accordingly, by controlling the damper motor 351 by the controller 10, the damper 350 may open the drying flow path F10*b* and close the regeneration path F20 when the heating part 320 is turned off, and may close the drying flow path F10*b* and open the regeneration path F20 when the heating part 320 is turned on.

The damper motor 351 may be controlled individually in each of the first management device 2*a* and the second management device 2*b*.

Referring to FIG. 11, in the drying module A (DM1) of the first management device 2*a*, the damper 350 seals the wet air outlet 232 and opens the dry air outlet 231 of the second management device 2*b*, and in the drying module B (DM2) of the second management device 2*b*, when the damper 350 opens the wet air outlet 232 and seals the dry air outlet 231, the air in the conversion flow path F10*a* of the first management device 2*a* may flow through the drying flow path F10*b*, and the air in the conversion flow path F10*a* of the second management device 2*b* may flow through the regeneration path F20. Furthermore, in this case, the drying module A (DM1) of the first management device 2*a* may operate in the moisture absorption mode, and the drying module B (DM2) of the second management device 2*b* may operate in the regeneration mode.

In contrast, when in the drying module A (DM1) of the first management device 2*a*, the damper 350 opens the wet air outlet 232 and seals the dry air outlet 231, and in the drying module B (DM2) of the second management device 2*b*, the damper 350 seals the wet air outlet 232 and opens the dry air outlet 231, the air in the conversion flow path F10*a* of the first management device 2*a* may flow along the regeneration path F20, and the air in the conversion flow path F10*a* of the second management device 2*b* may flow along the drying flow path F10*b*. Furthermore, in this case, the drying module A (DM1) of the first management device 2*a* may operate in the regeneration mode, and the drying module B (DM2) of the second management device 2*b* may operate in the moisture absorption mode.

In both the drying module A (DM1) of the first management device 2*a* and the drying module B (DM2) of the second management device 2*b*, when the damper 350 seals the wet air outlet 232 and opens the dry air outlet 231, both the drying module A (DM1) and the drying module B (DM2) may operate in the moisture absorption mode.

In both the drying module A (DM1) of the first management device 2*a* and the drying module B (DM2) of the second management device 2*b*, when the damper 350 seals the dry air outlet 231 and opens the wet air outlet 232, both the drying module A (DM1) and the drying module B (DM2) may operate in the regeneration mode.

In the shoes care device 1 according to one embodiment of the present invention, the first management device 2*a* and the second management device 2*b* individually include the inner cabinet 100, the connection path F10, the blowing part 310, and the dehumidifying part 330. In addition, the shoes care device 1 includes the steam generator 700 and the steam valve 710. Accordingly, the degree of the supply of steam, the degree of dehumidification by the dehumidifying part 330, and the flow of air circulated along the connection path F10 may be different in each of the first management device 2*a* and the second management device 2*b*, and the first management device 2*a* and the second management device 2*b* may manage shoes under different conditions.

In addition, the first management device 2*a* and the second management device 2*b* include the module housing 200, the blowing part 310, the heating part 320, the dehumidifying part 330, and the drying flow path F10*b*, respectively. The air and condensed water moving in the first management device 2*a* and the air and condensed water moving in the second management device 2*b* move along different paths, thereby achieving accurate control intended in each of the first management device 2*a* and the second management device 2*b*. In this case, since the first management device 2*a* and the second management device 2*b* share and use the steam generator 700, the steam generator 700 can be efficiently utilized in the shoes care device 1, and the shoes care device 1 can efficiently utilize the space.

In addition, as described above, when the shoes are dried in one of the first management device 2*a* and the second management device 2*b*, the dehumidifying part 330 may be regenerated in the other, and the efficient management of the shoes and efficient use of the shoes care device 1 can be achieved.

In the shoes care device 1 according to one embodiment of the present invention, the first management device 2*a* and the second management device 2*b* each include the regeneration path F20 and the damper 350 individually.

The controller 10 may control the heating part 320 (the heater 321) and the damper 350 to interwork with each other.

The controller 10 may control the damper 350 to open the drying flow path F10*b* and close the regeneration path F20 when the heating part 320 is turned off, and may control the damper 350 to close the drying flow path F10*b* and open the regeneration path F20 when the heating part 320 is turned on.

The controller 10 may control each component of the shoes care device 1 such that air flowing into the module chamber 210 from the accommodation space 101 and passing through the dehumidifying part 330 moves along the drying flow path F10*b* when the heating part 320 is turned off (when the heater 321 of the heating part 320 is turned off), and the air moves along the regeneration path F20 when the heating part 320 is turned on (when the heater 321 of the heating part 320 is turned on).

Such control may be performed individually in each of the first management device 2*a* and the second management device 2*b*. Accordingly, since the movement path of air inside the module chamber 210 is changed depending on an operation of the heating part 320, the drying of the shoes and the regeneration of the dehumidifying part 330 can be effectively achieved.

The controller 10 may control the steam valve 710 and the heating part 320 to interwork with each other.

The controller 10 may control the steam valve 710 such that when the heating part 320 of the first management device 2*a* is turned off, the valve disk 715 closes or opens the first valve outlet 713, when the heating part 320 of the first management device 2*a* is turned on, the valve disk 715 closes the first valve outlet 713, when the heating part 320 of the second management device 2*b* is turned off, the valve disk 715 closes or opens the second valve outlet 714, and when the heating part 320 of the second management device 2*b* is turned on, the valve disk 715 closes the second valve outlet 714.

In this way, the supply of steam to the accommodation space 101 of the inner cabinet 100 and the operation of the heating part 320 inside the module housing 200 may interwork with each other to effectively perform the drying of the shoes and the regeneration of the dehumidifying part 330.

The shoes care device 1 according to one embodiment of the present invention may include a first sensor 361 and a second sensor 362 (see FIG. 9).

The first sensor 361 may be installed in the second module chamber 213 of the module housing 200, and the second sensor 362 may be installed in the third module chamber 214 of the module housing 200. The first sensor 361 may be configured to measure the temperature and/or humidity of the second module chamber 213, and the second sensor 362 may measure the temperature and/or humidity of the third module chamber 214.

The first sensor 361 measures the temperature and/or humidity of air before passing through the dehumidifying part 330, and the second sensor 362 measures the temperature and/or humidity of air after passing through the dehumidifying part 330.

The controller 10 may compare the temperature and/or humidity of the second module chamber 213 measured by the first sensor 361 with the temperature and/or humidity of the third module chamber 214 measured by the second sensor 362 to recognize a state and a change of the temperature and/or humidity inside the module housing, and may also check an operation state of the drying module DM.

The controller 10 may recognize the temperature and humidity of the second module chamber 213 measured by the first sensor 361, and the temperature and humidity of the third module chamber 214 measured by the second sensor 362 to recognize a change in the humidity inside the module housing 200. Accordingly, the degree of dehumidification by the dehumidifying part 330 may be checked, and the degree of regeneration of the dehumidifying part 330 may be checked.

In one embodiment, when the drying module DM operates in the moisture absorption mode, the controller 10 may control the drying module DM to stop operating in the moisture absorption mode and operate in the regeneration mode if a humidity change amount of the second module chamber 213 recognized by the first sensor 361 and a humidity change amount of the third module chamber 214 recognized by the second sensor 362 is less than or equal to a reference value.

In one embodiment, when the drying module DM operates in the regeneration mode, the controller 10 may control the drying module DM to stop operating in the regeneration mode if the humidity change amount of the second module chamber 213 recognized by the first sensor 361 and the humidity change amount of the third module chamber 214 recognized by the second sensor 362 is less than or equal to the reference value.

The shoes care device 1 according to one embodiment of the present invention further includes a third sensor 363 capable of measuring the amount of moisture adsorbed to the dehumidifying material 331, and the controller 10 may control the drying module DM to operate the regeneration mode until the amount of moisture measured by the third sensor 363 is less than or equal to a set value.

Specifically, the controller 10 may control all the heating parts 320 to operate until the amount of moisture measured by the third sensor 363 is less than or equal to the set value.

In this case, as illustrated in FIG. 11, the third sensor 363 may include a moisture sensor installed adjacent to the dehumidifying material 331 to measure the amount of moisture adsorbed to the dehumidifying material 331, and the type and number thereof may vary as necessary.

In this way, when the moisture adsorbed on the dehumidifying material 331 is sensed to exceed the reference value, the shoes care device 1 according to one embodiment of the present invention first regenerates all dehumidifying materials 331 until the moisture is less than or equal to the reference value. Accordingly, the dehumidifying material 331 can maintain an appropriate state for dehumidification all the time even when the shoes care device 1 operates to refresh the shoes.

FIG. 12*a* is an exploded perspective view illustrating the condenser 400 according to one embodiment of the present invention.

FIG. 12B is a view illustrating an internal state of the condenser 400 of FIG. 12*a*.

FIG. 12C is a front view illustrating the condenser 400 of FIG. 12*b*.

The condenser 400 forms a part of the regeneration path F20.

The condenser 400 may be made of or include a material such as synthetic resin, metal, ceramic, etc. The condenser 400 may be configured by injection molding, press molding, etc.

The condenser 400 may be made of a material having excellent thermal conductivity. The condenser 400 may be made of a metal with excellent thermal conductivity, and can be made of a material such as aluminum, an aluminum alloy, copper, a copper alloy, etc.

The condenser 400 may include a condenser housing 410, a flow path guide wall 440, a condenser inlet 450, and a condensed water outlet 470. The condenser 400 may include a condenser communication port 465.

In one embodiment of the present invention, the condenser 400 is disposed between the inner cabinet 100 and the outer cabinet 20. The condenser 400 may be disposed between the inner rear plate 110 and the outer rear plate 21, between the first inner side plate 120 and the first outer side plate 22, or between the second inner side plate 130 and the second outer side plate 23.

In the drawing in accordance with one embodiment of the present invention, the condenser 400 is illustrated to be disposed between the first inner side plate 120 and the first outer side plate 22.

A thickness cd3 of the condenser 400 (the size of the condenser 400 in the second direction (Y direction)) may be 0.5 to 1 times a distance between the first inner side plate 120 and the first outer side plate 22. A width cd2 of the condenser 400 (the size of the condenser 400 in the first direction (X direction)) and a height cd1 in the vertical direction may be 10 times or more and 40 times or less of the thickness cd3 of the condenser 400 (the size of the condenser 400 in the second direction (Y direction)), respectively.

The condenser 400 may be in close contact with the first inner side plate 120 and/or the first outer side plate 22. That is, the condenser 400 may be in close contact with an outer surface of the first inner side plate 120 or in close contact with an inner surface of the first outer side plate 22.

The first outer side plate 22 may be made of a material having excellent thermal conductivity. The first outer side plate 22 may be made of a metallic material having excellent thermal conductivity. The condenser 400 is disposed in close contact with or very close to the first outer side plate 22.

Accordingly, the water vapor moving through the condenser 400 may be effectively condensed.

In the shoes care device 1 according to one embodiment of the present invention, the machine room 50 is provided below the inner cabinet 100, and the condenser 400 is disposed between the inner cabinet 100 and the outer cabinet 20. That is, the condenser 400 is not provided inside the machine room 50 and is disposed outside a restricted space of the machine room 50.

In addition, the condenser 400 is disposed between the inner cabinet 100 and the outer cabinet 20 and can fully utilize the space between the inner cabinet 100 and the outer cabinet 20, and may be configured to have a large area on the whole.

In the shoes care device 1 according to one embodiment of the present invention, the condenser 400 may be disposed between the first inner side plate 120 of the inner cabinet 100 and the first outer side plate 22 of the outer cabinet 20, and the dry air duct 370 may be disposed between the inner rear plate 110 of the inner cabinet 100 and the outer rear plate 21 of the outer cabinet 20.

The condenser 400 may be formed to have a size corresponding to an area of one wall surface of the inner cabinet 100 (e.g., an area of the first inner side plate 120), and accordingly, the condenser 400 may be configured to have a relatively large area.

In one embodiment, the vertical height cd1 of the condenser 400 may be 0.5 to 1 times the vertical height h11 or h12 of the inner cabinet 100, and the width cd2 of the condenser 400 may be 0.5 to 1 times the width (the size in the first direction (X direction)) in the first inner side plate 120 of the inner cabinet 100.

According to one embodiment of the present invention, the vertical height of the machine room 50 in the shoes care device 1 may be formed relatively low, and the vertical heights h2 of the machine room 50 may be formed smaller than the vertical height h11 or h12 of the inner cabinet 100.

In this case, since the space inside the machine room 50 becomes relatively small, and the machine room 50 accommodates several components that constitute the shoes care device 1, the arrangement and design of each component may be restricted. Furthermore, unlike the present invention, when the condenser 400 is disposed inside the machine room 50, the shape and position of the condenser 400 may be limited, and the heat exchange efficiency of the condenser 400 may be reduced.

In one embodiment of the present invention, since the condenser 400 is disposed between the inner cabinet 100 and the outer cabinet 20, each component can be effectively arranged even when the vertical height of the machine room 50 needs to be formed relatively low.

In addition, by placing the condenser 400 between the inner cabinet 100 and the outer cabinet 20, the condenser 400 can be formed in a relatively thin and wide shape, the heat exchange area of the condenser 400 can be expanded, and the heat exchange between an external air of the shoes care device 1 and the condenser 400 can be easily performed. Accordingly, water vapor passing through the condenser 400 may be effectively condensed.

While the condenser 400 is disposed between the first inner side plate 120 and the first outer side plate 22, the condenser 400 may be disposed to extend upwards from the module housing 200. Further, the condenser 400 is disposed higher than the sump 600 disposed inside the machine room 50.

Accordingly, steam in the third module chamber 214 of the module housing 200 naturally rises and flows into the condenser 400, and the condensed water in the condenser 400 naturally descends by gravity and flows into the sump 600, and when the dehumidifying material 331 is regenerated, the steam can be effectively condensed and discharged.

The condenser housing 410 forms an overall appearance of the condenser 400. A condensation space 420, which is a space inside the condenser 400, is provided inside the condenser housing 410.

The condenser inlet 450 forms an inlet of the condenser 400 through which air flows into the condenser 400, and forms an inlet of the condensation space 420.

The condenser inlet 450 is connected to and in communication with the wet air outlet 232. In the shoes care device 1 according to one embodiment of the present invention, the wet air outlet 232 and the condenser inlet 450 may be directly connected to each other while being disposed inside and outside based on the first inner side plate 120 of the inner cabinet 100.

While wet air introduced into the condenser 400 through the condenser inlet 450 moves along the flow path inside the condenser 400, the wet air is condensed by heat exchange and moves below the condenser 400.

The condensed water outlet 470 forms an outlet through which the condensed water in the condenser 400 is discharged, and also forms an outlet of the condensation space 420.

The condensed water outlet 470 of the condenser 400 is connected to the sump 600, and the condensed water inside the condenser 400 moves to the sump 600.

The condensed water outlet 470 may be formed in the lower end of the condenser 400. That is, the condensed water outlet 470 may be formed in the lowest part of the condensation space 420. The lower end of the condensation space 420 may be inclined downwardly toward the condensed water outlet 470.

The condensed water outlet 470 is connected to the sump 600. The condensed water outlet 470 and the sump 600 may be connected by a pipe, a hose, etc.

The flow path guide wall 440 is formed in the shape of a plate having a narrow width and a long length. The flow path guide wall 440 may be provided in the inside (the condensation space 420) of the condenser housing 410 and may be formed in a plural form.

A plurality of flow path guide walls 440 are disposed to be spaced apart from each other to form a path through which water vapor and condensed water move. The plurality of flow path guide walls 440 may be disposed to cross each other.

The flow path guide wall 440 forms a condenser flow path 430 which is a path extending from the condenser inlet 450 to a condenser outlet 460 in the condensation space 420. The condenser flow path 430 is a movement passage of air (or water) provided inside the condenser 400, and connects the condenser inlet 450 and the condenser outlet 460. In addition, the condenser flow path 430 is a movement passage of air (or water) provided inside the condenser 400, and connects the condenser inlet 450 and the condensed water outlet 470.

The condenser flow path 430 may include an introduction section 431 and a condensation section 432.

As the plurality of flow path guide walls 440 are spaced apart from each other, the condensation section 432 may be provided between the flow path guide walls 440.

The condensation section 432 may be formed in a zigzag shape extending from the uppermost side of the condensation space 420 to the lower side.

In one embodiment of the present invention, an angle formed by the flow path guide wall 440 forming the condensation section 432 with a horizontal plane may be 1 to 10°. The flow path guide wall 440 constituting the condensation section 432 is formed substantially along the first direction (X direction), and may be disposed to be inclined upwards or downwards along the first direction (X direction).

In one embodiment of the present invention, the length of the flow path guide wall 440 constituting the condensation section 432 may be 30 to 400 mm, the width of the flow path guide wall 440 may be 5 to 20 mm, and an interval between the flow path guide walls 440 may be 10 to 50 mm.

In the arrangement explained above, the contact area and contact time between the steam and the condenser 400 can be increased while the water vapor moves along the zigzag-shaped condensation section 432 in the condensation space 420, and the heat exchange between the water vapor and condenser 400 and the condensation of the water vapor can be effectively performed.

In addition, by inclinedly forming the flow path guide wall 440, the condensed water formed in the condensation space 420 can move downwards along the surface of the flow path guide wall 440, and can move smoothly in the direction of gravity without accumulating inside the condenser 400, and residual water can be effectively prevented from occurring inside the condenser 400.

The introduction section 431 may extend upwards from the condenser inlet 450 to an upper start part of the condensation section 432.

The condenser outlet 460 forms an outlet of the condenser 400 through which air inside the condenser 400 is discharged.

The condenser outlet 460 may be formed in the lower part of the condenser 400. The condenser outlet 460 may be formed in a lower side of the condensation section 432.

However, the condenser outlet 460 may be formed in an area higher than the condensed water outlet 470. Accordingly, the condensed water inside the condenser 400 may be discharged through the condensed water outlet 470, and the air inside the condenser 400 may be discharged through the condenser outlet 460.

Meanwhile, in the shoes care device 1 according to one embodiment of the present invention, the inside of the condenser 400 and the inside of the module housing 200 may be configured to communicate with each other through the condenser outlet 460.

In the shoes care device 1 according to one embodiment of the present invention, the condenser outlet 460 may be formed in a position and a height corresponding to the first condensed water discharge hole 233, and the condenser outlet 460 and the first condensed water discharge hole 233 may be coupled to each other.

In the air introduced into the condenser 400, the condensed water moves to the sump 600 through the condensed water outlet 470, and uncondensed air may flow back into the module housing 200 through the condenser outlet 460.

High-temperature and humid air inside the module housing 200 forming the conversion flow path F10*a* flows into the condenser 400 of the regeneration path F20, the condensed water inside the condenser 400 moves to the sump 600, the uncondensed air can be resupplied into the module housing 200 forming the conversion flow path F10*a*, and the air is condensed while being circulated in the module housing 200 and the condenser 400.

The condenser communication port 465 communicates with the third module chamber 214 of the module housing 200 at a lower side of the condensation space. That is, the inside of the condenser 400 and the inside of the module housing 200 may be configured to communicate with each other through the condenser communication port 465.

The condenser communication port 465 may be formed directly above the condensed water outlet 470.

In the shoes care device 1 according to one embodiment of the present invention, the condenser communication hole 465 may be formed in a position and a height corresponding to the second condensed water discharge hole 234, and the condenser communication hole 465 and the second condensed water discharge hole 234 may be coupled to each other.

The condensed water inside the third module chamber 214 flows into the condenser 400 through the second condensed water discharge hole 234 and the condenser communication port 465, and moves to the sump 600 through the condensed water outlet 470.

The shoes care device 1 according to one embodiment of the present invention may include a condenser connection portion 490.

The condenser connection portion 490 may form a flow path directly connecting the condenser 400 of the first management device 2*a* and the condenser 400 of the second management device 2*b*.

The condenser connection portion 490 may be formed in the form of a pipe, a hose, etc. In the shoes care device 1 according to one embodiment of the present invention, when the condenser 400 of the first management device 2*a* is disposed on the upper side of the condenser 400 of the second management device 2*b* and the sump 600 is disposed on the lower side of the condenser 400 of the second management device 2*a*, the condensed water inside the condenser 400 of the first management device 2*a* may move into the condenser 400 of the second management device 2*b* through the condenser connection portion 490 and then move the sump 600.

For connection with the condenser connection portion 490, a condenser connector 491 may be formed in the condenser 400. The condenser connector 491 forms an inlet through which condensed water flows into the condenser 400.

The condenser connector 491 may be formed adjacent to the condensation space 420 of the condenser 400. The condenser connector 491 may be formed adjacent to the condensed water outlet 470 of the condenser 400.

When the condenser 400 of the first management device 2*a* is disposed above the condenser 400 of the second management device 2*b* and the sump 600 is disposed below the condenser 400 of the second management device 2*b*, the condenser connection portion 490 may be configured to connect the condensed water outlet 470 of the condenser 400 of the first management device 2*a* and the condenser connector 491 of the condenser 400 of the second management device 2*b*. In this case, the condenser connector 491 is not formed in the condenser 400 of the first management device 2*a*, or the condenser connector 491 of the condenser 400 of the first management device 2*a* may be blocked with a separate stopper.

The condensed water inside the condenser 400 of the first management device 2*a* may move into the condenser 400 of the second management device 2*b* through the condenser connection portion 490 and then move to the sump 600.

Accordingly, when the first management device 2*a* and the second management device 2*b* are arranged vertically in the shoes care device 1, a flow path (such as a hose) connecting the condenser 400 of the second management device 2*b* and the sump 600 may be used as a flow path configured to discharge the condensed water of the first management device 2*a*. Hence, the length of the flow path (hose, etc.) required for discharging the condensed water can be formed short on the whole, and only the condenser 400 of the second management device 2*b* may be directly connected to the sump 600 to discharge the condensed water of all the condensers 400. As a result, since an overall coupling structure can be simplified, which makes it easy to assemble and maintain the shoes care device 1, and the condensed water may be easily discharged.

Most of the water vapor in the air passing through the condenser 400 is condensed and moves to the sump 600 through the condensed water outlet 470. However, some small droplets condensed in the air may not be discharged through the condensed water outlet 470.

FIG. 13 is a cross-sectional view illustrating a first module chamber of a module housing in the shoes care device 1 according to one embodiment of the present invention.

The blowing part 310 forms a part of the connection path F10. The blowing part 310 is configured to generate an air flow in the connection path F10.

The blowing part 310 may include the blowing fan 313, a blowing housing 311, and a blowing motor 314.

The blowing fan 313 may be configured to rotate around a rotation axis 313*a* in the third direction (Z direction) perpendicular to the first direction (X direction). The blowing motor 314 of the blowing part 310 rotates the blowing fan 313.

The blowing housing 311 is configured to accommodate the blowing fan 313. The blowing housing 311 may have a substantially round shape around the rotation axis 313*a* of the blowing fan 313. The blowing housing 311 may be formed in a circular shape or a spiral shape around the rotation axis 313*a* of the blowing fan 313.

An inlet 311*a* of the blowing part 310 is formed on a bottom surface of the blowing housing 311, and air flows into the blowing housing 311 below the bottom surface of the blowing housing 311.

The size of the blowing housing 311 in the horizontal direction may be formed larger than the size of the blowing housing 311 in the vertical direction. The size of the blowing housing 311 in the horizontal direction may be made more than twice the size of the blowing housing 311 in the vertical direction.

In the shoes care device 1 according to one embodiment of the present invention, when the blowing fan 313 rotates around a vertical rotation axis to allow the module housing 200 to have a relatively low vertical height, the diameter of the blowing housing 311 and the diameter of the blowing fan 313 can be formed sufficiently large, and the flow rate of air transported by the blowing part 310 can be sufficiently increased.

The blowing housing 311 may communicate with the first module chamber 212 on the rotating axis 313*a* of the blowing fan 313, and the edge thereof may be connected to and communicate with the blowing duct 312. The blowing duct 312 forms an outlet 311*b* of the blowing part 310.

Accordingly, the air below the blowing housing 311 in the first module chamber 212 moves upwards near the rotation axis 313*a* of the blowing fan 313 and flows into the blowing housing 311, and the air inside the blowing housing 311 is pressurized to the edge of the blowing housing 311 depending on the rotation of the blowing fan 313 and moves along the circumferential direction of the blowing housing 311 toward the blowing duct 312.

The blowing housing 311 includes the blowing duct 312 forming the outlet 311*b* of the blowing housing 311. The blowing duct 312 may extend in a horizontal direction from the blowing housing 311. The blowing duct 312 may be formed substantially along the second direction (Y direction). The blowing duct 312 may extend to the second module chamber 213, and all air discharged from the blowing part 310 through the blowing duct 312 may move to the second module chamber 213.

The blowing housing 311 and the blowing duct 312 may form a spiral passage around the rotating axis 313*a* of the blowing fan 313 together such that, when the blowing fan 313 rotates, the air inside the blowing housing 311 naturally moves to the blowing duct 312.

Along the rotation direction of the blowing fan 313, the distance in the radial direction from the rotation axis 313*a* of the blowing fan 313 may be sequentially increased from the blowing housing 311 to the blowing duct 312. In one embodiment, as illustrated in FIG. 9, the distance from the rotation axis 313*a* of the blowing fan 313 to the outer edges of the blowing housing 311 and the blowing duct 312 may be configured to increase sequentially in the clock direction.

In addition, the second module chamber 213 may be configured to extend from an end of the blowing duct 312.

In addition, the direction of sequentially connecting the first module chamber 212, the second module chamber 213, the third module chamber 214 and the dry air outlet 231 may be configured to correspond to the direction of the movement of air around the rotation axis of the blowing fan 313 in the blowing housing 311.

Based on FIG. 9, the rotation direction of the blowing fan 313 may be configured to be clockwise, the distance from the rotation axis 313*a* of the blowing fan 313 to the outer edges of the blowing housing 311 and the blowing duct 312 may be configured to sequentially increase in the clockwise direction and have a spiral form, and the direction of sequentially connecting the first module chamber 212, the second module chamber 213, the third module chamber 214 and the dry air outlet 231 may be configured to be clockwise.

Accordingly, the air passing through the blowing housing 311 and the blowing fan 313 may move in the clockwise direction inside the module housing 200 toward the dry air outlet 231 or the wet air outlet 232, and the air may move naturally along the formation direction of the flow path (the convention flow path F10*a*) inside the module housing 200.

In addition, by performing the blowing part 310 and the blowing duct 312 as described above, the flow rate of the air supplied to the third module chamber 214 can be stably secured, and sufficient air can be supplied to the dehumidifying part 330.

In addition, while the air moving through the third module chamber 214 smoothly passes through the dehumidifying part 330, a flow path resistance of the air passing through the dehumidifying part 330 can be prevented from unnecessarily increasing.

In the shoes care device 1 according to one embodiment of the present invention, the blowing part 310 may be spaced apart from the bottom of the first module chamber 212 such that air in the first module chamber 212 flows into the blowing part 310 from the lower side of the first module chamber 212. Accordingly, even if condensed water is generated inside the first module chamber 212, the condensed water can move along the bottom surface of the first module chamber 212 and be discharged to the outside of the module housing 200, and the residual water can be prevented or minimized in the blowing part 310.

In the shoes care device 1 according to one embodiment of the present invention, the direction of sequentially connecting the first module chamber 212, the second module chamber 213, the third module chamber 214 and the dry air outlet 231 may correspond to the direction of movement of air around the rotation axis of the blowing fan 313 in the blowing housing 311. Accordingly, the air introduced into the blowing housing 311 can naturally move into the module housing 200 in a predetermined direction from the blowing housing 311 to the second module chamber 213, the third module chamber 214 and the dry air outlet 231 with respect to the rotation axis of the blowing fan 313. Accordingly, a smooth air flow may be achieved in the module housing 200, and an unintentional increase in flow resistance can be prevented.

FIG. 14 is a perspective view illustrating a dehumidifying part and a dehumidifying material housing according to one embodiment of the present invention.

FIG. 15 is a bottom perspective view illustrating a module cover according to one embodiment of the present invention.

FIG. 16 is a cross-sectional view illustrating the third module chamber 214 of the module housing 200 in the shoes care device 1 according to the present invention.

The dehumidifying part 330 according to one embodiment of the present invention may be configured to have a predetermined thickness and length. In one embodiment, as described above, the dehumidifying part 330 may be configured to have a substantially hexahedral shape.

Accordingly, the dehumidifying part 330 may have a predetermined length, width, and thickness.

Each of a length ZD1 and a width ZD2 of the dehumidifying part 330 may be formed longer than a thickness ZD3 of the dehumidifying part 330. In one embodiment, the length ZD1 and the width ZD2 of the dehumidifying part 330 be made more than twice the thickness ZD3 of the dehumidifying part 330. In addition, the length ZD1 of the dehumidifying part 330 may be formed longer than the width ZD2 of the dehumidifying part 330.

The dehumidifying part 330 includes an upper surface 333 and a lower surface 334 facing each other. Here, the upper surface 333 of the dehumidifying part 330 and the lower surface 334 of the dehumidifying part 330 are opposite surfaces facing each other in the thickness direction of the dehumidifying part 330.

As described above, the dehumidifying part 330 is provided with the plurality of dehumidification through holes 332. The dehumidifying through hole 332 may be configured to penetrate the dehumidifying part 330 in a direction in which the upper surface 333 and the lower surface 334 of the dehumidifying part 330 are connected to each other.

In the shoes care device 1 according to one embodiment of the present invention, the dehumidifying part 330 may be accommodated inside the module housing 200 while being accommodated in the dehumidifying material housing 340.

The dehumidifying material housing 340 is formed in the form of a container capable of accommodating the dehumidifying part 330. In a state where the dehumidifying part 330 is accommodated in the dehumidifying material housing 340, an edge wall of the dehumidifying material housing 340 may be in close contact with the dehumidifying part 330. Accordingly, the dehumidifying part 330 can be prevented from being separated inside the dehumidifying material housing 340.

The dehumidifying material housing 340 has an upper side opened and a lower side opened. However, the lower side of the dehumidifying material housing 340 is provided with a support 341 that supports the dehumidifying part 330 such that the dehumidifying part 330 does not deviate downwards. The supports 341 may be disposed to cross each other in the form of a grid or a net. The gap (opening) between the supports 341 is formed sufficiently larger than the dehumidifying through hole 332 so as not to interfere with the flow of the air passing through the dehumidifying part 330.

In the shoes care device 1 according to one embodiment of the present invention, when the dehumidifying part 330 is disposed inside the module housing 200, the dehumidifying part 330 may be disposed so that the upper surface 333 and the lower surface 334 are inclined without being parallel to the horizontal direction.

The dehumidifying part 330 may be disposed in the third module chamber 214 in a form inclined downwardly toward the second module chamber 213. That is, the upper surface 333 and the lower surface 334 of the dehumidifying part 330 may be disposed to be inclined downwardly toward the second module chamber 213.

Since the dehumidifying part 330 is inclined downwardly toward the second module chamber 213 in the third module chamber 214, the air before penetrating the dehumidifying part 330 is disposed in an upper space of the dehumidifying part 330 in the third module chamber 214, and the air after penetrating the dehumidifying part 330 is disposed in a lower space of the dehumidifying part 330 in the third module chamber 214. Here, the upper space of the dehumidifying part 330 in the third module chamber 214 is defined as 'a first flow path F10*aa*', and the lower space of the dehumidifying part 330 in the third module chamber 214 is defined as 'a second flow path F10*ab*.

In addition, since the dehumidifying part 330 is disposed to be inclined in the third module chamber 214, the dehumidifying through hole 332 is also disposed to be inclined.

A cover partition wall 242 may be formed in the module cover 202.

The cover partition wall 242 is formed in a plate shape extending downwards from the edge of the dehumidifying material exit 240. The cover partition wall 242 may be formed in a substantially triangular plate shape.

The cover partition wall 242 may be configured such that a lower edge thereof is inclined downwards from the third module chamber 214 to the second module chamber 213. A pair of cover partition walls 242 may be provided to be spaced apart from each other in the left-right direction. The distance between the pair of cover partition walls 242 may be configured to correspond to the length of the dehumidifying part 330.

A lower locking portion 243 may be formed in a lower edge of the cover partition wall 242 and a front edge of the cover partition wall 242 in the first direction (X direction), and an upper locking portion 342 may be formed in an upper edge of the dehumidifying material housing 340 to get settled and locked in an upper side of the lower locking portion 243. Accordingly, when the dehumidifying material housing 340 is settled in the cover partition wall 242 in a state where the dehumidifying part 330 is accommodated in the dehumidifying material housing 340, the upper locking portion 342 of the dehumidifying material housing 340 is settled and assembled in an upper side of the lower locking portion 243 of the cover partition wall 242.

In addition, in this case, the cover partition wall 242 may block direct communication between the first flow path F10*aa* and the second flow path F10*ab* while the lower edge thereof is in close contact with the upper edge of the dehumidifying part 330.

By providing the cover partition wall 242 in the module cover 202, the air in the first flow path F10*aa* may pass through the dehumidifying part 330 over the entire area of the dehumidifying part 330 and move to the second flow path F10*ab*. In addition, a plurality of dehumidifying through holes 332 penetrating the dehumidifying part 330 in the thickness direction may be formed in the dehumidifying part 330, thereby increasing the contact area between the air passing through the third module chamber 214 and the dehumidifying material 331.

In one embodiment of the present invention, the dehumidifying part 330 is not disposed parallel to the horizontal direction and is inclined downwardly toward the second module chamber 213. Comparing this with the case where the dehumidifying part 330 is disposed horizontally, the size of the upper surface of the dehumidifying part 330 may be formed larger, and the entire volume of the dehumidifying part 330 may be increased. Accordingly, the amount of dehumidification of air by the dehumidifying part 330 may be increased.

As described above, as the dehumidifying part 330 is disposed to be inclined, the direction from the first flow path F10*aa* to the second flow path F10*ab* through the dehumidifying part 330 is configured not to be vertical but to be inclined. A rapid change in the direction of air in a path through which the air moves to the second module chamber 213, the first flow path F10*aa*, and the second flow path F10*ab* can be reduced to achieve a smooth movement of air.

Accordingly, the natural movement of air moving through the dehumidifying part 330 can be achieved, and an unnecessary flow path resistance can be minimized in the third module chamber 214.

In addition, while the air of the second module chamber 213 moves from the first flow path F10*aa* to the second flow path F10*ab*, moisture (small droplets or condensed water) may enter or occur in the third module chamber 214. The bottom surface of the dehumidifying part 330 may be naturally separated from the bottom of the third module chamber 214, and the air inside the third module chamber 214 may move downwards through the dehumidifying part 330 from the upper side of the third module chamber 214. Accordingly, the small droplets or the condensed water can move along the bottom surface of the third module chamber 214 without remaining or seeping into the dehumidifying part 330, and can be easily discharged toward the condenser 400.

In one embodiment, the dehumidifying part 330 may have a constant cross-section along the second direction (Y direction).

In another embodiment, the dehumidifying part 330 may be formed in a form where the thickness thereof is deformed along the second direction (Y direction).

In the shoes care device 1 according to one embodiment of the present invention, the first module chamber 212 and the second module chamber 213 are formed in front of the third module chamber 214 with respect to the first direction (X direction). That is, when the longitudinal direction of the dehumidifying part 330 is formed along the second direction (Y direction), the first module chamber 212 or the second module chamber 213 does not interfere with securing the length of the third module chamber 214, and the blowing part 310 or the heating part 320 does not interfere with securing the length of the dehumidifying part 330. Accordingly, a total length ZD1 of the dehumidifying part 330 may be formed longer than the length of each of the blowing part 310 and the heating part 320 with respect to the second direction (Y direction).

Accordingly, the length of the dehumidifying part 330 can be secured sufficiently long, the entire volume of the dehumidifying part 330 can be formed relatively large, and the dehumidifying amount per unit time of the dehumidifying part 330 can be improved.

In the shoes care device 1 according to one embodiment of the present invention, the length ZD1 of the dehumidifying part 330 may be longer than ½ of the length of each of the inner cabinet 100 and the module housing 200 with respect to the second direction (Y direction).

The dehumidifying part 330 may be spaced apart from the bottom of the third module chamber 214 so that the air inside the third module chamber 214 moves downwards through the dehumidifying part 330 from the upper side of the third module chamber 214. Since the dehumidifying part 330 is spaced apart from the bottom of the third module chamber 214, the air inside the third module chamber 214 can smoothly pass through the dehumidifying part 330, and the condensed water generated by penetrating the dehumidifying part 330 moves along the bottom surface of the third module chamber 214 and can be discharged outside the module housing 200.

In the shoes care device 1 according to one embodiment of the present invention, the dehumidifying part 330 provided in the third module chamber 214 may be disposed to be inclined. The dehumidifying part 330 may be disposed to be inclined downwardly toward the second module chamber 213. Accordingly, when the air moves from the second module chamber 213 to the third module chamber 214, the air can easily pass through the dehumidifying part 330. In addition, compared to the case where the dehumidifying part 330 is horizontally arranged, the area or volume of the dehumidifying part 330 can be further expanded, and the dehumidifying amount per unit time of the dehumidifying part 330 can be improved.

FIG. 17 is a perspective view illustrating the steam separator 720 according to one embodiment of the present invention.

FIG. 18*a* is a cross-sectional view illustrating a part of a separating inlet 723 of the steam separator 720 in the shoes care device 1 according to one embodiment of the present invention.

FIG. 18*b* is a cross-sectional view illustrating a part of a separating connector 722 of the steam separator 720 in the shoes care device 1 according to one embodiment of the present invention.

The shoes care device 1 according to one embodiment of the present invention may further include the steam separator 720 installed adjacent to the steam inlet 204. The steam separator 720 is provided in each of the first management device 2*a* and the second management device 2*b*.

Most of the steam supplied from the steam generator 700 to the accommodation space 101 of the inner cabinet 100 is in a gaseous state, but the stream can be condensed during the movement to generate condensed water in a liquid state.

As described above, measures are needed to prevent moisture from leaving at an unintended part inside the shoes care device 1.

This is applicable to the flow path through which steam is supplied, and the condensed water in the steam needs to be prevented from being adsorbed and remaining on an inner surface of the flow path through which steam is supplied.

In addition, even if the condensed water in steam is supplied to the inside of the inner cabinet 100 without change, since the condensed water is not supplied to the shoes in the form of steam, it is difficult to properly perform the management on the shoes (sterilization treatment by high-temperature steam, swelling of shoe materials, etc.).

Therefore, preferably, the condensed water in the steam is removed through the steam separator 720 installed in the steam inlet 204 before the condensed water in the steam flows into the steam inlet 204.

In the shoes care device 1 according to one embodiment of the present invention, the steam separator 720 may include a separating base 721, the separating connector 722, the separating inlet 723, and a separating outlet 724.

The separating base 721 is formed in a housing shape forming a predetermined inner space 721*a*. The separating base 721 may have an inner area relatively larger than the hole formed by the steam inlet 204 in a plan view, and the separating base 721 may be fixed to the module housing 200 while covering the steam inlet 204 in the lower side of the steam inlet 204.

The separating inlet 723 forms an inlet through which steam flows into the steam separator 720. The separating inlet 723 may be connected to the steam valve 710, and the steam generated by the steam generator 700 may flow into the steam separator 720 through the separating inlet 723 after passing through the steam valve 710. The separating inlet 723 may be disposed lower than the separating connector 722. The separating inlet 723 may be formed in a shape opened vertically from the lower side of the separating base 721.

The separating inlet 723 may have a vertical tubular shape, and an upper end thereof may be formed higher than a bottom surface 721*b* of the separating base 721. The separating inlet 723 may be formed to protrude upward from the bottom surface 721*b* of the separating base 721. Accordingly, even if the condensed water occurs inside the separating base 721 and flows to the bottom surface 721*b* of the separating base 721, the condensed water may be prevented from flowing into the separating inlet 723, and all the condensed water may be discharged to the separating outlet 724, as described below.

The separating connector 722 forms an outlet through which steam inside the steam separator 720 is discharged. The steam inside the steam separator 720 may move to the steam inlet 204 through the separating connector 722. The separating connector 722 may be formed above the separating base 721. The separating connector 722 can be formed in a form opened from the upper side of the separating base 721 to the upper side in the vertical direction, and can be directly connected to and communicate with the steam inlet 204.

The separating outlet 724 forms an outlet through which condensed water inside the steam separator 720 is discharged. The separating outlet 724 is connected to the sump 600, and the condensed water inside the steam separator 720 may move to the sump 600 through the separating outlet 724. The separating outlet 724 may be disposed lower than the separating connector 722. The separating outlet 724 may be formed in a form opened from the lower side of the separating base 721 to the lower side in the vertical direction.

The separating outlet 724 may be formed in a lower end of the bottom of the separating base 721. That is, the separating outlet 724 may be formed at the lowest part among the bottom surfaces of the separating base 721. The bottom surface of the separating base 721 may be inclined downwardly toward the separating outlet 724. In one embodiment, the bottom surface of the separating base 721 may be inclined downward in the second direction (Y direction) or a direction opposite to the second direction (Y direction), and the separating outlet 724 may be formed on the bottom surface of the separating base 721 at a front end or a rear end of the second direction (Y direction).

The steam flowing into the steam separator 720 may be heated to a predetermined temperature, and may be above ordinary temperature (e.g., 20±5° C.). Since this steam has a strong tendency to rise, it can move naturally through the separating connector 722 formed upwards from the upper side of the separating base 721.

Some of the steam flowing into the steam separator 720 may be cooled and condensed inside the separating base 721, and the condensed water may flow along the bottom surface of the separating base 721, and may be discharged to the outside of the steam separator 720 through the separating outlet 724 and move to the sump 600.

As described above, in the shoes care device 1 according to one embodiment of the present invention, since the steam separator 720 is provided with the separating connector 722 and the separating outlet 724 separately, when the steam and condensed water are present together, each of them can move through an individual path.

In addition, the separating connector 722 is formed in the upper side of the steam separator 720, while the separating outlet 724 is formed in the lower side of the steam separator 720. Accordingly, according to the properties of the steam and the condensed water, the water vapor and condensed water are discharged in opposite directions, and residual water can be prevented from occurring in the flow path through which the steam is supplied.

FIGS. 19*a* and 19*b* are perspective views illustrating the main shelf 40 according to one embodiment of the present invention.

FIG. 20 is a cross-sectional view illustrating the shoes care device 1 according to one embodiment of the present invention, and schematically illustrating a state in which the shoes S are settled on an upper side of the main shelf 40.

FIG. 21 is a cross-sectional view illustrating the shores care device 1 according to one embodiment of the present invention and is a view schematically illustrating a state in which the shoes S having a larger size than that of FIG. 20 is settled on the upper side of the main shelf 40.

As mentioned above, the main shelf 40 is placed and used on the bottom of the inner cabinet 100, and when the main shelf 40 is placed on the bottom of the inner cabinet 100, the upper surface of the main shelf 40 forms the bottom surface of the accommodation space 101. In addition, the module cover 202 of the module housing 200 may form the bottom surface of the inner cabinet 100. In this case, the main shelf 40 is settled on the upper side of the module housing 200 (the upper surface of the module cover 202.

The upper surface of the main shelf 40 forms the bottom surface of the accommodation space 101 and is configured to be inclined downwardly toward the first direction (X direction).

The main shelf 40 may be formed such that a pair of shoes S are settled on the upper surface thereof. The main shelf 40 is substantially formed in a thin and wide plate shape.

The shoes care device 1 according to one embodiment of the present invention may include a pair of a first guide rib 41*a* and a second guide rib 41*b* such that the position where the shoes are placed is guided to the user.

The first guide rib 41*a* and the second guide rib 41*b* may guide the settling position and direction of the shoes S such that the shoes S can be placed on the main shelf 40 to match or substantially match the front and rear directions of the shoes S to the first direction (X direction) when the user places the shoes S on the bottom of the accommodation space 101.

The first guide rib 41*a* and the second guide rib 41*b* are formed on the bottom surface of the inner cabinet 100. The first guide rib 41*a* and the second guide rib 41*b* may be formed on the upper surface of the main shelf 40.

Each of the first guide rib 41*a* and the second guide rib 41*b* are formed to support the front end or the rear end of the shoes S. Each of the first guide rib 41*a* and the second guide rib 41*b* may correspond to a front edge shape or a rear edge shape of the shoes S. Each of the first guide rib 41*a* and the second guide rib 41*b* may be formed in a curved shape that is concave in the first direction (X direction). Each of the first guide rib 41*a* and the second guide rib 41*b* may be formed in an arc shape.

Each of the first guide rib 41*a* and the second guide rib 41*b* is formed to protrude upwards from the bottom surface of the accommodation space 101. When the first guide rib 41*a* and the second guide rib 41*b* are formed in the main shelf 40, the first guide rib 41*a* and the second guide rib 41*b* protrude upwards from the upper surface of the main shelf 40.

The protruding heights of the first guide rib 41*a* and the second guide rib 41*b* may be variously formed according to embodiments. The protruding heights of the first guide rib 41*a* and the second guide rib 41*b* may be 3 to 20 mm.

The first guide rib 41*a* and the second guide rib 41*b* are positioned at different sides based on the reference plane RP. The first guide rib 41*a* and the second guide rib 41*b* may be symmetrical with respect to the reference plane RP.

The first guide rib 41*a* and the second guide rib 41*b* are formed in front of the accommodation space 101 based on the first direction (X direction). Based on the first direction (X direction), when the first guide rib 41*a* and the second guide rib 41*b* are formed relatively ahead, the steam inlet 204 may be formed relatively in the rear.

In the shoes care device 1 according to one embodiment of the present invention, the steam inlet 204 is formed on the bottom of the accommodation space 101 or formed adjacent to the bottom. The steam inlet 204 may be formed in the rear center of the accommodation space 101 based on the first direction (X direction). When the reference plane RP is a center surface that bisects the left and right sides of the shoes care device 1, the reference plane RP crosses the steam inlet 204.

Opposite sides of the accommodation space 101 may be symmetrical with respect to the reference plane RP.

Based on the rear end of the bottom surface of the accommodation space 101 in the first direction (X direction), when a distance to the steam inlet 204 is BD1, a distance to the first guide rib 41*a* and the second guide rib 41*b* is BD2, a distance to the front end of the bottom surface of the accommodation space 101 is BD3, the BD1 may be 1/10 or less of the BD3, and the BD2 may be 9/10 to 10/10 of the BD3.

When the steam inlet 204 is formed at the rearmost portion of the bottom surface of the accommodation space 101 based on the first direction (X direction), the first guide rib 41*a* and the second guide rib 41*b* may be formed in the frontmost part.

According to the shoes care device 1 according to one embodiment of the present invention, first of all, since the shoes are placed and managed on the bottom of the accommodation space 101, it is convenient to enter or withdraw the shoes from the accommodation space 101, and the shoes of various sizes may be easily managed. In addition, the steam generated by the steam generator 700 may be dispersed into the inner cabinet 100 to refresh the shoes S, and the air inside the inner cabinet 100 may be circulated through the connection path F10 to dehumidify the air.

Usually, since the shoes are made in a round shape in the front and back, or the width thereof becomes narrower toward the front and back, when a pair of shoes(S) is placed side by side, a space is formed between the front or rear ends of the pair of shoes S. In one embodiment of the present invention, since the steam inlet 204 is located in the rear center of the accommodation space 101 based on the first direction (X direction), when the pair of shoes is placed on the bottom of the accommodation space 101, the possibility of covering the steam inlet 204 by the shoes may be minimized, and the steam may be uniformly supplied to each of the shoes.

Unlike the embodiment of the present invention, when the steam inlet 204 is formed by being biased to the left or right in the accommodation space 101, more steam supplied through the steam inlet 204 may be further supplied to any one shoe, and accordingly, uniform shoe management may not be achieved.

According to one embodiment of the present invention, even when high-temperature steam is discharged through the steam inlet 204, the steam is directly discharged to the bottoms of the shoes S, thereby minimizing the possibility of ununiformly treating the pair of shoes or damaging the shoes.

According to the shoes care device 1 according to one embodiment of the present invention, when the user places the pair of shoes on the bottom of the accommodation space 101, the pair of shoes are on the bottom of the accommodation space 101 in a state where one shoe is supported by the first guide rib 41*a* and the other shoe is supported by the second guide rib 41*b*. Accordingly, two shoes are located on different sides based on the reference plane RP, and the steam inlet 204 is located at one part of the reference plane RP (see FIG. 20).

When the shoe size is very large (e.g., when the shoe length is longer than the length of the main shelf 40 with respect to the first direction (X direction)), a pair of shoes may be placed diagonally apart toward the back of the first direction (X direction) (see FIG. 21). In this case, the steam inlet 204 is located between the pair of shoes S. As such, according to one embodiment of the present invention, when the size of shoes is very large, the possibility of covering the steam inlet 204 by the shoes or of placing the shoes very close to the steam inlet 204 can be minimized.

Unlike the embodiment of the present invention, when the steam inlet 204 is formed to be biased to the left or right in the accommodation space 101, if the size of the managed shoes is very large, more steam supplied through the steam inlet 204 may be supplied to any one shoe, or the steam inlet 204 may be covered by the shoes, and when high-temperature steam is discharged from the steam inlet 204, this can damage the shoes.

In the shoes care device 1 according to one embodiment of the present invention, as described above, the outlet 203 may be formed in front of the upper surface of the module housing 200 in the first direction (X direction). In this case, a shelf hole 45 vertically penetrated directly above the outlet 203 is formed in the main shelf 40.

A net such as a grid shape or a mesh shape may be formed in the shelf hole 45.

Accordingly, a plurality of shelf holes 45 are provided.

The plurality of shelf holes 45 may be repeatedly arranged along the second direction (Y direction). The shape formed by the plurality of shelf holes 45 on the whole may be formed in a long shape along the second direction (Y direction) in the main shelf 40.

An area in which the shelf hole 45 is formed in a plan view may be formed to coincide with or substantially coincide with an area in which the outlet 203 is formed.

The first guide rib 41*a* and the second guide rib 41*b* are formed ahead of the shelf hole 45 in the first direction (X direction).

As described above, the entire area of the main shelf 40 in the front-rear direction may be used as an area where the shoes are settled, based on the first direction (X direction), and the condensed water on the upper surface of the main shelf 40 may flow along the upper surface of the main shelf 40 and flow into the shelf hole 45 and the outlet 203.

The main shelf 40 may include a plurality of main isolation ribs 42. The plurality of main isolation ribs 42 protrude upwards from the upper surface of the main shelf 40 and are spaced apart from each other. The main isolation rib 42 may be formed along the first direction (X direction) and may be formed in a direction inclined with the first direction (X direction).

The protruding height of the main isolation rib 42 may be formed lower than the protruding heights of the first guide rib 41*a* and the second guide rib 41*b*.

As each of the main isolation ribs 42 is spaced apart from each other, a gap (space or valley) is repeatedly formed between the main isolation ribs 42.

The main isolation rib 42 may be formed in most areas of the upper surface of the main shelf 40. The main isolation rib 42 may be formed in most areas of the upper surface of the main shelf 40, except the edge of the main shelf 40 (the main water stop rib 43).

When the shoes are settled on the upper side of the main shelf 40, one part of the bottom surface of the shoes S comes into contact with the main isolation rib 42, and the other part docs not come into contact with the main isolation rib 42. A plurality of gaps are formed between the main isolation ribs 42, and steam or air may be supplied to the bottom of the shoes through such gaps during the management process of the shoes S. In addition, with the formation of the gaps, the condensed water on the upper surface of the main shelf 40 may flow without blocking the flow of the condensed water by the shoes.

The main shelf 40 is configured to include the main water stop rib 43 that forms an edge and protrudes upwards. The main water stop rib 43 may be formed on the entire edge of the main shelf 40. When the main shelf 40 in a plan view is formed in a rectangular shape, the main water stop rib 43 is formed in a rectangular shape.

The main water stop rib 43 may be formed in close contact with or close to the inner cabinet 100 at both left and right sides in the first direction (X direction).

With the formation of the main water stop rib 43, the condensed water on the upper side of the main shelf 40 may remain on the upper side of the main shelf 40 or flow toward the shelf hole 45 without departing from the main water stop rib 43 to the outside of the main shelf 40.

The steam inlet 204 may be located behind the main shelf 40 in the first direction (X direction). The steam inlet 204 may penetrate in the vertical direction, and the upper end thereof may be higher than the bottom of the main shelf 40.

The shoes care device 1 may include a bottom bar 295. The steam inlet 204 is formed on an upper surface of the bottom bar 295.

The bottom bar 295 may form the rearmost portion of the bottom surface of the accommodation space 101. The bottom bar 295 may be formed in a long shape along the second direction (Y direction).

The bottom bar 295 is interposed between the inner cabinet 100 and the main water stop rib 43 at the rear in the first direction (X direction). The bottom bar 295 may be in close contact between the inner cabinet 100 and the main water stop rib 43.

In one embodiment, the bottom bar 295 may be formed integrally with the module housing 200.

In another embodiment, the bottom bar 295 may be formed separately from the module housing 200 and then coupled to the module housing 200. The bottom bar 295 may be coupled to the module cover 202 of the module housing 200 at the rear in the first direction (X direction).

The steam inlet 204 may be formed at the rear of the module housing 200 based on the first direction (X direction), and can be formed in a form that vertically penetrates the module housing 200 and the bottom bar 295.

The upper surface of the bottom bar 295 may be formed to be higher than or equal to the upper surface of the main water stop rib 43.

The first inner side plate 120 of the inner cabinet 100 forms a wall surface on the side where the first guide rib **41*a*** is located based on the reference plane RP.

The second inner side plate 130 of the inner cabinet 100 forms a wall surface on the side where the second guide rib **41*b*** is located based on the reference plane RP.

The inner rear plate 110 of the inner cabinet 100 forms a wall surface at the rear in the first direction (X direction) and connects the first inner side plate 120 and the second inner side plate 130.

In the shoes care device 1 according to one embodiment of the present invention, the first guide rib **41*a* may be formed to be more biased toward the reference plane RP than the first inner side plate 120, and the second guide rib 41*b* may be formed to be more biased toward the reference plane RP than the second inner side plate 130**.

Accordingly, for ordinary-sized shoes, a pair of shoes S may be disposed side by side around the reference plane RP, and for very large-sized shoes, a pair of shoes S may be placed in a form opened to the rear in the first direction (X direction).

A length BD5 of the steam inlet 204 in the second direction (Y direction) may be configured to be 1/15 to 1/5 of a distance BD4 between the first inner side plate 120 and the second inner side plate 130. The length BD5 of the steam inlet 204 in the second direction (Y direction) may be configured to be 1/5 to 1/3 of the distance BD4 between the first inner side plate 120 and the second inner side plate 130.

According to the shoes care device 1 according to one embodiment of the present invention, foreign substances separated from the shoes during the shoe management process can be settled on the upper surface of the main shelf 40. Since the user can separate the main shelf 40 from the inner cabinet 100 to wash the main shelf 40, the shoes care device 1 can be easily maintained.

In the shoes care device 1 according to one embodiment of the present invention, the main shelf 40 is inclined downwards in the first direction (X direction), the shelf hole 45 is formed in the main shelf 40, and the condensed water on the upper surface of the main shelf 40 may flow into the module housing 200 through the shelf hole 45 and then move to the regeneration path F20. In addition, the shoes care device 1 may include the bottom bar 295, and the main shelf 40 may include the main water stop rib 43. In this case, the steam inlet 204 is formed on the upper surface of the bottom bar 295, the upper surface of the bottom bar 295 is formed higher than or equal to the upper surface of the main water stop rib 43, and the main water stop rib 43 is in close contact with to or close to the inner cabinet 100 on both left and right sides in the first direction (X direction). Accordingly, since the direction in which steam is discharged from the steam inlet 204 is not a direction directly facing the shoe, the stream is prevented from damaging the shoes. In addition, the condensed water condensed in the accommodation space 101 is located inside the main water stop rib 43 as the edge of the main shelf 40, or moves through a regeneration path, and the condensed water is easily managed in the shoes care device 1.

FIG. 22 is a view illustrating the inside of the module housing 200 according to one embodiment of the present invention. FIG. 22 illustrates that a schematic flow direction of air inside the module housing 200 is indicated by an arrow.

FIG. 23 is a view illustrating the inside of the module housing 200 according to one embodiment of the present invention. FIG. 23 illustrates the dehumidifying material cover 241 together.

FIG. 24 is a perspective view illustrating the drying module DM according to one embodiment of the present invention.

FIG. 25 is a bottom perspective view illustrating the dehumidifying material cover 241 illustrated in FIG. 24.

FIG. 26 is a cross-sectional view illustrating the drying module DM of FIG. 24.

FIGS. **27*a* and 27*b* are views illustrating simulation results of air speed distribution when an inner rib 250 is not formed in the module housing 200 according to one embodiment of the present invention, and FIGS. 28*a* and 28*b* are diagrams illustrating simulation results of the air speed distribution when the inner rib 250 is formed in the module housing 200** according to another embodiment of the present invention.

FIG. **29*a* is a view illustrating the entire area of the dehumidifying part divided into six areas (which are indicated by Nos. 1 to 6, and each of which is identified by one dotted line) in a plan view in the shoes care device 1 according to one embodiment of the present invention, and FIG. 29***b* is a view illustrating a mass flow rate in each area of FIG. 29*a*. In FIG. 29*b*, graph ① is a case where a fourth inner rib 254 and a fifth inner rib 255 are not formed, and graph ② is a case where the fourth inner rib 254 and the fifth inner rib 255 are formed.

As described above, the module housing 200 includes at least one module partition wall 220. The module partition wall 220 mutually partitions the first module chamber 212, the second module chamber 213, and the third module chamber 214 such that air moves sequentially through the first module chamber 212, the second module chamber 213, and the third module chamber 214.

In the shoes care device 1 according to one embodiment of the present invention, the module housing 200 may include at least one inner rib 250. The inner rib 250 is provided inside the module housing 200.

Each of the inner ribs 250 may be formed integrally with the module housing 200. Some or all of the inner ribs 250 may be formed integrally with the module case 201. Some or all of the inner ribs 250 may be formed integrally with the module cover 202. Some of the inner ribs 250 may be formed integrally with the dehumidifying material cover 241.

Each of the inner ribs 250 is formed in a plate shape inside the module housing 200 and is configured to guide the movement of air. That is, the inner rib 250 is configured such that the air inside the module housing 200 moves along the surfaces formed by each of the inner ribs 250.

Each of the inner ribs 250 may form a vertical surface. That is, the surface of the inner rib 250 may be formed in a vertical direction.

The inner rib 250 includes a first inner rib 251. The first inner rib 251 extends from the edge of the outlet 311*b* of the blowing part 310 to the edge of an inlet 320*a* of the heating part 320.

As described above, the outer flange 322*a* of the heater flange 322 may be formed in a tubular shape along the second direction (Y direction). In this case, in the outer flange 322*a*, the front in the second direction (Y direction) forms the inlet 320*a* of the heating part 320, and the rear in the second direction (Y direction) forms the outlet 320*b* of the heating part 320.

Two first inner ribs 251 can be provided, and the two first inner ribs 251 may be spaced apart from each other and formed on opposite sides of the outlet 311*b* of the blowing part 310. The two first inner ribs 251 may be formed in a shape where a gap between the first inner ribs 251 becomes narrow toward the inlet 320*a* of the heating part 320.

When air moves from the blowing part 310 to the heating part 320, the first inner rib 251 may prevent a vortex flow and avoid or minimize a head loss.

The inner rib 250 includes a second inner rib 252. The second inner rib 252 is formed in front of the outlet 320*b* of the heating part 320. The second inner rib 252 forms an inclined surface inclined from the second direction (Y direction) to the first direction (X direction). Accordingly, since the air passing through the outlet of the heating part 320 hits the second inner rib 252, the flow direction of the air can be naturally changed to the third module chamber 214 and the dehumidifying part 330.

Accordingly, with the formation of the second inner rib 252 in the module housing 200, the flow direction of the air from the heating part 320 to the dehumidifying part 330 can be effectively changed and the head loss can be minimized.

The module housing 200 may include a chamber inclined surface 213*a*. The chamber inclined surface 213*a* forms a bottom surface inclined upwards from the bottom surface of the second module chamber 213 to the dehumidifying part 330. The air that hits the second inner rib 252 and moves to the third module chamber 214 may move upwards along the chamber inclined surface 213*a*, and may also move to the upper side of the dehumidifying part 330.

The inner rib 250 includes a third inner rib 253. A plurality of third inner ribs 253 may be provided.

The third inner rib 253 may be formed between the second module chamber 213 and the third module chamber 214. The third inner rib 253 may be formed on the chamber inclined surface 213*a*.

The third inner rib 253 is formed parallel to the first direction (X direction), and the plurality of third inner ribs 253 are spaced apart from each other in the second direction (Y direction). Each of the third inner ribs 253 may have a length (a length in the first direction (X direction)) formed longer toward the second direction (Y direction).

The third inner rib 253 helps the air moving from the second module chamber 213 to the third module chamber 214 move parallel to the first direction (X direction), and allows the air to uniformly flow to the dehumidifying part 330 in the entire area of the dehumidifying part 330 the second direction (Y direction).

As described above, the dehumidifying part 330 may be disposed to be inclined downwardly toward the second module chamber 213. In this case, the dehumidifying part 330 and the dehumidifying material cover 241 are spaced apart from each other, and a space (the first flow path F10*aa*) is provided in the upper side of the dehumidifying part 330.

The inner rib 250 may include a fourth inner rib 254. The fourth inner rib 254 is disposed above the dehumidifying part 330 in the third module chamber 214. That is, the fourth inner rib 254 is disposed in the first flow path F10*aa*.

The fourth inner rib 254 is inclined from the first direction (X direction) to a direction opposite to the second direction (Y direction).

A plurality of fourth inner ribs 254 are provided and are repeatedly spaced apart from each other in the second direction (Y direction).

The inner rib 250 may include a fifth inner rib 255. The fifth inner rib 255 is disposed above the dehumidifying part 330 in the third module chamber 214. That is, the fifth inner rib 255 is disposed in the first flow path F10*aa*.

The fifth inner rib 255 is inclined from the first direction (X direction) to the second direction (Y direction).

A plurality of fifth inner ribs 255 are provided and are repeatedly spaced apart from each other in the second direction (Y direction).

The fifth inner rib 255 is positioned behind the fourth inner rib 254 with respect to the first direction (X direction). That is, the air moving from the second module chamber 213 to the third module chamber 214 may first pass through the fourth inner rib 254 and then through the fifth inner rib 255.

The vertical length of the fourth inner rib 254 may be formed longer than the vertical length of the fifth inner rib 255.

With respect to the second direction (Y direction), the fifth inner rib 255 positioned at the frontmost is positioned ahead of the fourth inner rib 254 at the frontmost, and the fifth inner rib 255 positioned at the rearmost is positioned behind or equal to the fourth inner rib 254 positioned at the rearmost.

In a plan view, the length of the fifth inner rib 255 is formed longer than the length of the fourth inner rib 254.

The fifth inner rib 255 may be divided into a fifth-first inner rib 255*a* and a fifth-second inner rib 255*b*. The fifth-first inner ribs 255*a* form a first row. The fifth-second inner rib 255*b* is positioned behind the fifth-first inner rib 255*a* with respect to the first direction (X direction) and forms a second row.

With respect to the second direction (Y direction), a length from the rear end of the dehumidifying part 330 to the fifth inner rib 255 positioned at the frontmost may be ½ to ⅘ of a length from the rear end of the dehumidifying part 330 to the front end thereof.

In the shoes care device 1 according to one embodiment of the present invention, the fourth inner rib 254 and the fifth inner rib 255 may be formed on the bottom surface of the module cover 202.

As described above, in the shoes care device 1 according to the embodiment of the present invention, the module cover 202 may include the dehumidifying material exit 240 and the dehumidifying material cover 241. In this case, the fourth inner rib 254 and the fifth inner rib 255 may be integrally formed on the bottom surface of the dehumidifying material cover 241.

In the shoes care device 1 according to one embodiment of the present invention, the fourth inner rib 254 forms a surface resistant to the air moving in the opposite direction to the first direction (X direction) from the upper side of the dehumidifying part 330. The fourth inner rib 254 may reduce the deviation of the flow rate between the air moving through the front part of the dehumidifying part 330 and the air moving through the rear part of the dehumidifying part 330 with respect to the first direction (X direction).

In addition, the fifth inner rib 255 forms a surface resistant to the air moving in a direction opposite to the first direction (X direction) from the upper side of the dehumidifying part 330. The fifth inner rib 255 may further reduce the deviation of the flow rate between the air moving through the front part of the dehumidifying part 330 and the air moving through the rear part of the dehumidifying part 330 with respect to the first direction (X direction).

In addition, the air moving from the second module chamber 213 to the third module chamber 214 may be widely dispersed along the second direction (Y direction) by the fifth inner rib 255. Accordingly, the air of the third module chamber 214 may pass through the dehumidifying part 330 at a uniform speed over the entire area of the dehumidifying part 330.

In FIGS. 27*a* and 28*a*, a blue (a dark color when an image is displayed in black and white) portion indicates a portion having a relatively low flow rate. In FIG. 27*a*, it can be seen that the flow rate of the lower left part is lower than other parts, and the deviation of the flow rate of the dehumidifying part 330 is slightly larger for each area on the plane. In FIG. 28*a*, it can be seen that the deviation of the flow rate of the dehumidifying part 330 is smaller for each area on the plane as compared to FIG. 27*a*.

In FIGS. 27*b* and 28*b*, a red (dark color when an image is displayed in black and white) portion indicates a portion having a relatively high flow rate.

As a result of simulation of the shoes care device 1 according to one embodiment of the present invention, as compared to FIGS. 27*a* and 27*b* (when the inner rib 250 is not formed inside the module housing 200), FIGS. 28*a* and 28*b* (when the inner rib 250 is formed inside the module housing 200) has confirmed that the wind volume is improved by about 0.7% inside the module housing 200. That is, it can be seen that the wind volume of the air moving in the module housing 200 in a case in which the inner rib 250 is formed is improved by about 0.7% as compared to a case in which the inner rib 250 is not formed, and the air inside the module housing 200 is smoother circulated.

Also, as a result of checking a pressure loss of the inlet (the first flow path F10*aa*) of the dehumidifying part 330 compared to the outlet 311*b* of the blowing part 310, as compared to the pressure loss of FIG. 27*b* (when the inner rib 250 is not formed inside the module housing 200), FIG. 28*b* (when the inner rib 250 is formed inside the module housing 200) has confirmed that the pressure loss was reduced by about 9%. That is, it can be seen that the pressure loss of air flowing inside the module housing 200 in a case in which the first inner rib 251, the second inner rib 252, and the third inner rib 253 are formed is reduced by about 9% as compared to a case in which the first inner rib 251, the second inner rib 252, and the third inner rib 253 are not formed.

In addition, as a result of checking a pressure loss of the outlet (the first flow path F10*ab*) of the dehumidifying part 330 compared to the inlet (the first flow path F10*aa*) of the dehumidifying part 330, as compared to the pressure loss of FIG. 27*a* (when the inner rib 250 is not formed inside the module housing 200), FIG. 28*a* (when the inner rib 250 is formed inside the module housing 200) has confirmed that the pressure loss was increased by about 27%. That is, it can be seen that the pressure loss of air flowing inside the module housing 200 in a case in which the fourth inner rib 254 and the fifth inner rib 255 are formed is increased by about 9% as compared to a case in which the fourth inner rib 254 and the fifth inner rib 255 are not formed, and the flow rate decreases when the air penetrates the dehumidifying part 330 in the third module chamber 214.

In addition, as shown in FIG. 29*b* in this case, it can be seen that when the fourth inner rib 254 and the fifth inner rib 225 are not formed (①), the deviation of the mass flow rate of the dehumidifying part 330 for each area is relatively large, and when the fourth inner rib 254 and the fifth inner rib 225 are formed (②), the deviation of the mass flow rate of the third module chamber 214 for each area is relatively small.

When the fourth inner rib 254 and the fifth inner rib 255 are not formed (①), the mass flow rate is relatively very high in a third region of the dehumidifying part 330 and the mass flow rate is relatively very low in a fourth area. However, when the fourth inner rib 254 and the fifth inner rib 255 are formed (②), the mass flow rate is decreased in the third area of the dehumidifying part 330 and the mass flow rate is increased in the fourth area. The deviation for each area can be seen to decrease.

As such, it can be seen that when the fourth inner rib 254 and the fifth inner rib 255 are formed compared to when the fourth inner rib 254 and the fifth inner rib 255 are not formed, flow uniformity is excellent in each area of the dehumidifying part 330, and the air passes uniformly through each area of the dehumidifying part 330 in the third module chamber 214.

According to one embodiment of the present invention, with the formation of the fourth inner rib 254 and the fifth inner rib 255, the dehumidifying part 330 can be efficiently utilized.

As described above, according to one embodiment of the present invention, air may smoothly move in the module chamber by the inner rib 250, and an unnecessary head loss, a vortex flow, etc., may be prevented from occurring in the module chamber.

Hereinabove, a specific embodiment of the present invention is described and illustrated, but the present invention is not limited to the disclosed embodiment, and it may be appreciated by those skilled in the art that the exemplary embodiment can be variously modified and transformed to another specific embodiment without departing from the spirit and the scope of the present invention. Therefore, the scope of the present invention will not be defined by the described embodiment, but defined by the technical spirit disclosed in the claims.

INDUSTRIAL APPLICABILITY

According to an embodiment of the present disclosure, since the steam inlet is located at the rear center of the accommodation space, it is possible to minimize the possibility that the shoes cover the steam inlet when a pair of shoes is placed on the bottom of the accommodation space, and the steam may be supplied uniformly to the respective shoes. In addition, even when high-temperature steam is discharged through the steam inlet, the steam is discharged directly to the bottom of the shoe, thereby minimizing the possibility of uneven processing of a pair of shoes or damage to the shoes.

The invention claimed is:

1. A shoes care device comprising:

an inner cabinet having an accommodation space configured to accommodate shoes therein, the inner cabinet having a main opening that is open in a first direction from a rear to a front of the inner cabinet;

a door configured to open and close the main opening;

a connection path defining a flow path through which air in the accommodation space is introduced from the main opening thereinto and then discharged therefrom into the accommodation space;

a blower located in the connection path, the blower being configured to move the air along the connection path;

a dehumidifier located in the connection path, the dehumidifier being configured to dehumidify the air in the connection path;

a steam generator configured to generate steam;

a steam inlet in communication with the accommodation space, the steam inlet being located at a lateral center of the accommodation space and being located closer to a rear end of the accommodation space than to a longitudinal center, with respect to the first direction, on a bottom of the accommodation space or adjacent to the bottom of the accommodation space; and a first guide rib and a second guide rib protruding upward from a bottom surface of the accommodation space so as to support a front end or a rear end of a corresponding shoe accommodated in the accommodation space, wherein the first guide rib and the second guide rib are positioned on different sides of the accommodation space based on a reference plane that is a vertical plane parallel to the first direction and crossing the steam inlet.

2. The shoes care device according to claim 1, wherein the bottom surface of the accommodation space is inclined downward in the first direction, and wherein each of the first guide rib and the second guide rib is formed in a curved shape that is concave in the first direction.

3. The shoes care device according to claim 1, wherein the first guide rib and the second guide rib are symmetrical to each other about the reference plane and are located at a front of the accommodation space based on the first direction.

4. The shoes care device according to claim 3, wherein, based from the rear end of the bottom surface of the accommodation space in the first direction, when a distance to the steam inlet is BD1, a distance to the first guide rib and the second guide rib is BD2, and a distance to a front end of the bottom surface of the accommodation space is BD3, the BD1 is 10% or less of the BD3, and the BD2 is 90% to 100% of the BD3.

5. The shoes care device according to claim 3, wherein opposite sides of the accommodation space are symmetrical about the reference plane.

6. The shoes care device according to claim 3, wherein the inner cabinet further comprises:

a first inner side plate configured to define a first wall surface on a side where the first guide rib is positioned based on the reference plane;

a second inner side plate configured to define a second wall surface on a side where the second guide rib is positioned based on the reference plane; and an inner rear plate configured to define a rear wall surface connecting the first inner side plate and the second inner side plate.

7. The shoes care device according to claim 6, wherein the first guide rib is closer to the reference plane than the first inner side plate, and wherein the second guide rib is closer to the reference plane than the second inner side plate.

8. The shoes care device according to claim 6, wherein a length of the steam inlet in a second direction perpendicular to the first direction is $\frac{1}{15}$ to $\frac{1}{5}$ of a gap between the first inner side plate and the second inner side plate in the second direction.

9. The shoes care device according to claim 1, wherein the inner cabinet further comprises:

a lower opening provided in a lower part of the accommodation space;

a module housing coupled to a lower side of the inner cabinet to shield the lower opening, the module housing defining a portion of the connection path; and a main shelf seated on an upper side of the module housing, the first guide rib and the second guide rib being located on an upper surface of the main shelf.

10. The shoes care device according to claim 9, wherein the module housing includes:

an opening through which the air in the accommodation space is introduced into the module housing; and a module chamber located therein, the module chamber including an inner space in communication with the opening, the blower and the dehumidifier being located in the inner space.

11. The shoes care device according to claim 10, wherein the opening is located at a front of the upper surface of the module housing in the first direction, and wherein the main shelf has a shelf hole located above the opening.

12. The shoes care device according to claim 11, wherein the first guide rib and the second guide rib are located in front of the shelf hole in the first direction.

13. The shoes care device according to claim 12, wherein the main shelf comprises a plurality of isolation ribs protruding from the upper surface of the main shelf.

14. The shoes care device according to claim 13, wherein the plurality of isolation ribs extend in an oblique direction between the main opening and the rear of the inner cabinet.

15. The shoes care device according to claim 13, wherein the main shelf comprises a main water stop rib extending along an edge of the main shelf.

16. The shoes care device according to claim 15, further comprising a bottom bar located between the inner cabinet and the main water stop rib at a rear of the inner cabinet, the steam inlet being located at an upper surface of the bottom bar, the steam inlet being located between the inner cabinet and the main water stop rib at the rear of the accommodation space, wherein the upper surface of the bottom bar is higher than or a same height as an upper surface of the main water stop rib, and wherein the main water stop rib is adjacent to both left and right sides of the inner cabinet.

17. The shoes care device according to claim 10, wherein the steam inlet is located behind the main shelf in the first direction, extends in a vertical direction, and has an upper end that is higher than a bottom of the main shelf.

18. The shoes care device according to claim 10, further comprising:

a sump located at a lower side of the module housing, the sump being configured to accommodate condensed water;

a heater located in the module chamber, the heater being configured to heat the air in the module chamber; and a regeneration path defining a path for the air of the module chamber passing through the dehumidifier to move to the sump.

19. The shoes care device according to claim 1, wherein the module housing includes:

a module case defining a portion of the module chamber; and a module cover coupled to the module case, the module cover being configured to cover an upper side of the blower, the heater, and the dehumidifier, the module cover having the opening through which the air in the accommodation space is introduced into the module housing.

* * * * *